US011234632B2

(12) United States Patent
Naor et al.

(10) Patent No.: US 11,234,632 B2
(45) Date of Patent: Feb. 1, 2022

(54) BRAIN NAVIGATION LEAD

(71) Applicant: Alpha Omega Engineering Ltd., Nof HaGalil (IL)

(72) Inventors: Omer Naor, Kiryat-Tivon (IL); Adi Balan, Haifa (IL); Hagai Bergman, Jerusalem (IL); Imad Younis, Nazareth Ilit (IL); Oren A. Gargir, Calgary (CA); Zvi Israel, Jerusalem (IL); Jubran Elfar, Nazareth (IL); Paul Mcsherry, Woodbury, MN (US); Steven Scott, Excelsior, MN (US); Benjamin Matter, Ham Lake, MN (US)

(73) Assignee: Alpha Omega Engineering Ltd., Nof HaGalil (IL)

( * ) Notice: Subject to any disclaimer, the term of this patent is extended or adjusted under 35 U.S.C. 154(b) by 44 days.

(21) Appl. No.: 16/084,664

(22) PCT Filed: Mar. 14, 2017

(86) PCT No.: PCT/IL2017/050328
§ 371 (c)(1),
(2) Date: Sep. 13, 2018

(87) PCT Pub. No.: WO2017/158604
PCT Pub. Date: Sep. 21, 2017

(65) Prior Publication Data
US 2019/0069797 A1  Mar. 7, 2019

Related U.S. Application Data

(63) Continuation-in-part of application No. PCT/US2016/031448, filed on May 9, 2016.
(Continued)

(51) Int. Cl.
*A61B 5/377* (2021.01)
*A61B 5/00* (2006.01)
(Continued)

(52) U.S. Cl.
CPC .............. *A61B 5/377* (2021.01); *A61B 5/24* (2021.01); *A61B 5/6868* (2013.01); *A61B 5/374* (2021.01);
(Continued)

(58) Field of Classification Search
None
See application file for complete search history.

(56) References Cited

U.S. PATENT DOCUMENTS

| 4,603,696 A | 8/1986 | Cross, Jr. et al. |
| 5,097,835 A | 3/1992 | Putz |

(Continued)

FOREIGN PATENT DOCUMENTS

| CN | 101516436 | 8/2009 |
| CN | 101829400 | 9/2010 |

(Continued)

OTHER PUBLICATIONS

International Preliminary Report on Patentability dated Jan. 17, 2019 From the International Bureau of WIPO Re. Application No. PCT/IL2017/050763. (8 Pages).
(Continued)

*Primary Examiner* — Carl H Layno
*Assistant Examiner* — Manolis Pahakis

(57) ABSTRACT

A brain navigation device, comprising a lead with an elongated lead body, at least one macro-electrode contact positioned on an outer surface on the lead, wherein the at least one macro-electrode contact is located at the distal part of
(Continued)

the lead, and wherein the at least one macro-electrode contact is configured to be used during lead navigation.

20 Claims, 47 Drawing Sheets
(16 of 47 Drawing Sheet(s) Filed in Color)

Related U.S. Application Data

(60) Provisional application No. 62/459,415, filed on Feb. 15, 2017, provisional application No. 62/459,422, filed on Feb. 15, 2017, provisional application No. 62/307,835, filed on Mar. 14, 2016, provisional application No. 62/159,336, filed on May 10, 2015.

(51) Int. Cl.
  *A61B 5/24* (2021.01)
  *A61N 1/05* (2006.01)
  *A61N 1/36* (2006.01)
  *A61B 5/374* (2021.01)

(52) U.S. Cl.
  CPC ..... *A61B 5/7217* (2013.01); *A61B 2562/0209* (2013.01); *A61B 2562/0223* (2013.01); *A61B 2562/043* (2013.01); *A61B 2562/046* (2013.01); *A61B 2562/182* (2013.01); *A61N 1/0534* (2013.01); *A61N 1/36067* (2013.01)

(56) References Cited

U.S. PATENT DOCUMENTS

| | | | |
|---|---|---|---|
| 5,458,629 A | 10/1995 | Baudino et al. | |
| 5,584,873 A | 12/1996 | Shoberg et al. | |
| 5,713,922 A | 2/1998 | King | |
| 5,833,709 A | 11/1998 | Rise et al. | |
| 5,843,148 A | 12/1998 | Gijsbers et al. | |
| 6,011,996 A * | 1/2000 | Gielen | A61N 1/0529 |
| | | | 600/378 |
| 6,253,109 B1 | 6/2001 | Gielen | |
| 6,301,492 B1 * | 10/2001 | Zonenshayn | A61B 5/04001 |
| | | | 600/378 |
| 7,033,326 B1 | 4/2006 | Pianca et al. | |
| 7,047,084 B2 | 5/2006 | Erickson et al. | |
| 7,177,701 B1 | 2/2007 | Pianca | |
| 7,450,992 B1 * | 11/2008 | Cameron | A61N 1/0551 |
| | | | 607/46 |
| 7,668,601 B2 | 2/2010 | Hegland et al. | |
| 7,783,359 B2 | 8/2010 | Meadows | |
| 7,809,446 B2 | 10/2010 | Meadows | |
| 7,877,150 B2 | 1/2011 | Hoegh et al. | |
| 7,917,231 B2 | 3/2011 | Farah et al. | |
| 7,941,202 B2 | 5/2011 | Hetke et al. | |
| 8,000,808 B2 | 8/2011 | Hegland et al. | |
| 8,295,944 B2 | 10/2012 | Howard et al. | |
| 8,364,272 B2 | 1/2013 | Goetz | |
| 8,452,415 B2 | 5/2013 | Goetz et al. | |
| 8,473,061 B2 | 6/2013 | Moffitt et al. | |
| 8,498,718 B2 | 7/2013 | Meadows | |
| 8,532,757 B2 | 9/2013 | Molnar et al. | |
| 8,538,513 B2 | 9/2013 | Molnar et al. | |
| 8,548,602 B2 | 10/2013 | Moffitt et al. | |
| 8,694,127 B2 | 4/2014 | Pianca et al. | |
| 8,739,403 B2 | 6/2014 | Hegland et al. | |
| 8,755,905 B2 | 6/2014 | Meadows | |
| 8,755,906 B2 | 6/2014 | Moffitt et al. | |
| 8,788,064 B2 | 7/2014 | Mercanzini et al. | |
| 8,792,972 B2 | 7/2014 | Zaidel et al. | |
| 8,874,232 B2 | 10/2014 | Chen | |
| 8,938,308 B2 | 1/2015 | Meadows | |
| 8,977,367 B2 | 3/2015 | Elahi et al. | |
| 9,199,090 B2 | 12/2015 | Goetz et al. | |
| 2001/0014820 A1 * | 8/2001 | Gielen | A61N 1/0534 |
| | | | 607/116 |
| 2003/0083724 A1 * | 5/2003 | Jog | A61N 1/0536 |
| | | | 607/122 |
| 2003/0212691 A1 | 11/2003 | Kuntala et al. | |
| 2005/0065427 A1 | 3/2005 | Magill et al. | |
| 2005/0246004 A1 * | 11/2005 | Cameron | A61N 1/0553 |
| | | | 607/116 |
| 2006/0265039 A1 * | 11/2006 | Bartic | A61N 1/0531 |
| | | | 607/116 |
| 2008/0039709 A1 | 2/2008 | Karmarkar | |
| 2008/0082109 A1 | 4/2008 | Moll et al. | |
| 2008/0243214 A1 | 10/2008 | Koblish | |
| 2008/0243219 A1 | 10/2008 | Malinowski et al. | |
| 2009/0054941 A1 | 2/2009 | Eggen et al. | |
| 2009/0118806 A1 * | 5/2009 | Vetter | A61B 5/24 |
| | | | 607/116 |
| 2009/0276005 A1 * | 11/2009 | Pless | A61N 1/36071 |
| | | | 607/46 |
| 2010/0160771 A1 | 6/2010 | Gielen et al. | |
| 2010/0241020 A1 | 9/2010 | Zaidel et al. | |
| 2010/0292602 A1 | 11/2010 | Worrell et al. | |
| 2011/0160797 A1 | 6/2011 | Makous et al. | |
| 2011/0295350 A1 | 12/2011 | Mercanzini et al. | |
| 2011/0301665 A1 | 12/2011 | Mercanzini et al. | |
| 2012/0046710 A1 | 2/2012 | DiGiore et al. | |
| 2012/0046715 A1 | 2/2012 | Moffitt et al. | |
| 2012/0053659 A1 | 3/2012 | Molnar et al. | |
| 2012/0101537 A1 | 4/2012 | Peterson et al. | |
| 2012/0101552 A1 | 4/2012 | Lazarewicz et al. | |
| 2012/0184837 A1 * | 7/2012 | Martens | A61B 5/0478 |
| | | | 600/378 |
| 2012/0296230 A1 | 11/2012 | Davis et al. | |
| 2013/0066331 A1 | 3/2013 | Chitre et al. | |
| 2013/0096642 A1 | 4/2013 | Wingeier | |
| 2013/0123600 A1 * | 5/2013 | Tcheng | A61B 5/4839 |
| | | | 600/378 |
| 2014/0309714 A1 | 10/2014 | Mercanzini et al. | |
| 2015/0031982 A1 | 1/2015 | Piferi et al. | |
| 2015/0065839 A1 | 3/2015 | Farah et al. | |
| 2015/0066006 A1 | 3/2015 | Srivastava | |
| 2015/0265180 A1 | 9/2015 | Venkatesan et al. | |
| 2016/0045748 A1 | 2/2016 | Astrom et al. | |
| 2017/0158604 A1 | 9/2017 | Naor et al. | |
| 2018/0125585 A1 | 5/2018 | Mechael et al. | |
| 2019/0069797 A1 * | 3/2019 | Naor | A61B 5/377 |
| 2019/0321106 A1 * | 10/2019 | Bergman | A61N 1/0551 |
| 2021/0282869 A1 | 9/2021 | Bergman et al. | |

FOREIGN PATENT DOCUMENTS

| | | |
|---|---|---|
| CN | 102245253 | 11/2011 |
| CN | 104622468 | 5/2015 |
| CN | 104703653 | 5/2021 |
| EP | 0832667 | 4/1998 |
| EP | 2144665 | 1/2010 |
| JP | 2004-261569 | 9/2004 |
| JP | 2012-531936 | 12/2012 |
| WO | WO 99/36122 | 7/1999 |
| WO | WO 2008/133615 | 11/2008 |
| WO | WO 2011/001322 | 1/2011 |
| WO | WO 2015/173787 | 11/2015 |
| WO | WO 2016/182997 | 11/2016 |
| WO | WO 2018/008034 | 1/2018 |

OTHER PUBLICATIONS

Supplementary European Search Report and the European Search Opinion dated Dec. 6, 2018 From the European Patent Office Re. Application No. 16793310.0. (7 Pages).
Corrected International Search Report and the Written Opinion dated Dec. 20, 2016 From the International Searching Authority Re. Application No. PCT/US2016/031448. (9 Pages).
International Preliminary Report on Patentability dated Nov. 23, 2017 From the International Bureau of WIPO Re. Application No. PCT/US2016/031448. (7 Pages).
International Preliminary Report on Patentability dated Sep. 27, 2018 From the International Bureau of WIPO Re. Application No. PCT/ IL2017/050328. (8 Pages).

(56) References Cited

OTHER PUBLICATIONS

International Search Report and the Written Opinion dated Nov. 3, 2016 From the International Searching Authority Re. Application No. PCT/US2016/031448. (9 Pages).
International Search Report and the Written Opinion dated Aug. 11, 2017 From the International Searching Authority Re. Application No. PCT/ IL2017/050328. (18 Pages).
International Search Report and the Written Opinion dated Nov. 27, 2017 From the International Searching Authority Re. Application No. PCT/IL2017/050763. (15 Pages).
Invitation to Pay Additional Fees dated Jun. 8, 2017 From the International Searching Authority Re. Application No. PCT/IL2017/050328. (2 Pages).
Invitation to Pay Additional Fees dated Sep. 13, 2017 From the International Searching Authority Re. Application No. PCT/IL2017/050763. (2 Pages).
Chaturvedi et al. "Current Steering to Activate Targeted Neural Pathways During Deep Brain Stimulation of the Subthalamic Region", Brain Stimulation, 5(3): 369-377, Jul. 2015.
Chen et al. "Intra-Operative Recordings of Local Field Potentials Can Help Localize the Subthalamic Nucleus in Parkinson's Disease Surgery", Experimental Neurology, 198(1): 214-221, Available Online Jan. 5, 2006.
Chen et al. "Intra-Operative Recordings of Local Field Potentials Can Help Localize the Subthalamic Rucleus in Parkinson's Disease Surgery", Experimental Neurology 198: 214-221, 2006.
Connolly et al. "Spatial Resolution and Heterogeneity of Local Field Potentials in the Globus Pallidus", 6th Annual International IEEE EMBS Conference on Neural Engineering, San Diego, CA, USA, Nov. 6-8, 2013, p. 129-132, Nov. 6, 2013.
Firat Ince et al. "Selection of Optimal Programming Contacts Based on Local Field Potential Recordings From Subthalamic Nucleus in Patients With Parkinson's Disease", Neurosurgery, 67(2): 390-397, Aug. 2010.
Hariz "Deep Brain Stimulation: New Techniques", Parkinsonism and Related Disorders 20(1): 192-196, Jan. 2014.
Klostermann et al. "Identification of Target Areas for Deep Brain Stimulation in Human Basal Ganglia Substructures Based on Median Nerve Sensory Evoked Potential Criteria", Journal of Neurology, Neurosurgery and Psychiatry, 74(8): 1031-1035, Aug. 2003.
Lempka et al. "Theoretical Analysis of the Local Field Potential in Deep Brain Stimulation Applications", PLOS One, 8(3): e59839-1-e59839-12, Mar. 28, 2013.
Litvak et al. "Optimized Beamforming for Simultaneous MEG and Intracranial Local Field Potential Recordings in Deep Brain Stimulation Patients", NeuroImage, 50(4): 1578-1588, Available Online Jan. 4, 2010.
Marmor et al. "Local Vs. Volume Conductance Activity of Field Potentials in the Human Subthalamic Nucleus", Journal of Neurophysiology, 117(6): 2140-2151, Published Online Feb. 15, 2017.
Moran et al. "Real-Time Refinement of Subthalamic Nucleus Targeting Using Bayesian Decision-Making on the Root Mean Square Measure", Movement Disorders, 21(9): 1425-1431, Published Online Jun. 8, 2006.
Rabiner "A Tutorial on Hidden Markov Models and Selected Applications in Speech Recognition", Proceedings of the IEEE, 77(2): 257-286, Feb. 1989.
Telkes et al. "Localization of Subthalamic Nucleus Borders Using Macroelectrode Local Field Potential Recordings",36th Annual International Conference of the IEEE Engineering in Medicine and Biology Society: 2621-2624, Aug. 2014.
Telkes et al. "Localization of Subthalamic Nucleus Borders Using Nacroelectrode Local Field Potential Recordings", 2014 36th Annual International Conference of the IEEE Engineering in Medicine and Biology Society, EMBC, Chicago, IL, USA, Aug. 26-30, 2014, p. 2621-2624, Aug. 26, 2014.
Telkes et al. "Prediction of STN-DBS Electrode Implantation Track in Parkinson's Diseaseby Using Local Field Potentials", Frontiers in Neuroscience, 10(198): 1-16, May 9, 2016.
Trottenberg et al. "Frequency-Dependent Distribution of Local Field Potential Activity Within the Subthalamic Nucleus in Parkinson's Disease", Experimental Neurology, 205(1): 287-291, Available Online Feb. 6, 2007.
Valsky et al. "Stop! Border Ahead: Automatic Detection of Subthalamic Exit During Deep Brain Stimulation Surgery", Movement Disorder, 32(1): 70-79, Published Online Oct. 6, 2016.
Winestone et al. "The Use of Macroelectrodes in Recording Cellular Spiking Activity", Journal of Neuroscience Methods, 266(1): 34-39, Apr. 30, 2012.
Yoshida et al. "Value of Subthalamic Nucleus Local Field Potentials Recordings in Predicting Stimulation Parameters for Deep Brain Stimulation in Parkinson's Disease", Journal of Neurology, Neurosurgery and Psychiatry, 81(8): 885-889, Published Online May 12, 2010.
Zaidel et al. "Delimiting Subterritories of the Human Subthalamic Nucleus by Means of Microelectrode Recordings and A Hidden Markov Model", Movement Disorders, 24(12): 1785-1793, Published Online Jun. 16, 2009.
Zaidel et al. "Subthalamic Span of Beta Oscillations Predicts Deep Brain Stimulation Efficacy for Patients With Parkinson's Disease", Brain, 133(Pt.7): 2007-2021, Advance Access Publication Jun. 9, 2010.
Supplementary European Search Report and the European Search Opinion dated Mar. 10, 2020 From the European Patent Office Re. Application No. 17823773.1. (8 Pages).
Supplementary European Search Report and the European Search Opinion dated Sep. 23, 2019 From the European Patent Office Re. Application No. 17765991.9. (8 Pages).
Notification of Office Action and Search Report dated Sep. 21, 2020 From the State Intellectual Property Office of the People's Republic of China Re. Application No. 201780029771.5. (11 Pages).
Official Action dated Sep. 11, 2020 from the US Patent and Trademark Office Re. U.S. Appl. No. 16/315,714. (25 pages).
Notice of Reasons for Rejection dated Feb. 18, 2020 From the Japan Patent Office Re. Application No. 2017-557984 and Its Translation Into English. (9 Pages).
Official Action dated Jan. 6, 2020 From the US Patent and Trademark Office Re. U.S. Appl. No. 15/572,799 (23 pages).
Notification of Office Action and Search Report dated Mar. 31, 2020 From the State Intellectual Property Office of the People's Republic of China Re. Application No. 201680039601.0. (6 Pages).
Official Action dated Apr. 13, 2020 from the US Patent and Trademark Office Re. U.S. Appl. No. 15/572,799. (13 pages).
Translation Dated Apr. 20, 2020 of Notification of Office Action dated Mar. 31, 2020 From the State Intellectual Property Office of the People's Republic of China Re. Application No. 201680039601.0. (2 Pages).
Notification of Office Action dated Dec. 1, 2020 From the State Intellectual Property Office of the People's Republic of China Re. Application No. 201680039601.0 and Its Translation Into English. (6 Pages).
European Search Report and the European Search Opinion dated Oct. 30, 2020 From the European Patent Office Re. Application No. 20170479.8. (8 Pages).
Notice of Reasons for Rejection dated Oct. 6, 2020 From the Japan Patent Office Re. Application No. 2017-557984 and Its Translation Into English. (5 Pages).
Translation Dated Oct. 22, 2020 of Notification of Office Action dated Sep. 21, 2020 From the State Intellectual Property Office of the People's Republic of China Re. Application No. 201780029771.5. (9 Pages).
Notification of Office Action and Search Report dated Mar. 24, 2021 From the State Intellectual Property Office of the People's Republic of China Re. Application No. 201780029771.5. (11 Pages).
Translation Dated May 18, 2021 of Notification of Office Action dated May 8, 2021 From the State Intellectual Property Office of the People's Republic of China Re. Application No. 201780045640.6. (2 Pages).
Communication Pursuant to Article 94(3) EPC dated Apr. 20, 2021 From the European Patent Office Re. Application No. 17823773.1. (8 Pages).

(56) References Cited

OTHER PUBLICATIONS

Notification of Divisional Application dated May 8, 2021 From the State Intellectual Property Office of the People's Republic of China Re. Application No. 201780045640.6and Its English Summary. (3 Pages).
Translation Dated Apr. 15, 2021 of Notification of Office Action dated Mar. 24, 2021 From the State Intellectual Property Office of the People's Republic of China Re. Application No. 201780029771.5. (9 Pages).
Notification of Office Action and Search Report dated Aug. 31, 2021 From the State Intellectual Property Office of the People's Republic of China Re. Application No. 201780045640.6.(11 Pages).
Translation dated Sep. 7, 2021 of Notification of Office Action dated Aug. 6, 2021 From the State Intellectual Property Office of the People's Republic of China Re. Application No. 201780029771.5. (8 Pages).
Translation dated Sep. 18, 2021 of Notification of Office Action dated Aug. 31, 2021 From the State Intellectual Property Office of the People's Republic of China Re. Application No. 201780045640.6. (11 Pages).
Communication Pursuant to Article 94(3) EPC dated Nov. 9, 2021 From the European Patent Office Re. Application No. 17823773.1. (7 Pages).

* cited by examiner

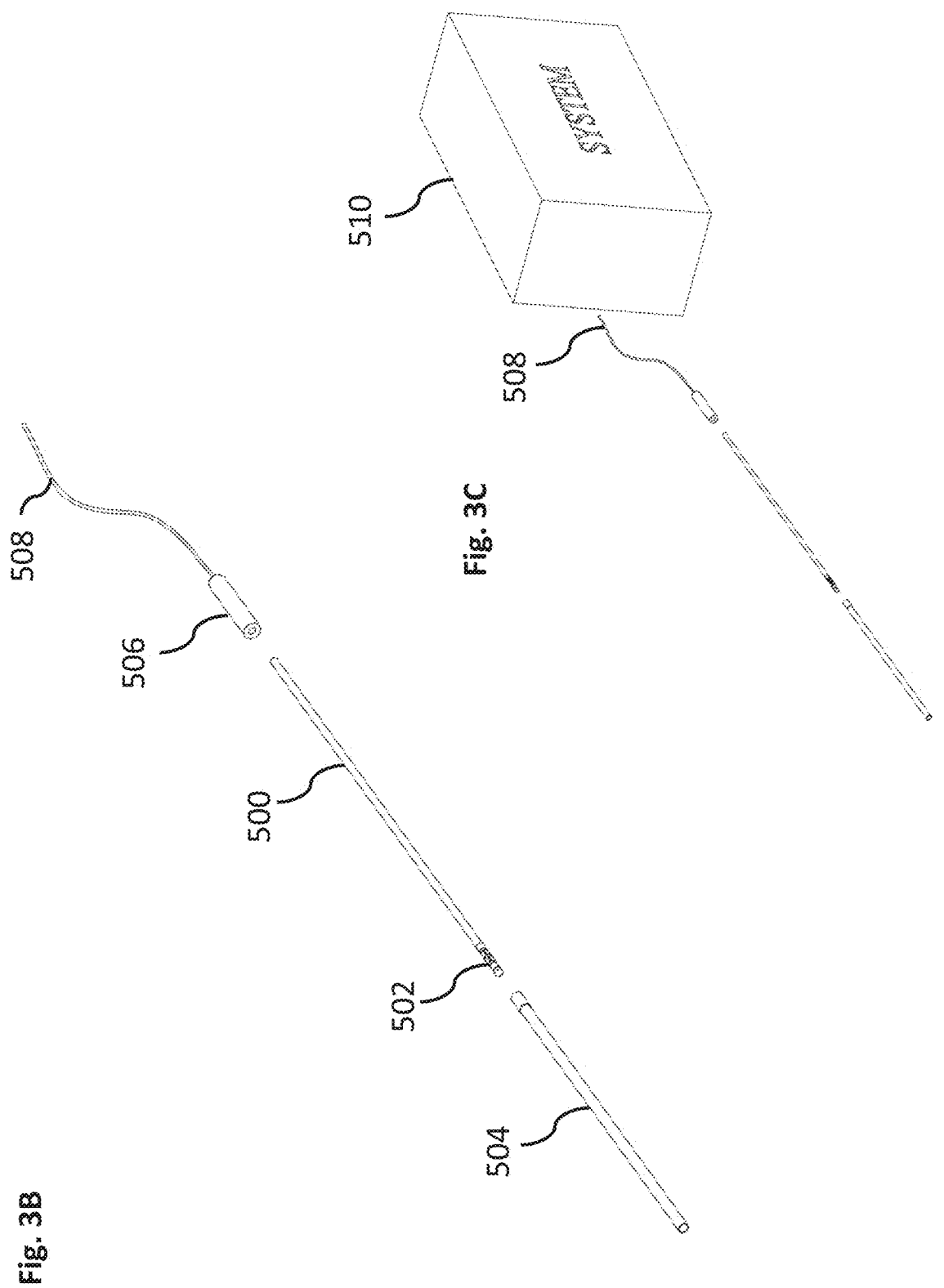

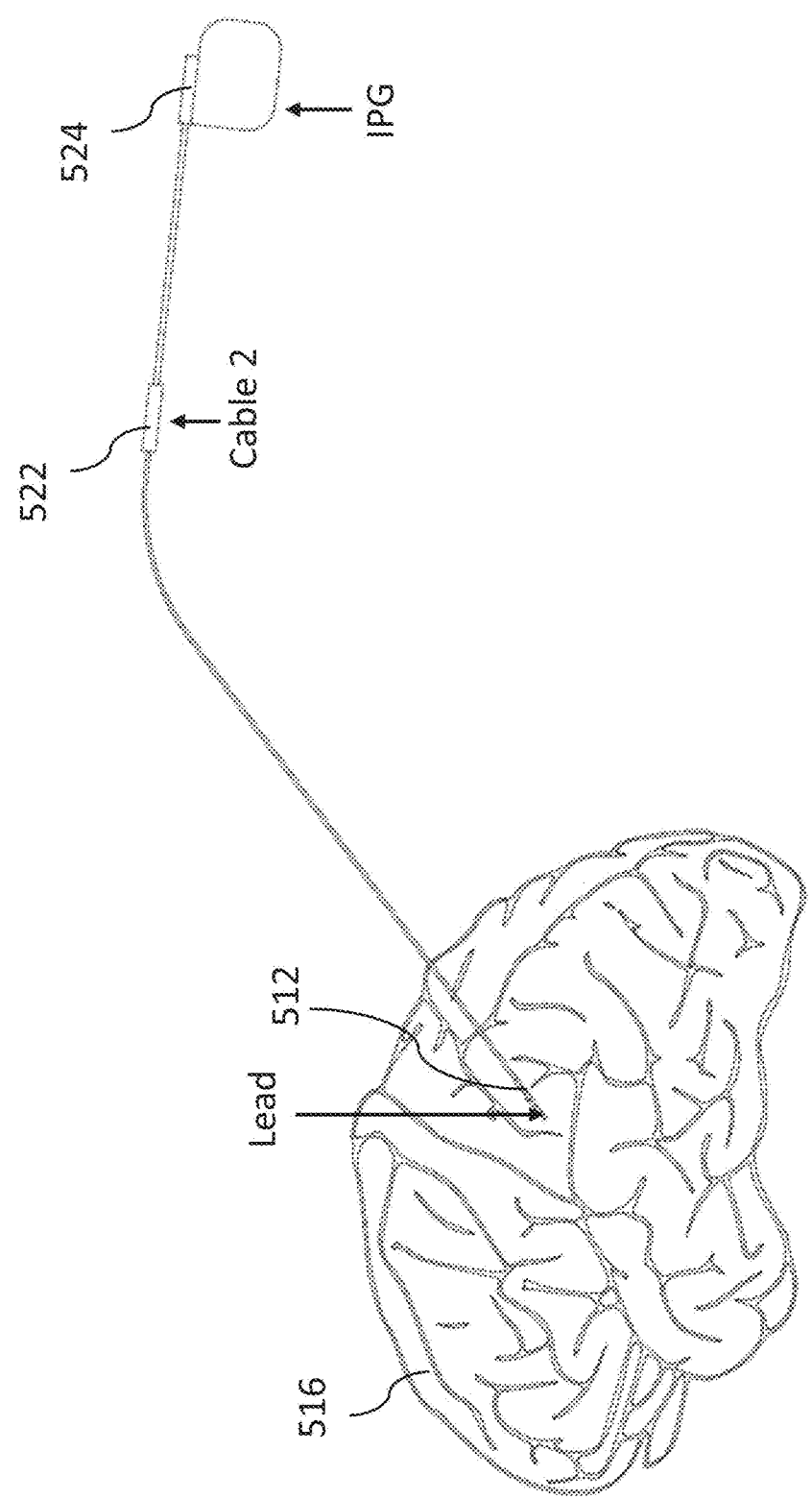

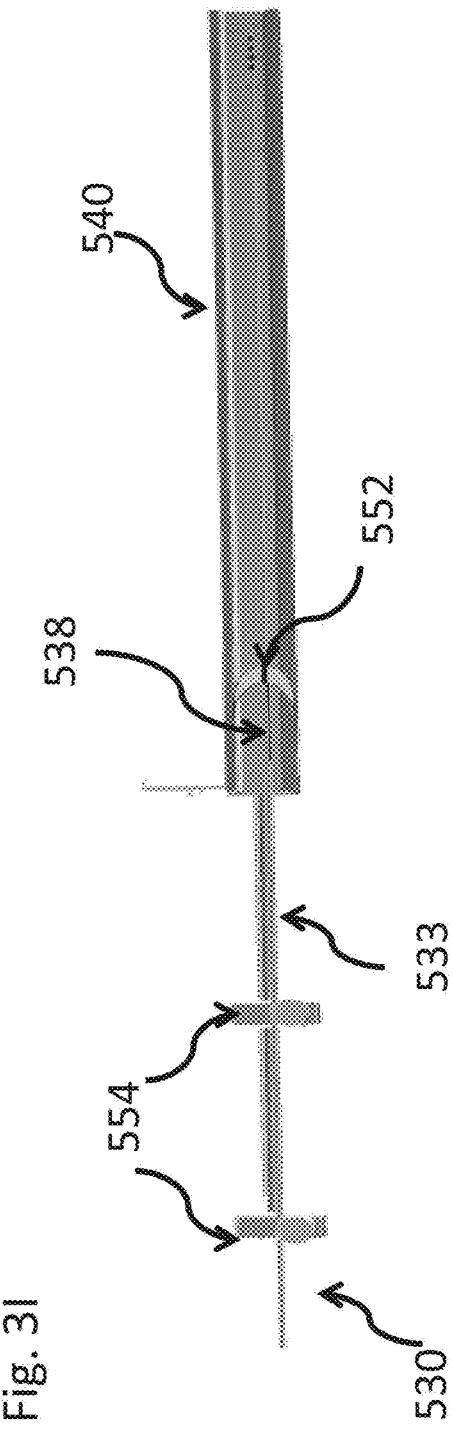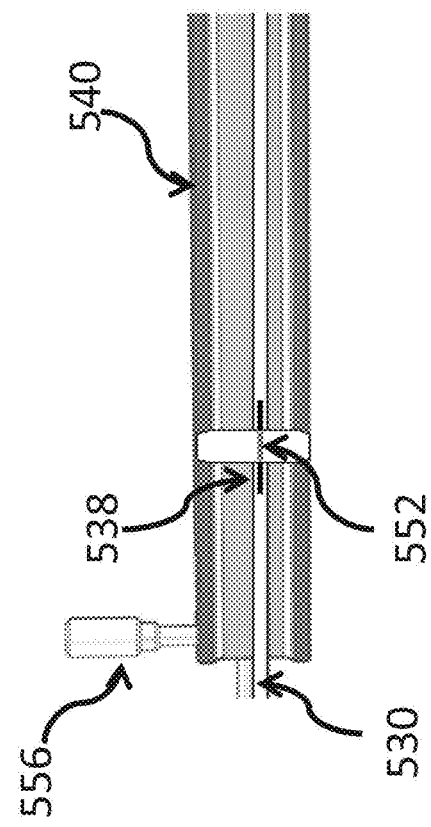

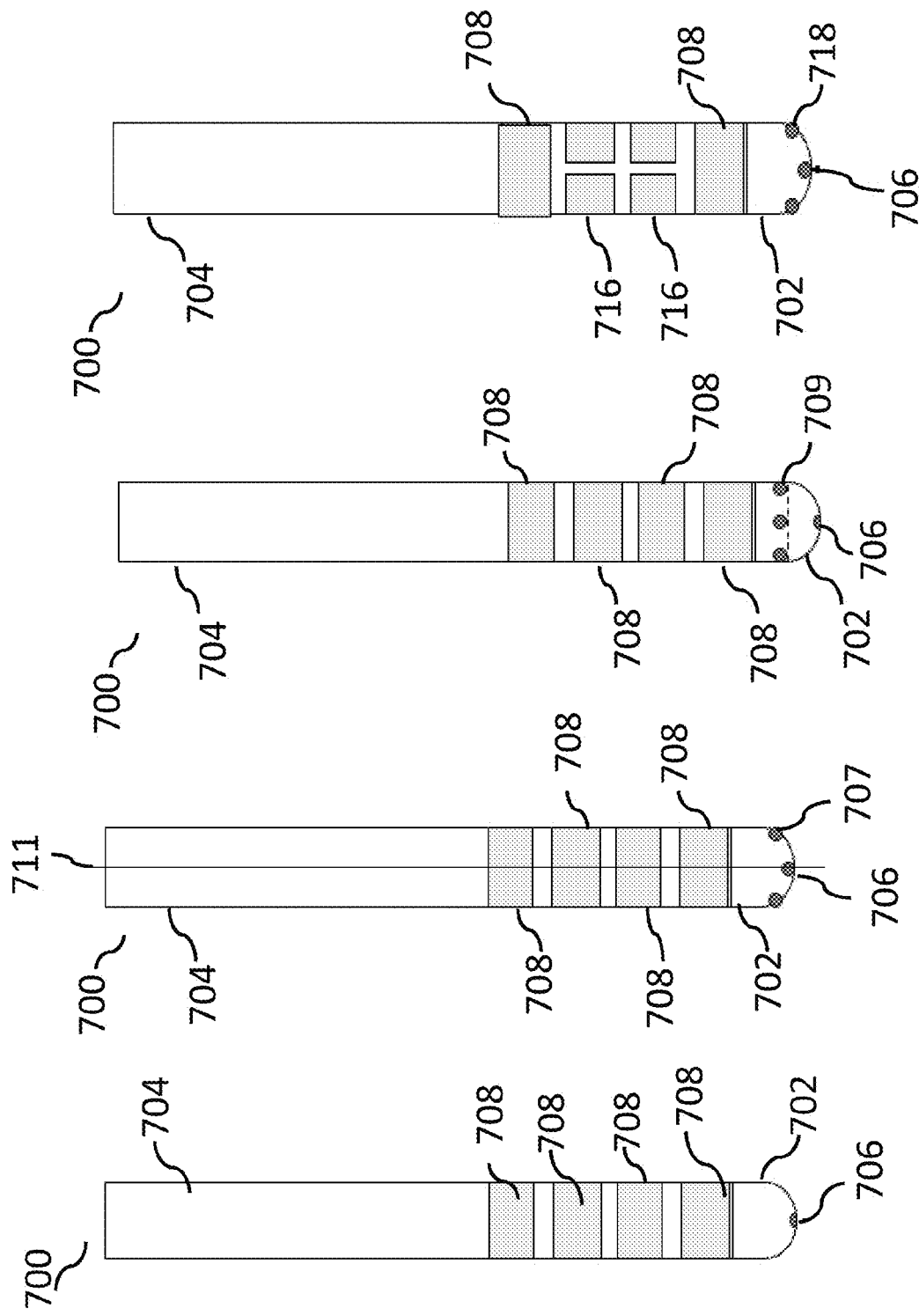

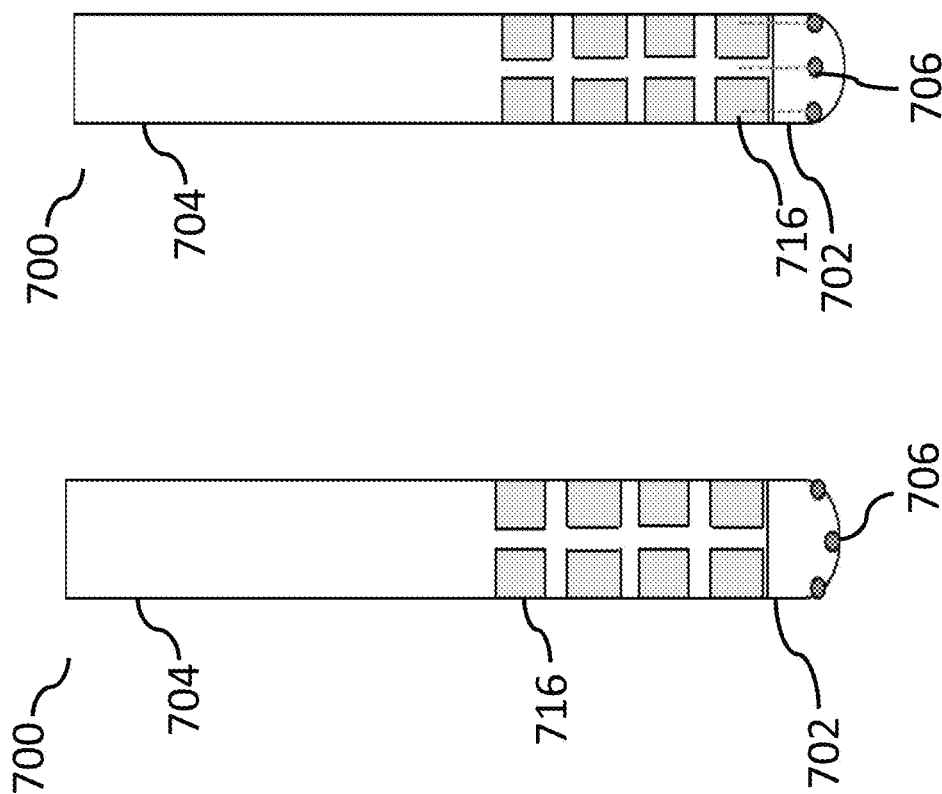
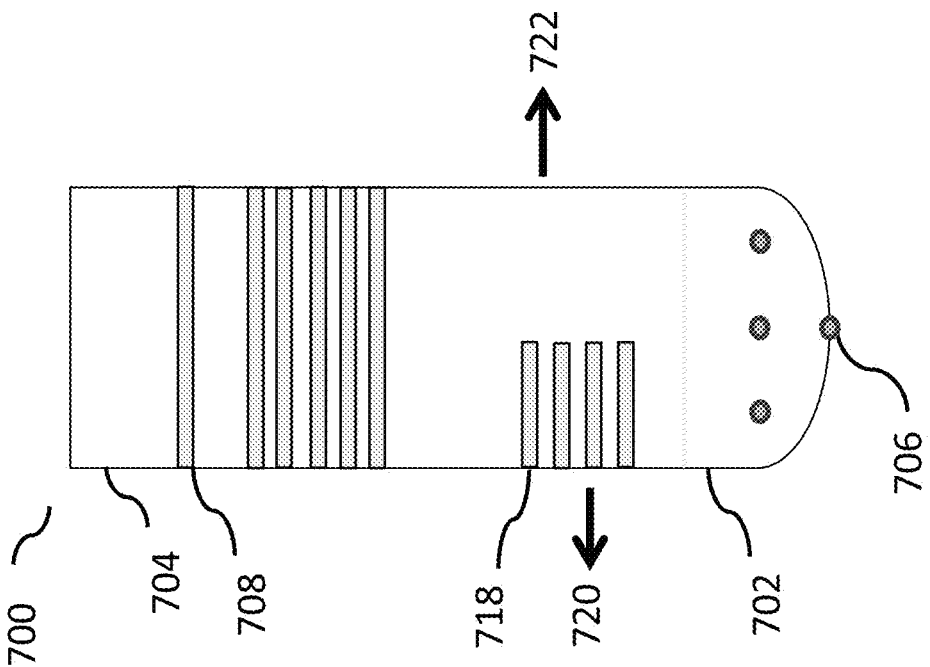

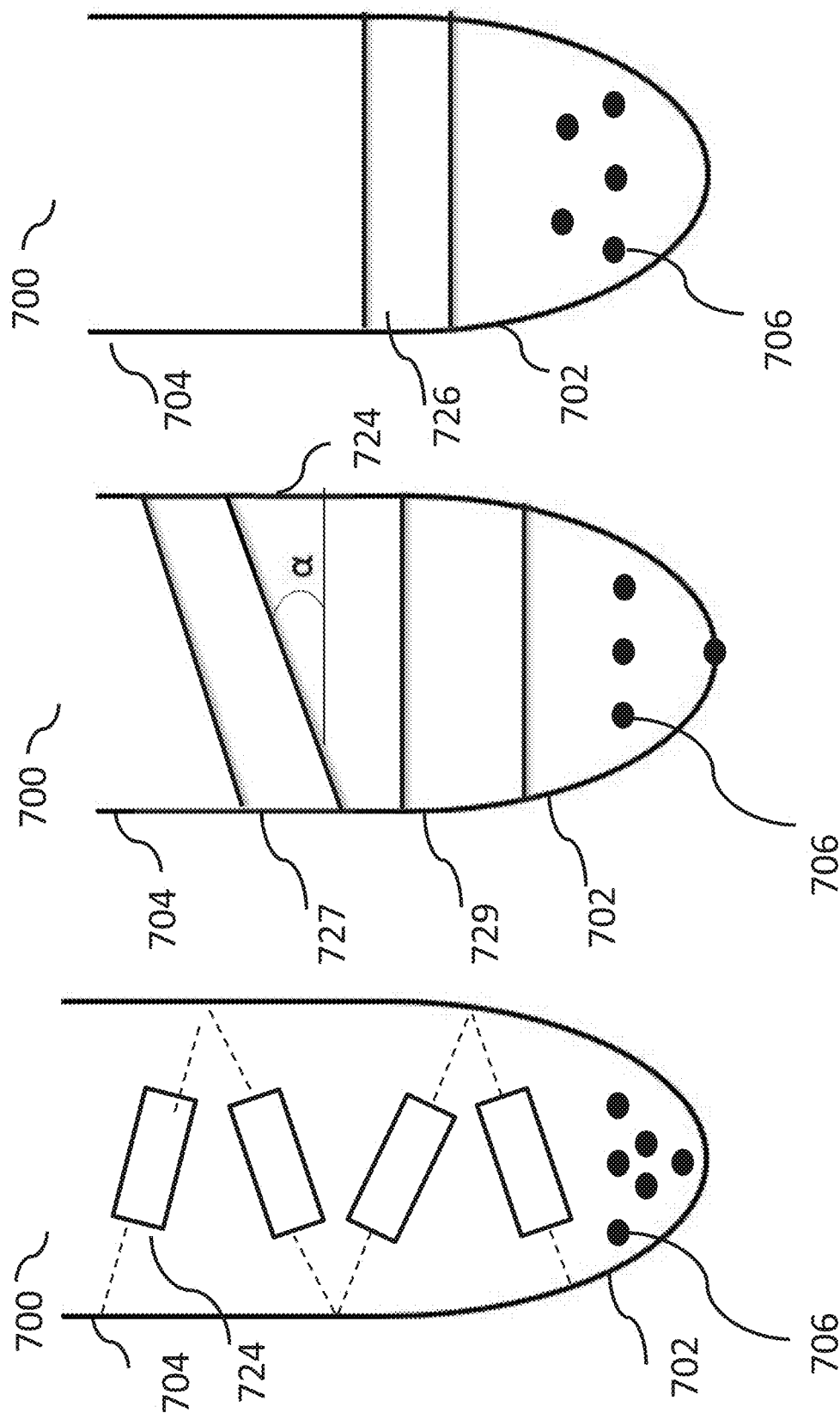

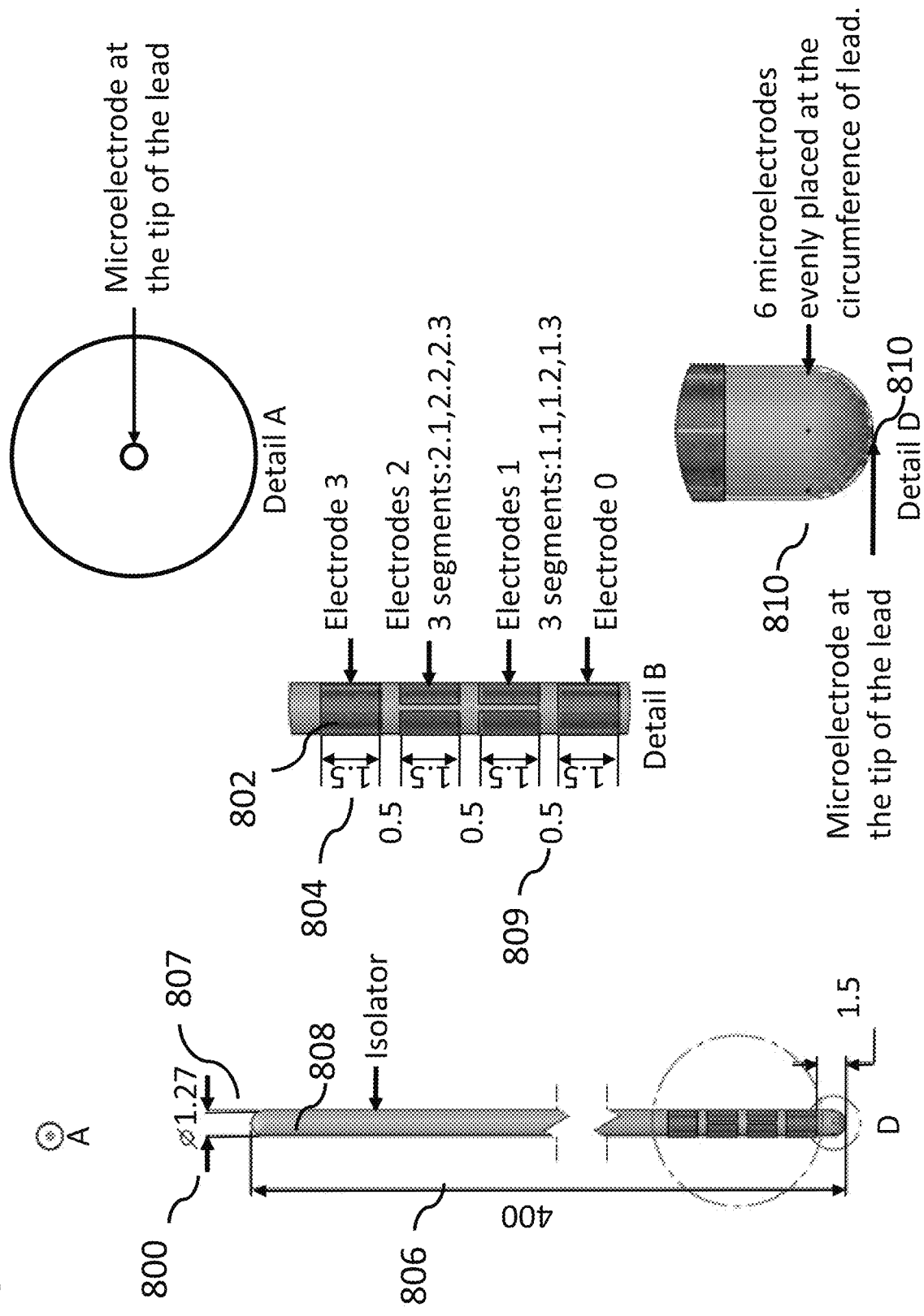

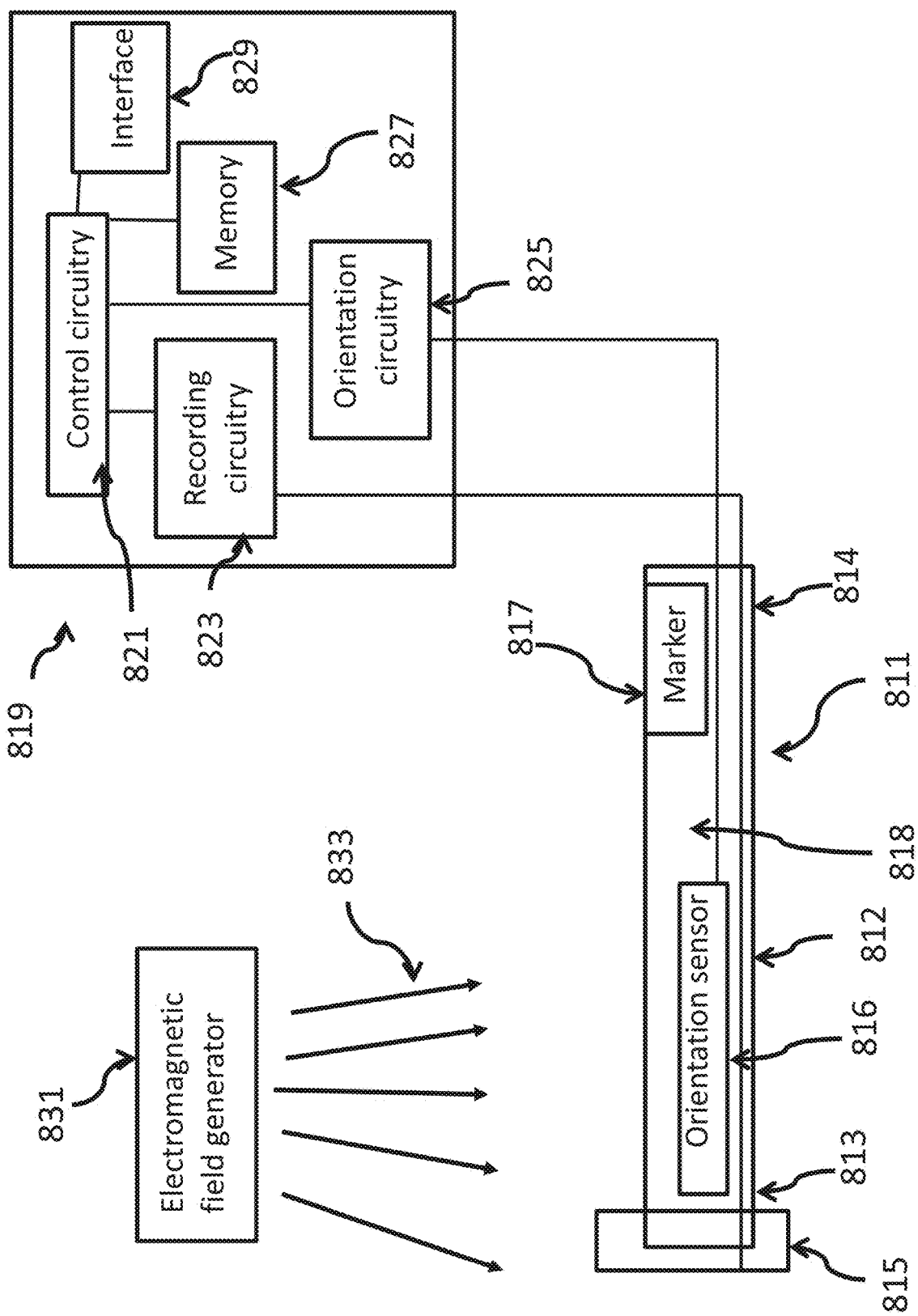

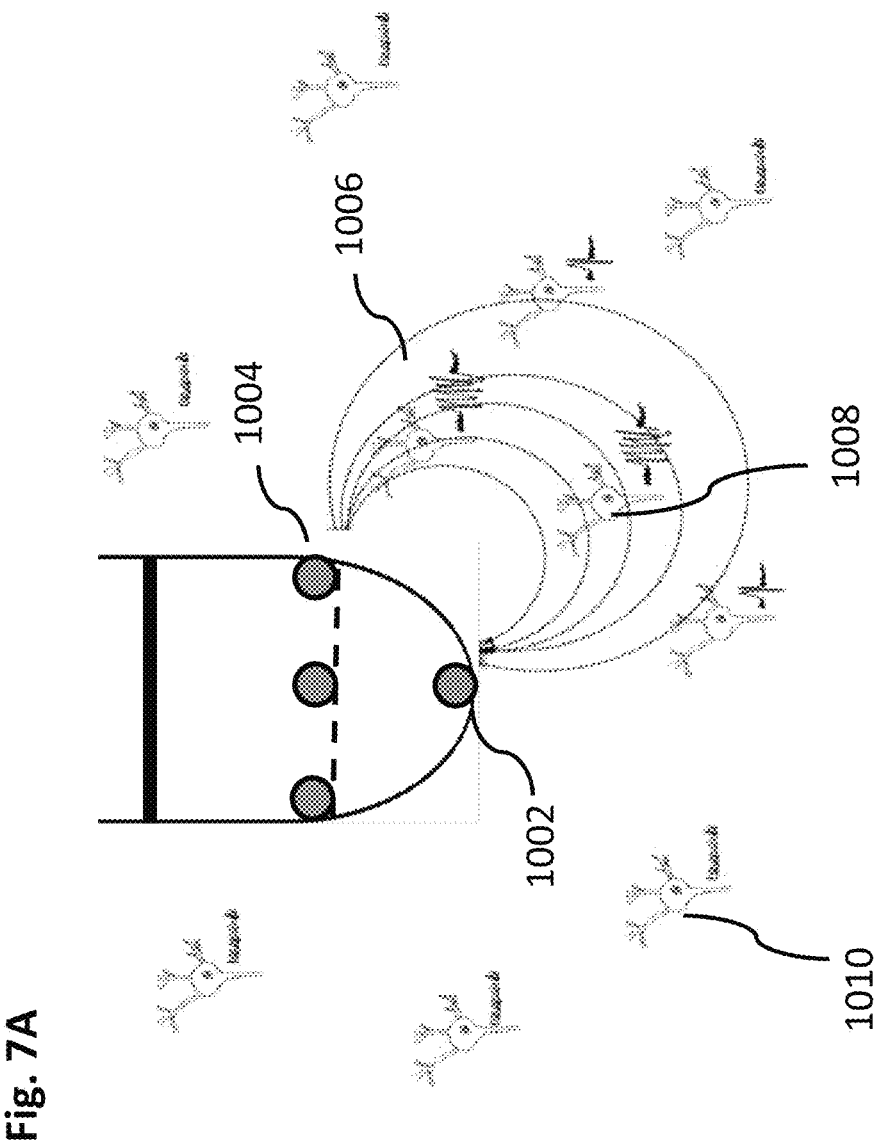

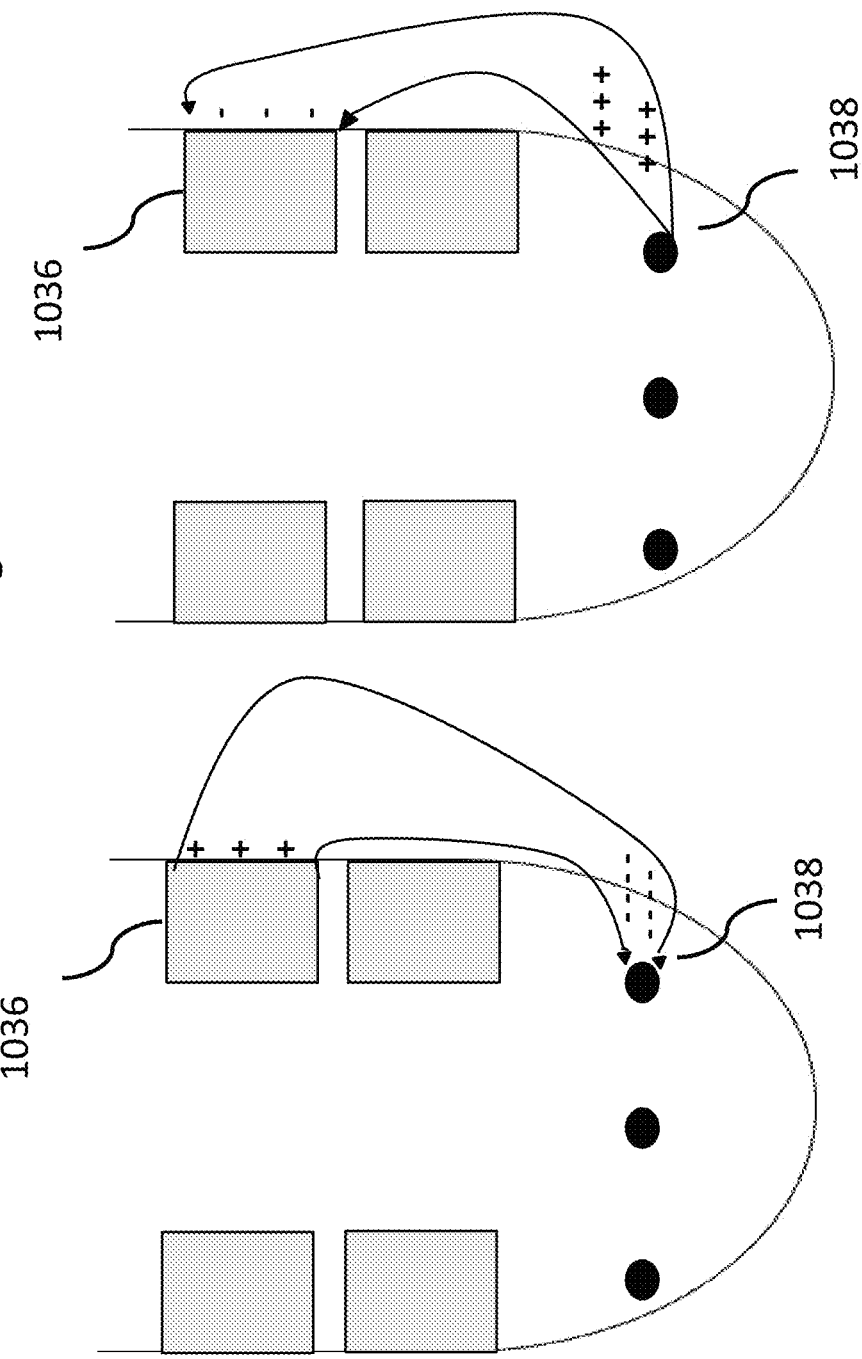

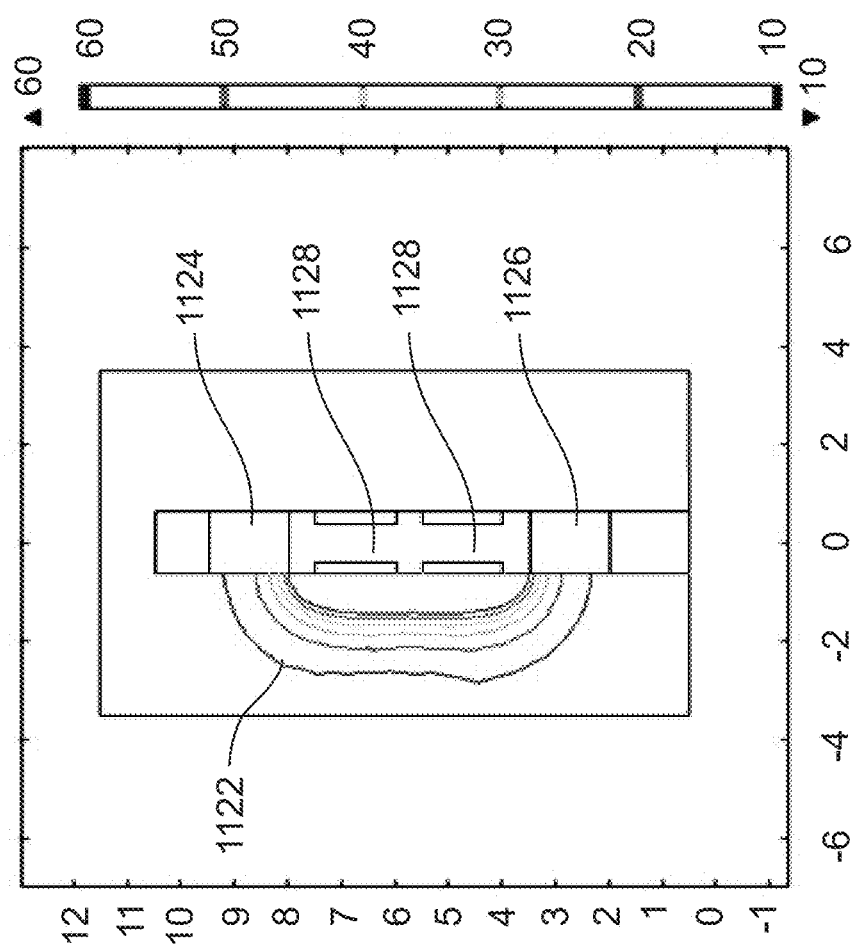

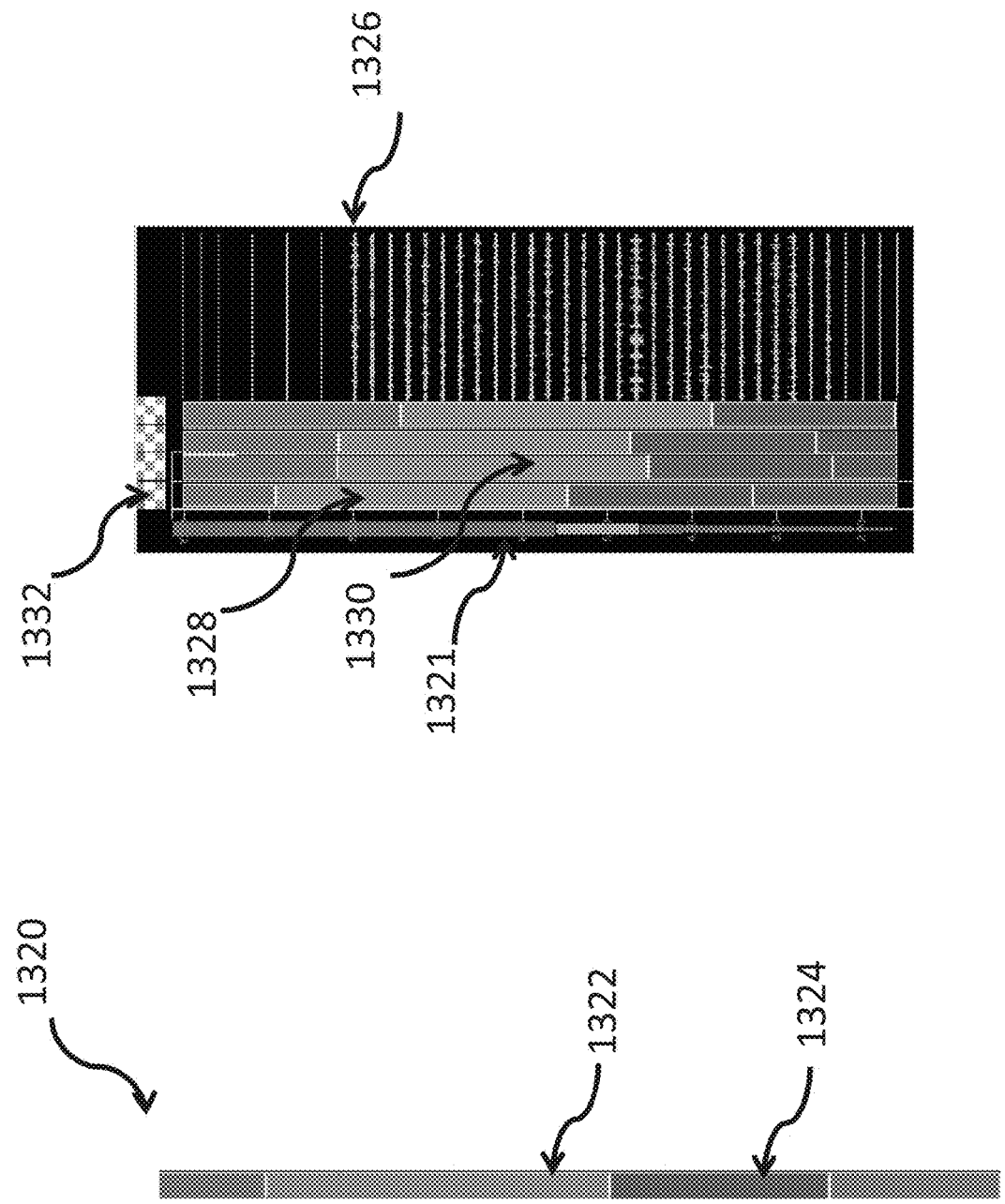

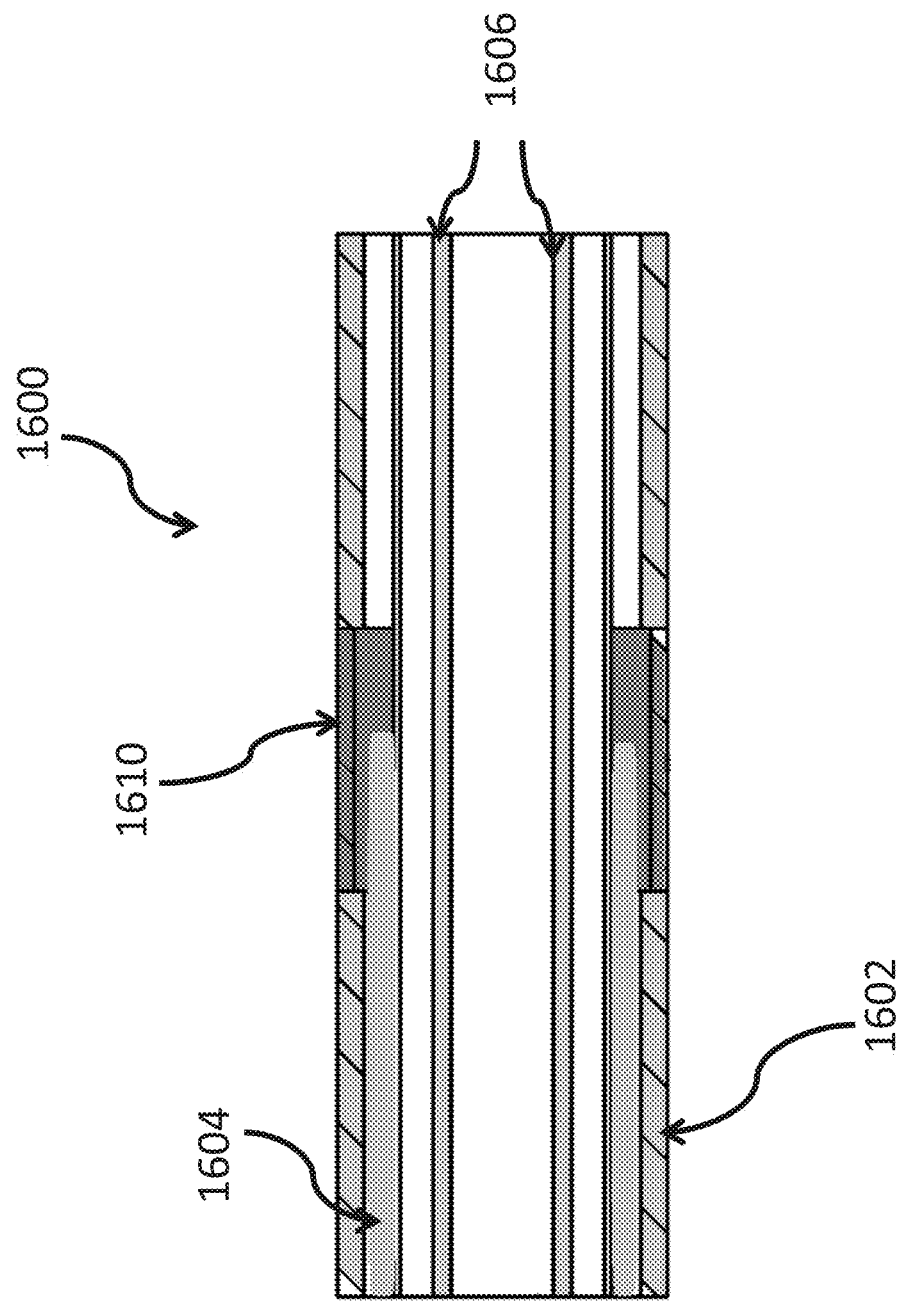

BRAIN NAVIGATION LEAD

RELATED APPLICATIONS

This application is a National Phase of PCT Patent Application No. PCT/IL2017/050328 having International filing date of Mar. 14, 2017, which claims the benefit of priority under 35 USC § 119(e) of U.S. Provisional Patent Application Nos. 62/459,415 and 62/459,422, both filed on Feb. 15, 2017 and 62/307,835 filed on Mar. 14, 2016.

PCT Patent Application No. PCT/IL2017/050328 is also a Continuation-In-Part (CIP) of PCT Patent Application No. PCT/US2016/031448 filed on May 9, 2016, which claims the benefit of priority under 35 USC § 119(e) of U.S. Provisional Patent Application No. 62/159,336 filed on May 10, 2015.

The contents of the above applications are all incorporated by reference as if fully set forth herein in their entirety.

FIELD AND BACKGROUND OF THE INVENTION

The present invention, in some embodiments thereof, relates to a brain navigation lead and system and/or parts thereof and, more particularly, but not exclusively, to a brain navigation lead comprising electrode contacts and configured to measure electrical activity of brain tissue.

Electric field application to the brain is under increasing use for such varied purposes as treatment of neurological and psychiatric conditions. A typical electrical brain stimulation system comprises a pulse generator operatively connected to the brain by a lead. Prior to electric field application, an electrode is used to determine the desired target location for electric field application. Then, the navigation lead is removed and a second electrode for applying the electric field is inserted.

SUMMARY OF THE INVENTION

Following are some examples of some embodiments of the invention. Features of one example may be combined with one or more features and/or other examples:

EXAMPLE 1

A brain navigation device, comprising:
a lead having an elongated lead body
at least one macro-electrode contact positioned on an outer surface on said lead;
wherein said at least one macro-electrode contact is located at the distal part of said lead;
and wherein said at least one macro-electrode contact is configured to be used during lead navigation.

EXAMPLE 2

The device according to example 1, wherein said lead is used for navigation in the spinal cord.

EXAMPLE 3

The device according to example 1, further comprising at least one microelectrode contact, wherein said at least one microelectrode contact and said at least one macro-electrode contact are configured to be used during lead navigation.

EXAMPLE 4

The device according to example 1, wherein said at least one macro-electrode contact is configured to be used during lead navigation through brain tissue.

EXAMPLE 5

The device according to example 3, wherein said at least one micro-electrode contact is located at the distal tip of said lead.

EXAMPLE 6

The device according to example 1, wherein said at least one macro-electrode contact are configured to apply an electric field.

EXAMPLE 7

The device according to example 3, wherein said at least one micro-electrode contact is located distally to said at least one macro-electrode contact.

EXAMPLE 8

The lead according to example 1, wherein said at least one macro-electrode contact comprises at least one ring electrode contact and/or at least one segmented electrode contact.

EXAMPLE 9

A method for recording and applying an electric field to brain tissue using brain navigation lead, comprising:
selecting at least one electrode contact and/or at least one macro-electrode contact adjacent to a desired tissue region and/or facing a desired direction;
recording electrical activity of said desired tissue; and
applying an electric field to said desired tissue.

EXAMPLE 10

The method of example 9, further comprising:
recording electrical activity of desired tissue following electric field application.

EXAMPLE 11

The method of example 9, further comprising:
determining electric field application parameters based on recorded electrical activity.

EXAMPLE 12

The method according to example 9, further comprising:
determining desired depth for electric field application based on recorded electrical activity.

EXAMPLE 13

A brain navigation lead with an elongated body, comprising:
at least one electrode contact positioned on the outer surface of said lead;
at least one marker located at the proximal end of said lead in a position that remains visible to a user during a lead navigation process;

wherein said marker indicates a relative orientation of said at least one electrode contact relative to brain tissue surrounding said lead when said lead is inserted into the brain.

EXAMPLE 14

The lead according to example 13, wherein said marker is shaped and sized to be aligned with an alignment marker of an external device associated with said lead.

EXAMPLE 15

The lead according to example 14, wherein said external device is selected from a list consisting of a lead holder, a DBS-ruler or a cannula.

EXAMPLE 16

The lead according to example 13, wherein said marker comprises at least two visually detectable markers which indicate an angle between two points on said outer surface on said lead.

EXAMPLE 17

The lead according to example 13, wherein said marker includes a line, an arrow, an ellipsoid or a rectangle.

EXAMPLE 18

The lead according to example 13, wherein said marker is attached to said lead using a reflow process.

EXAMPLE 19

A brain navigation lead with an elongated body, comprising:
at least one electrode contact positioned on the outer surface of said lead;
at least one orientation sensor;
wherein said sensor indicates a relative spatial orientation of said at least one electrode contact relative to brain tissue surrounding said lead when said lead is inserted into the brain.

EXAMPLE 20

The lead according to example 19, wherein said sensor is located within 30 mm of said electrode contact.

EXAMPLE 21

The lead according to example 19, wherein said sensor is electrically connected to a system, wherein said system determines the position in space of signals recorded by said electrode contact based on indications from said sensor.

EXAMPLE 22

The lead of example 19, wherein said sensor is connected to an external control system via electrical wires.

EXAMPLE 23

The lead of example 19, wherein said sensor comprises a wireless sensor configured to transmit signals to a wireless receiver positioned outside of the head by wireless communication.

EXAMPLE 24

The lead of example 19, wherein said sensor comprises at least one coiled wire and wherein said sensor detects changes in the resistance of said coiled wire when said lead rotates.

EXAMPLE 25

The lead of example 19, wherein said sensor is a magnetic sensor which senses external magnetic fields transmitted by a device positioned outside of the head.

EXAMPLE 26

The lead of example 19, wherein said sensor is a gravitational sensor configured to sense changes in gravitational field following rotation of said lead.

EXAMPLE 27

The lead of example 19, wherein said sensor comprises a radio-frequency sensitive receiver configured for receiving different wireless signals from at least two spaced apart transmitters positioned outside of the brain.

EXAMPLE 28

A brain navigation lead with an elongated body, comprising:
at least one electrode positioned on the outer surface of said lead;
a distal coupler fixed within the internal lumen of said lead;
wherein said distal coupler further comprising at least one channel and/or at least one opening sized and shaped to accurately direct said at least one electrode to a desired position on said outer surface of said lead during the manufacturing of the lead.

EXAMPLE 29

The lead of example 28, wherein said distal coupler comprises at least two channels shaped and sized to accurately direct at least two electrodes to at least two different positions with a desired angle on the circumference of said lead.

EXAMPLE 30

A brain navigation lead with an elongated body, comprising:
at least one electrode positioned on the outer surface of said lead;
at least one electrically conductive wire connected to said electrode and positioned within the internal lumen of said lead;
a flexible electro-magnetic shield made from conductive material positioned within said internal lumen at least partly between said conducting wires and an internal surface of said elongated body;

wherein said shield is shaped and sized to shield said conducting wires from external electro magnetic fields.

EXAMPLE 31

The lead of example 30, wherein said shield comprises a conductive braided shield or a coiled shield or a conductive mesh shield.

EXAMPLE 32

The lead of example 30, wherein said shield covers at least 70% of the length of said conductive wires.

EXAMPLE 33

The lead of example 32, wherein said shield covers at least 70% of the circumference of said conductive wires.

EXAMPLE 34

The lead of example 30, wherein said shield comprises at least one connector for connecting said shield to an amplifier.

EXAMPLE 35

The lead of example 30, wherein said shield comprises thin electrically conducting wires with a diameter smaller than 100 micron.

EXAMPLE 36

A brain navigation lead, comprising:
an elongated lead body having a distal section and a proximal section;
at least one electrode contact positioned on the outer surface of said lead;
at least one twisting sensor;
wherein said twisting sensor detects a relative twist of said distal section relative to said proximal section when said lead is inserted into the brain.

EXAMPLE 37

The lead of example 36, wherein said twisting sensor comprises a fiber optic twist sensor, positioned at least partly along the lead axis.

EXAMPLE 38

The lead of example 36, wherein said twisting sensor comprises at least one coiled wire and wherein said sensor detects changes in the resistance of said coiled wire when said lead twist.

EXAMPLE 39

The lead of example 36, further comprising at least one marker located at the proximal section of said lead in a position that remains visible to a user during a lead navigation process,
wherein said twisting sensor detects a relative twist of said distal section relative to said marker.

EXAMPLE 40

A system for aligning an electrode lead comprising:
a lead having at least one marker located in a visible region on the outer surface of said lead;
an external element shaped and sized to be connectable to said lead to prevent the rotation of said lead, wherein said external element comprising an alignment feature;
wherein said marker is shaped and sized to be aligned with said alignment feature before said external element is connected to said lead to prevent a rotation of said lead relative to said external element.

EXAMPLE 41

The system of example 40, wherein said external element is a cannula surrounding at least partly said lead, wherein said cannula comprising an opening sized and shaped to allow visualization of said marker of said lead through said opening.

EXAMPLE 42

The system of example 41, wherein said external element is a DBS-ruler.

EXAMPLE 43

A method for inferring at least one trajectory inside a brain tissue, comprising:
recording a plurality of signals from said brain tissue by electrodes positioned at different spatial locations inside the brain and along the insertion trajectory of a lead;
analyzing said signals by functionally mapping brain tissue surrounding said insertion trajectory;
inferring at least one additional trajectory or part of an additional trajectory at a distance from said insertion trajectory based on said functionally mapping.

EXAMPLE 44

The method of example 43, further comprising updating an insertion step size of said lead based on said functionally mapping of said brain tissue following said analyzing.

EXAMPLE 45

The method of example 43, wherein said recording comprising recording directional signals from sources located inside the brain in a distance of at least 0.2 mm from a measuring electrode on said lead.

EXAMPLE 46

The method of anyone of example 43 to 45, wherein said analyzing comprising separately analyzing each of said plurality of signals, and wherein said inferring comprising inferring a plurality of trajectories in a distance of at least 0.5 mm from said lead.

EXAMPLE 47

The method of anyone of example 43 to 45, wherein said analyzing comprising analyzing said plurality of signals in a single multi-channel model by a multi-channel algorithm, and wherein inferring comprising inferring a single trajectory based on the results of said multi-channel algorithm.

EXAMPLE 48

A method for updating a model of a functional brain tissue map, comprising:
providing a model of a functional brain tissue map, wherein said map comprises functionally tagged brain tissue regions;
electronically collecting functional-labeled brain tissue data from surgical procedures and/or imaging procedures; and
updating said model based on the collected functional-labeled brain tissue data.

EXAMPLE 49

The method of example 48, wherein said updating comprising updating said model based on rules or a table of rules.

EXAMPLE 50

The method of example 48 or 49, comprising using said updated model in an online mapping procedure during a surgery.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system".

Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a general flow chart of a lead implantation process, according to some embodiments of the invention;

FIG. 2 is a block diagram describing main lead components and attached devices, according to some embodiments of the invention;

FIG. 3A is a detailed flow chart of the navigation and electric field application process, according to some embodiments of the invention;

FIGS. 3B-3C are schematic views of a system for brain navigation implantation, recording and electric field application, according to some embodiments of the invention;

FIG. 3D is a schematic view of a lead inserted into a brain, connected to a recording system, according to some embodiments of the invention;

FIG. 3E is a schematic view of a lead inserted into a brain, connected to an IPG, according to some embodiments of the invention;

FIG. 3F is a schematic view of a lead with an orientation marker, according to some embodiments of the invention;

FIGS. 3G-3H are schematic views of a DBS-ruler with an external alignment element, according to some embodiments of the invention;

FIGS. 3I-3J are schematic views of a lead and a lead holder inserted into a DBS-ruler, according to some embodiments of the invention;

FIG. 3K is a schematic view of a lead with a marker positioned within a guiding cannula, according to some embodiments of the invention;

FIGS. 3L and 3M are schematic views of an electrode holder and a lead inside the lead holder, according to some embodiments of the invention;

Figure 3A:
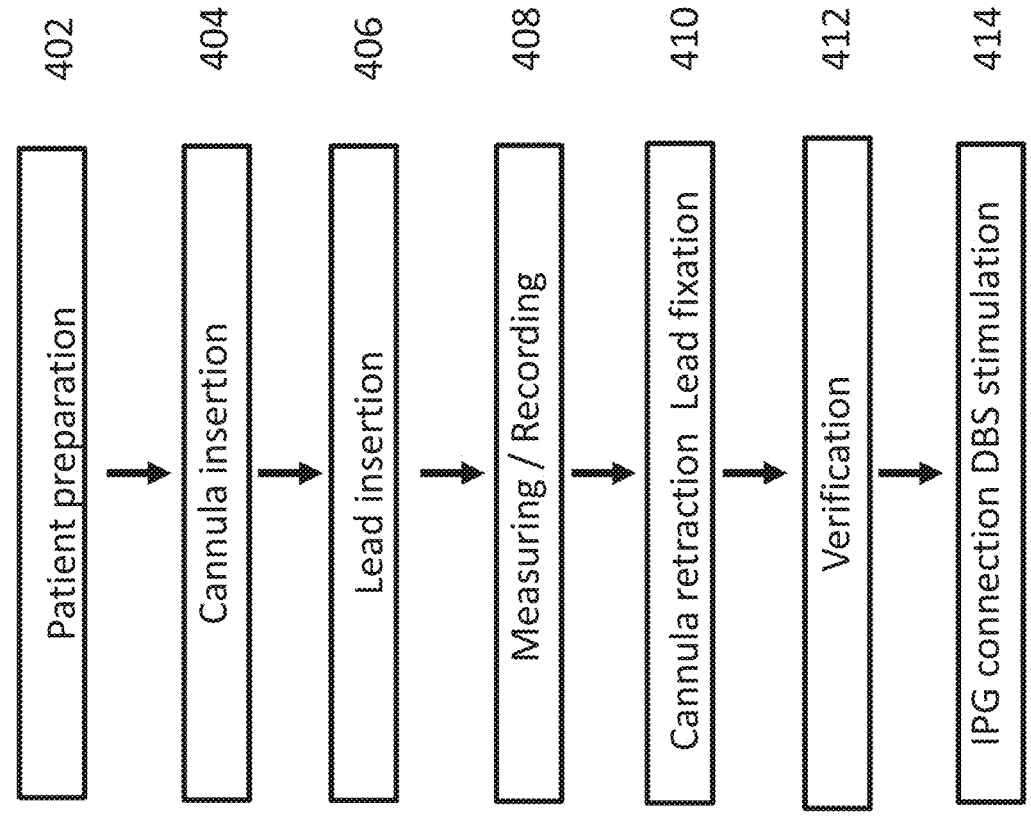
Figure 3D:
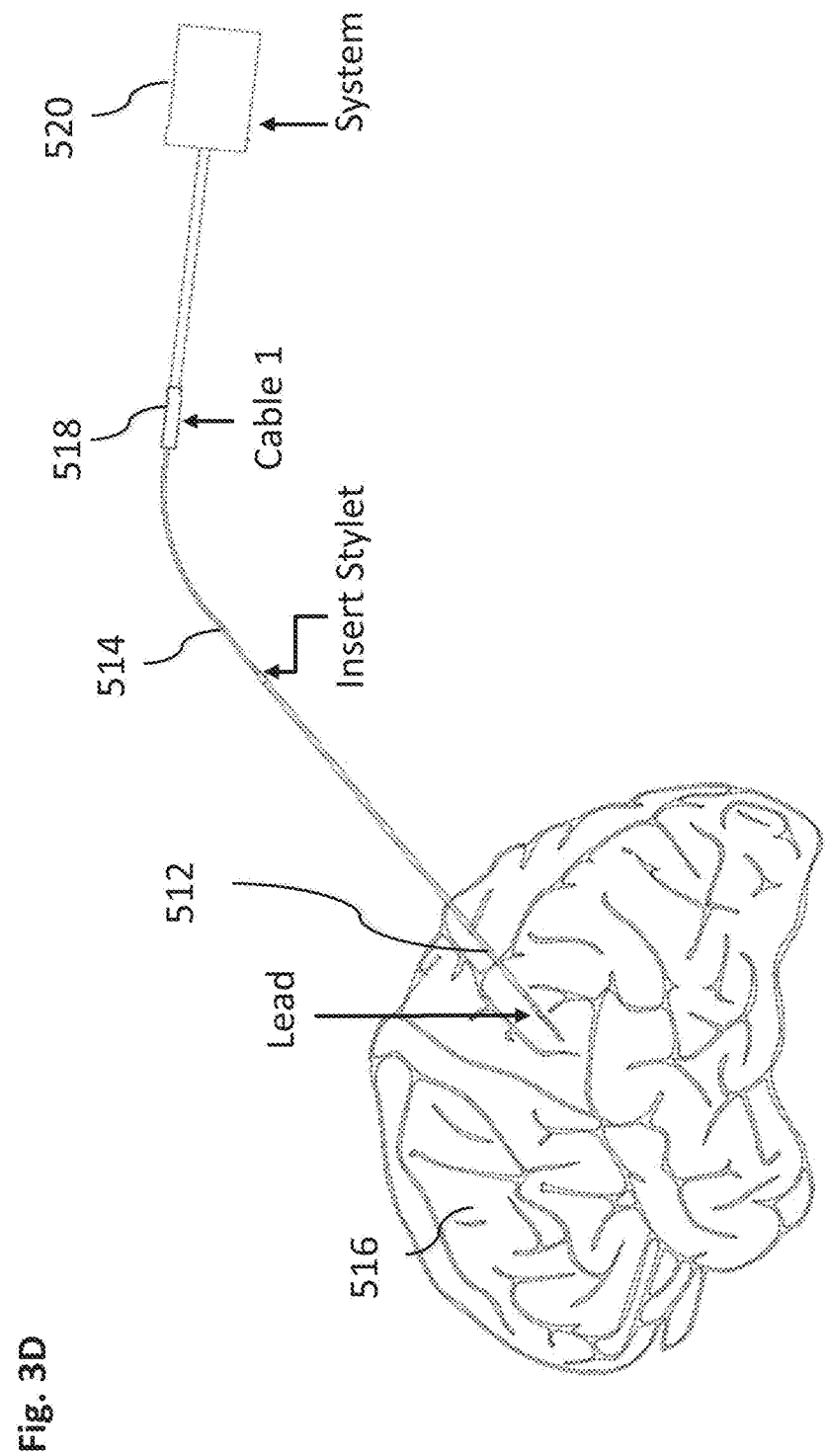
Figure 3F:
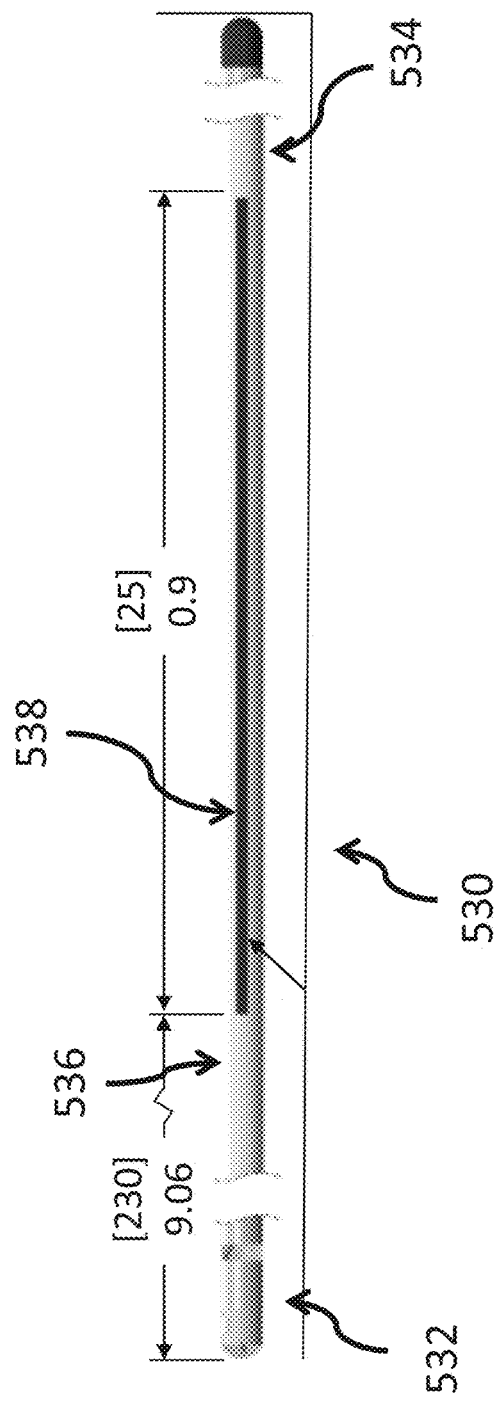
Figure 3H:
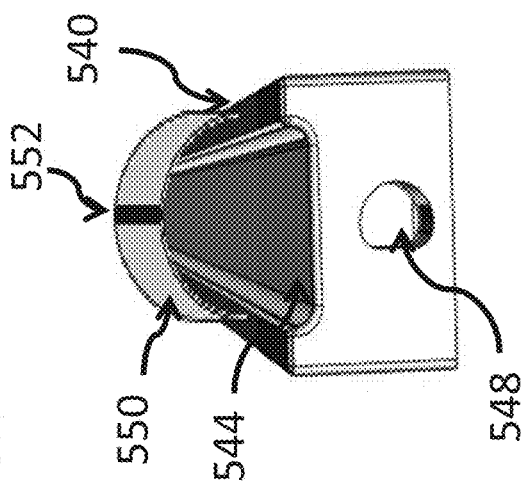
Figure 3G:
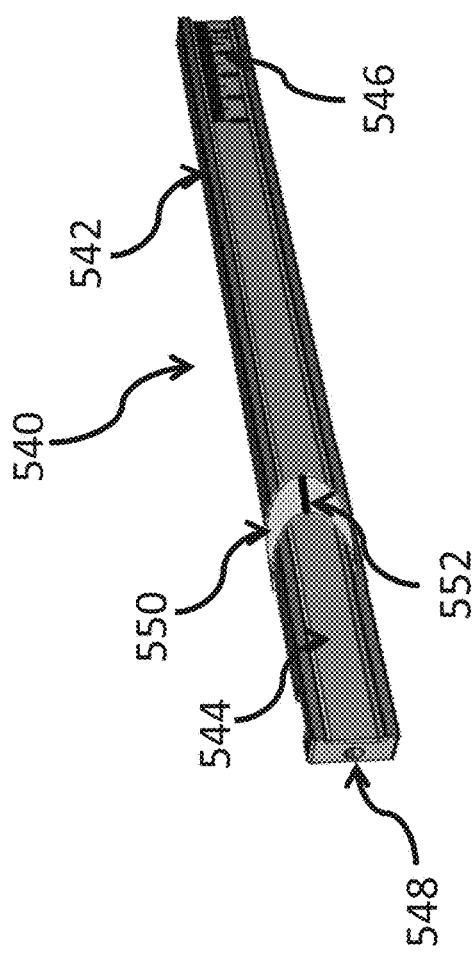
Figure 3K:
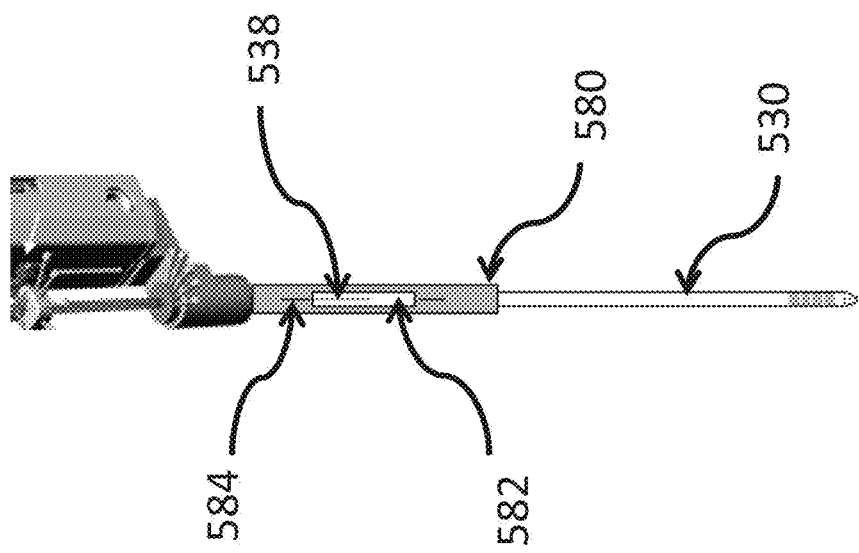
Figure 3M:
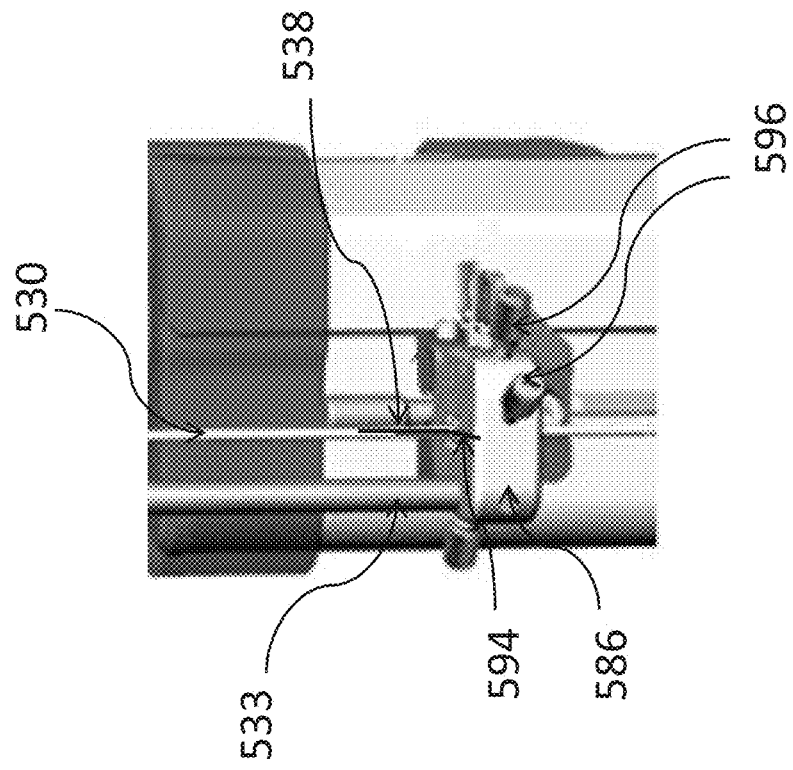
Figure 3L:
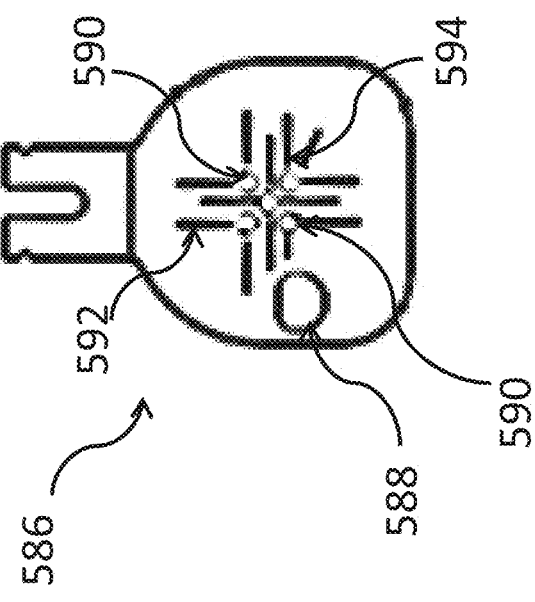
Figure 3N:
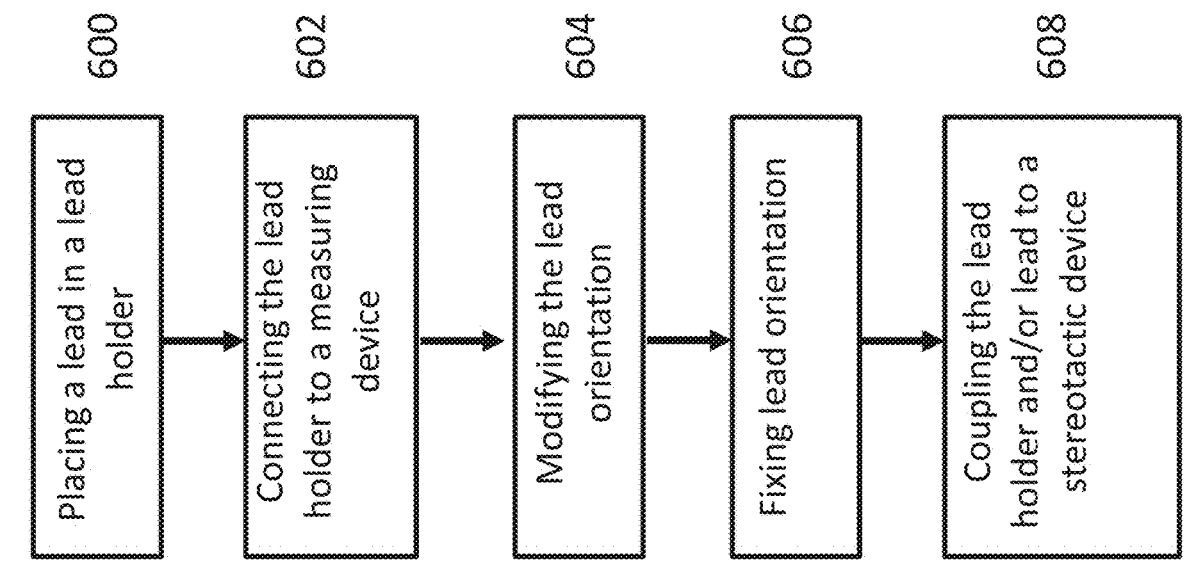
Figure 5C:
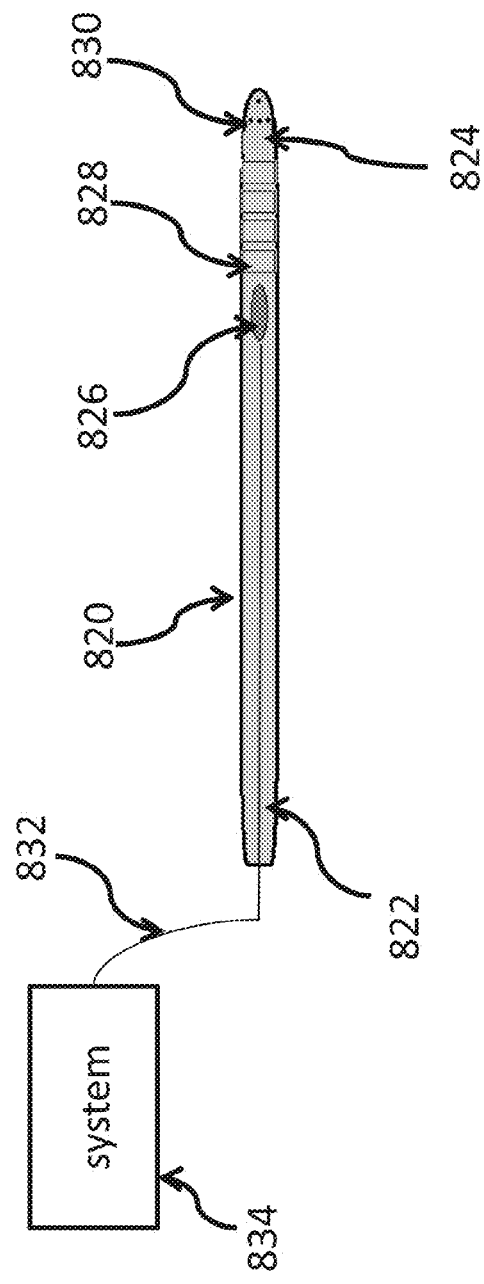
Figure 5D:
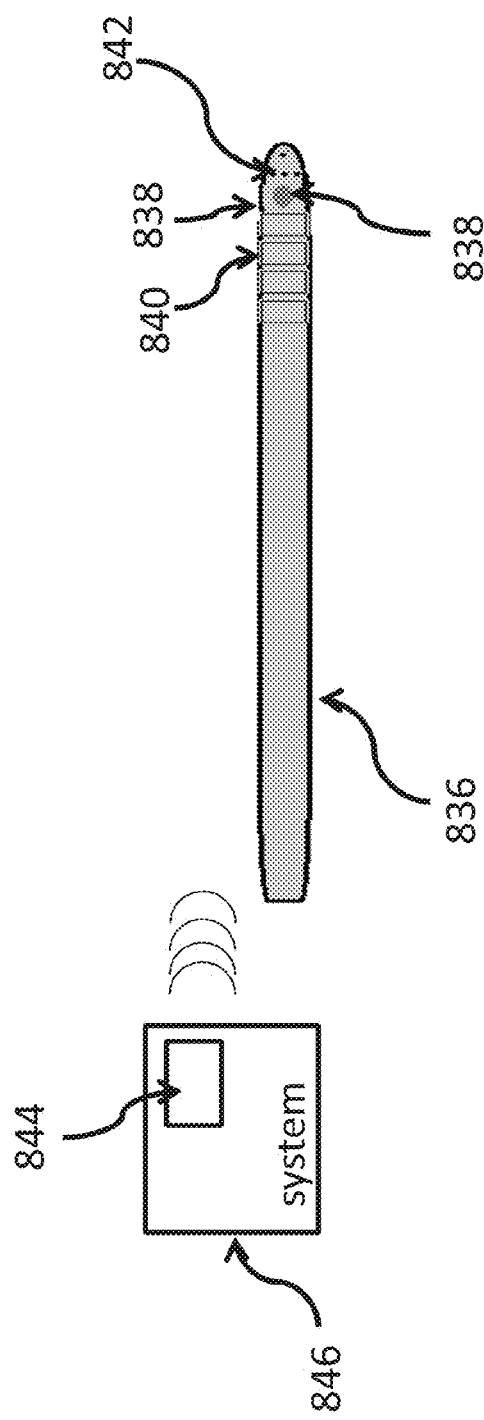
Figure 5E:
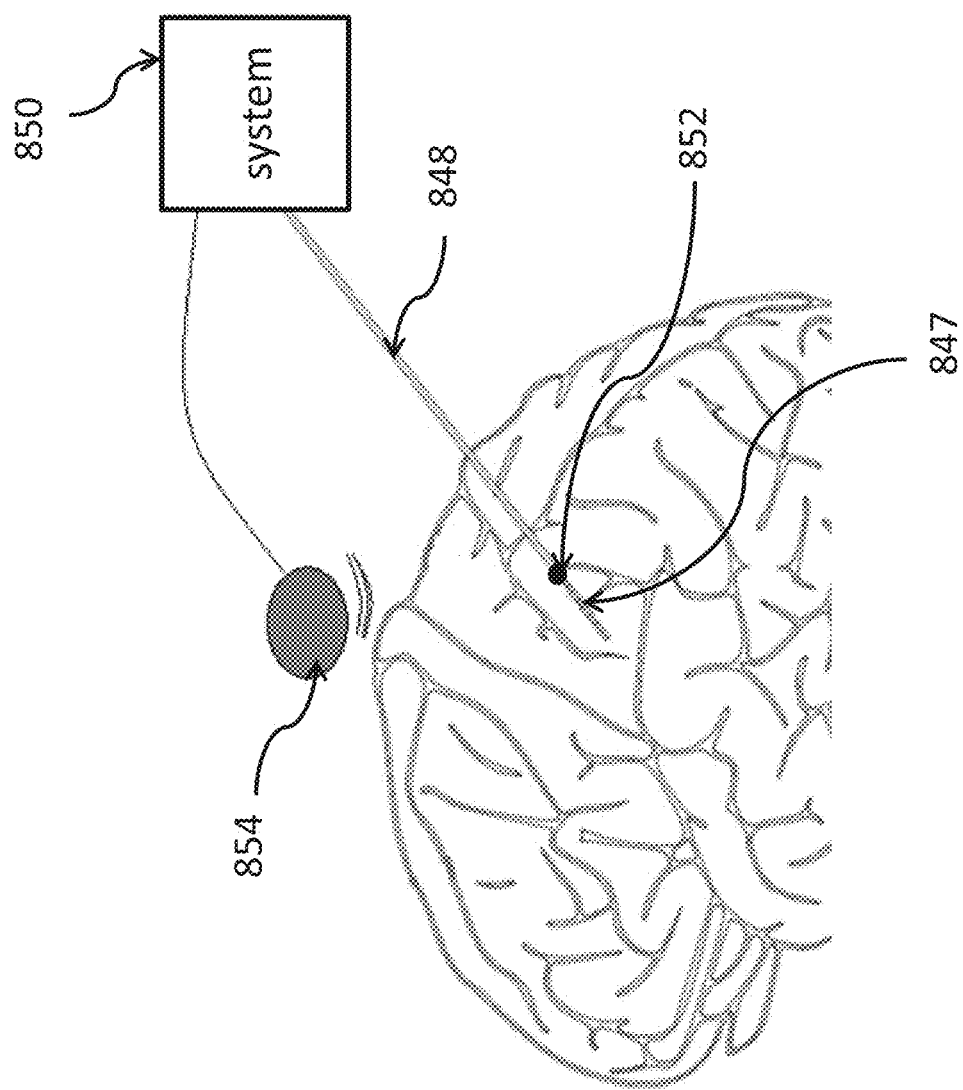
Figure 6:
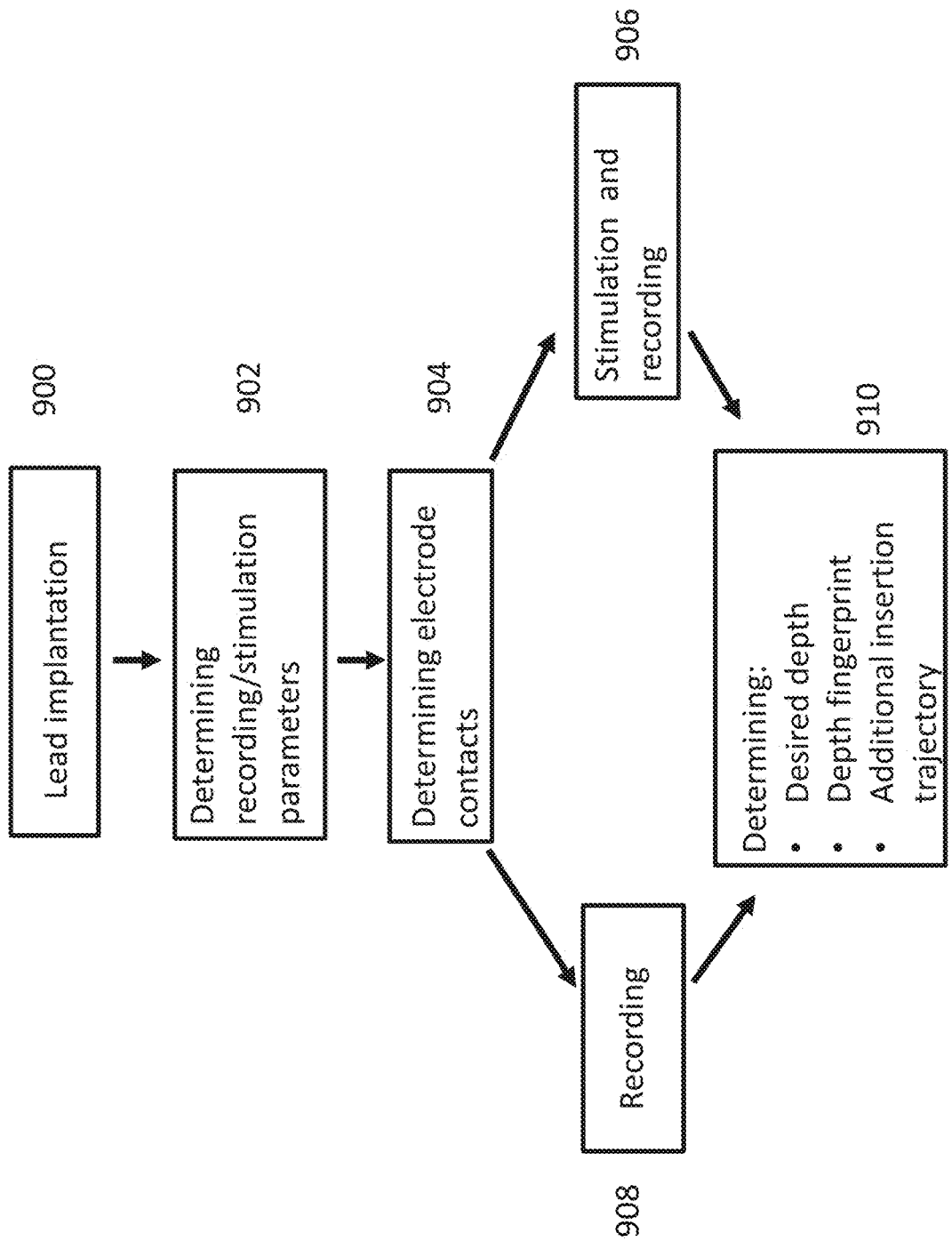
Figure 8:
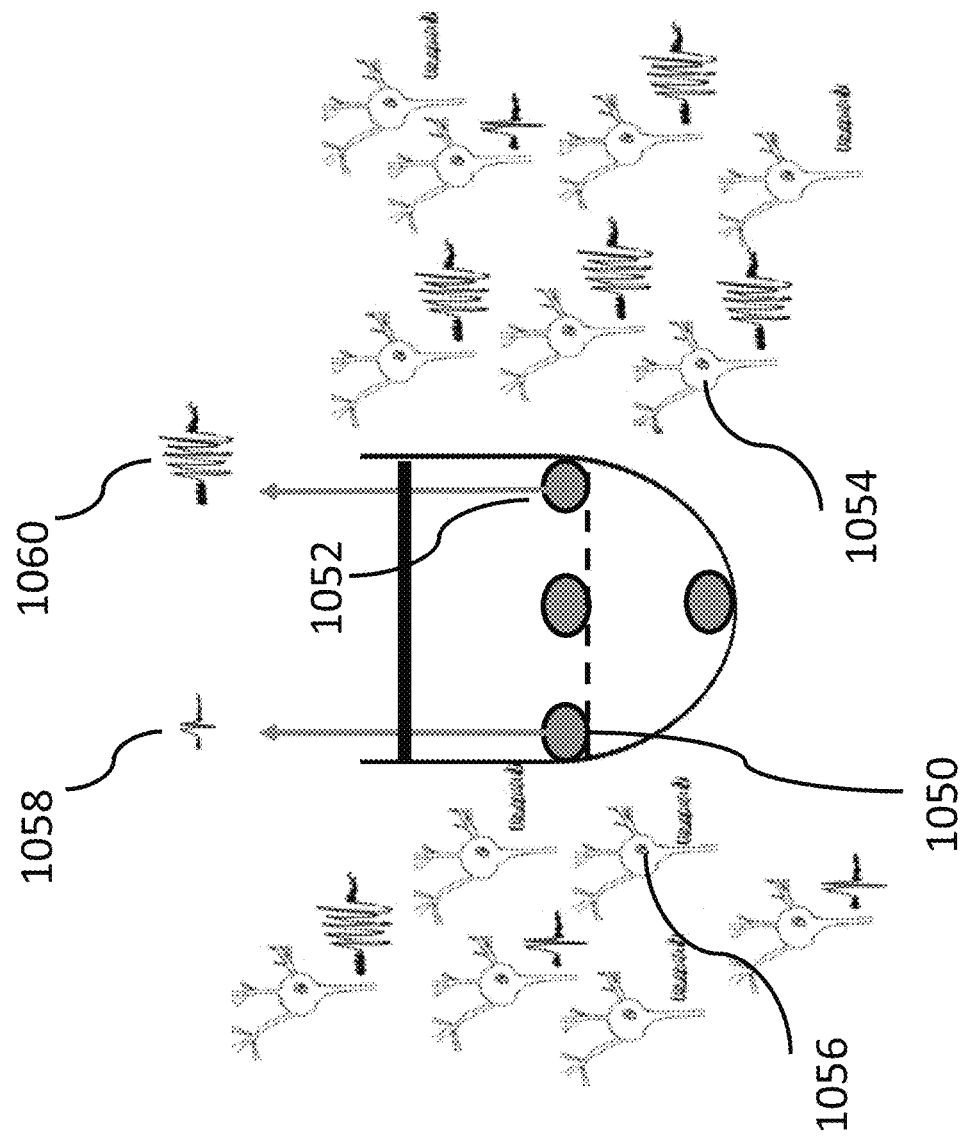
Figure 9A:
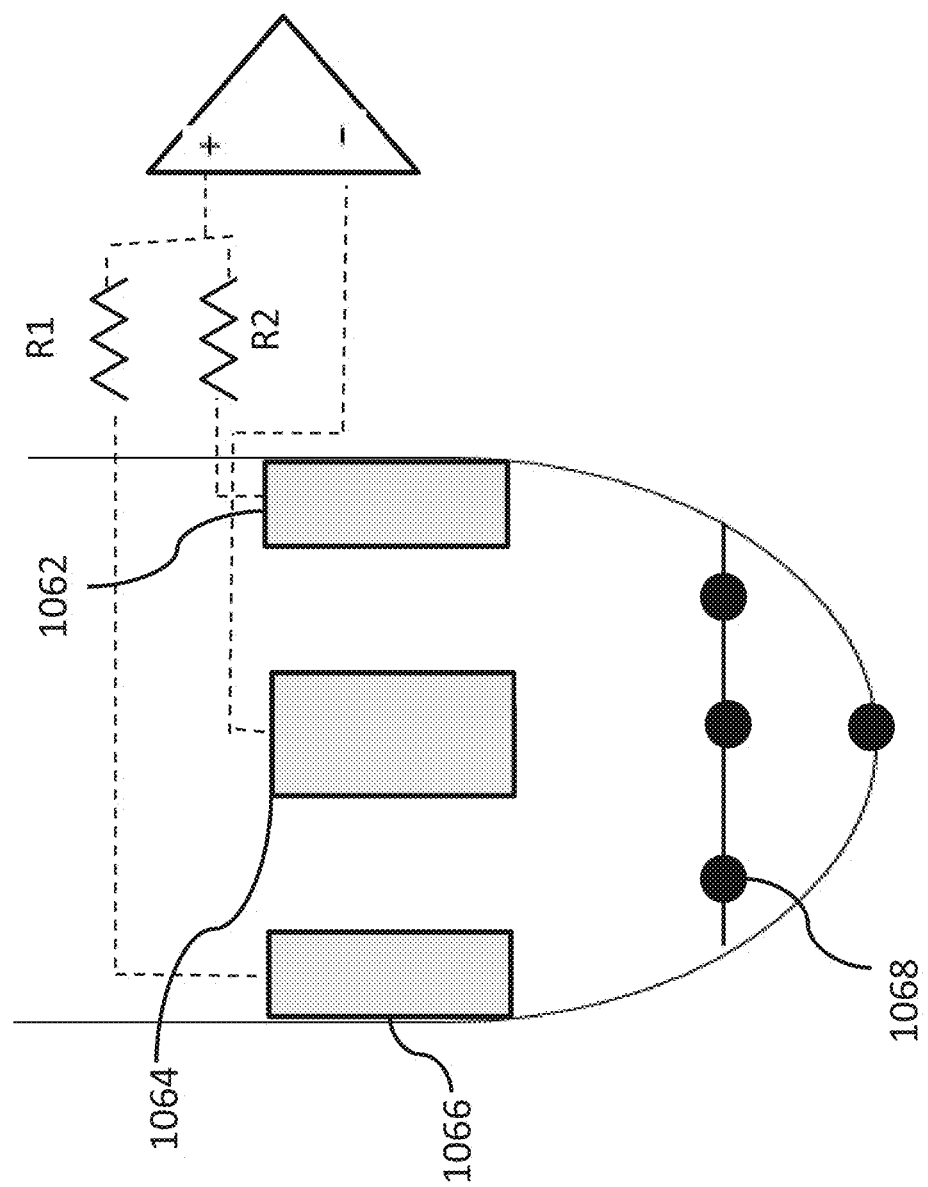
Figure 9B:
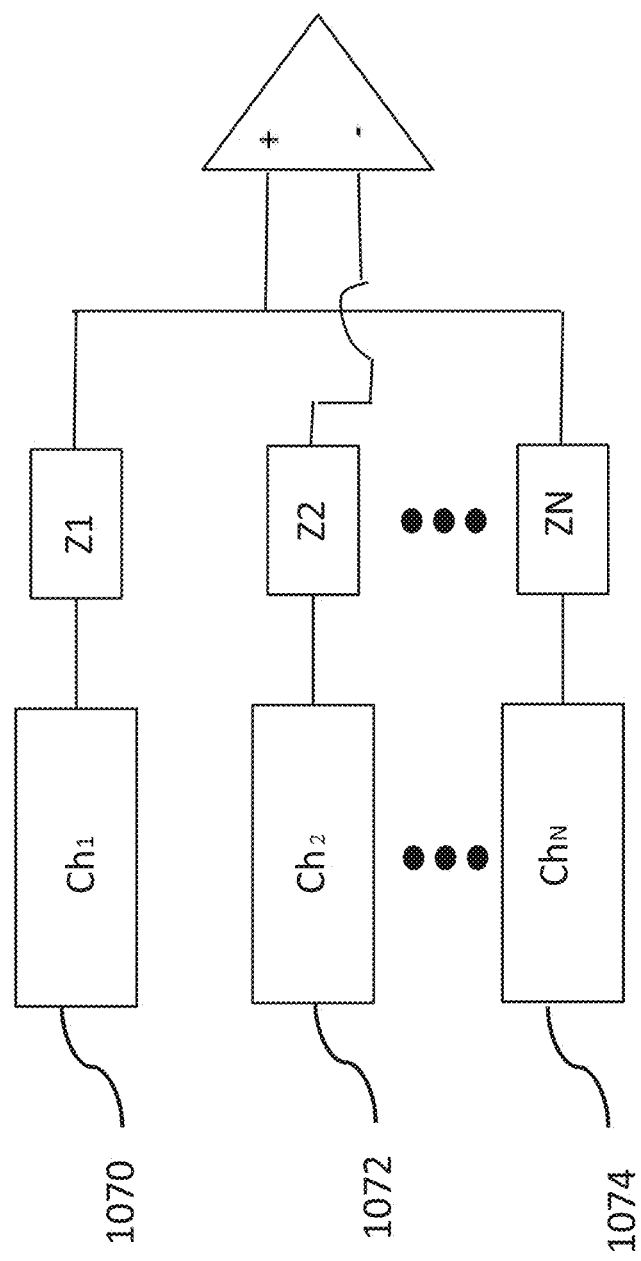
Figure 10:
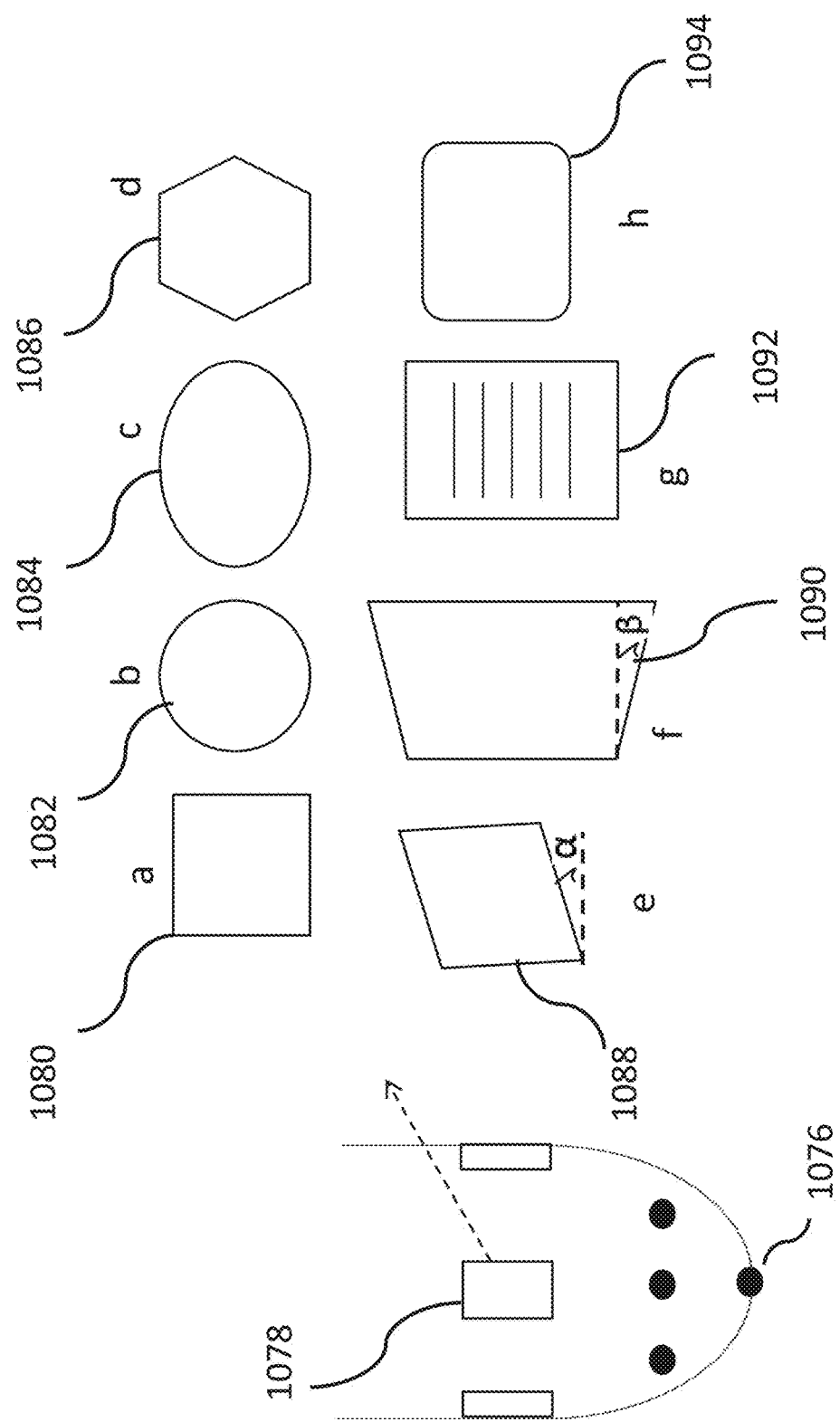
Figure 12A:
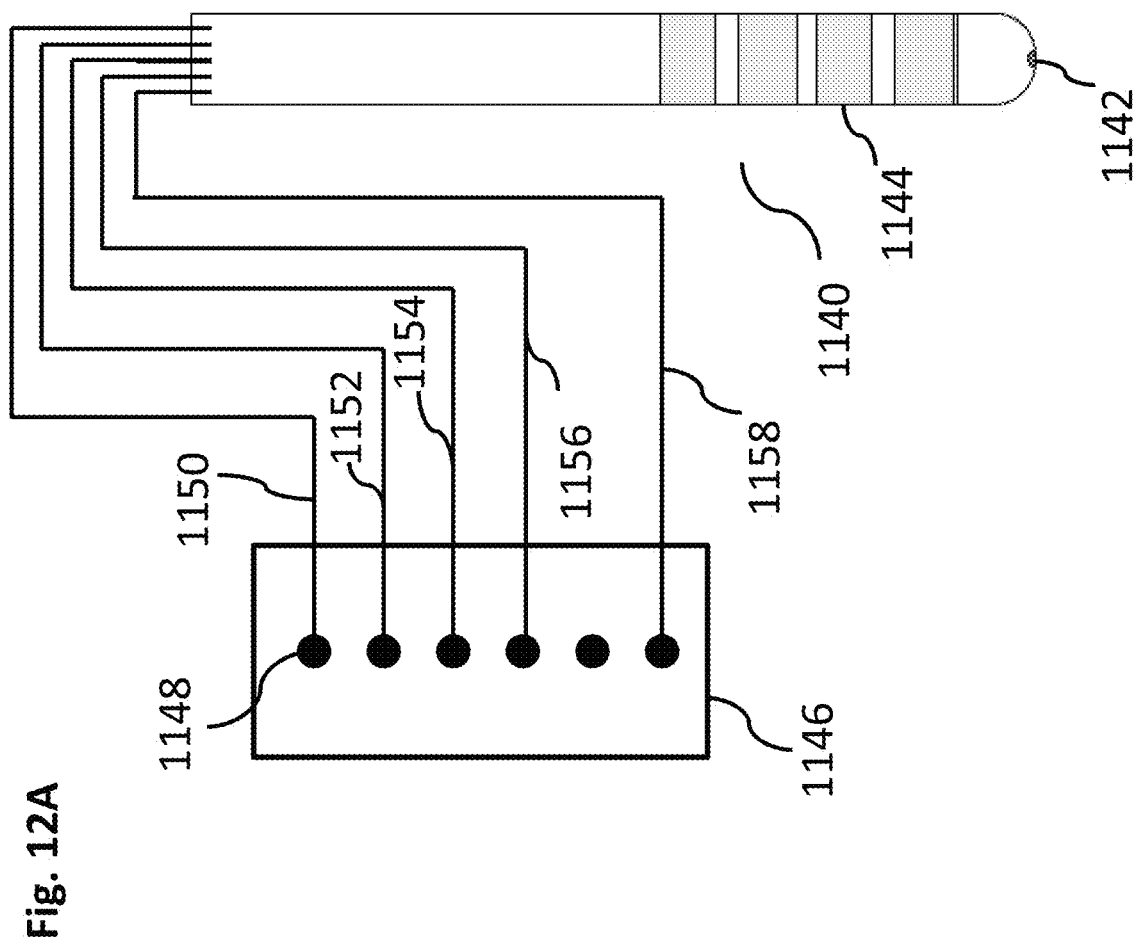
Figure 12B:
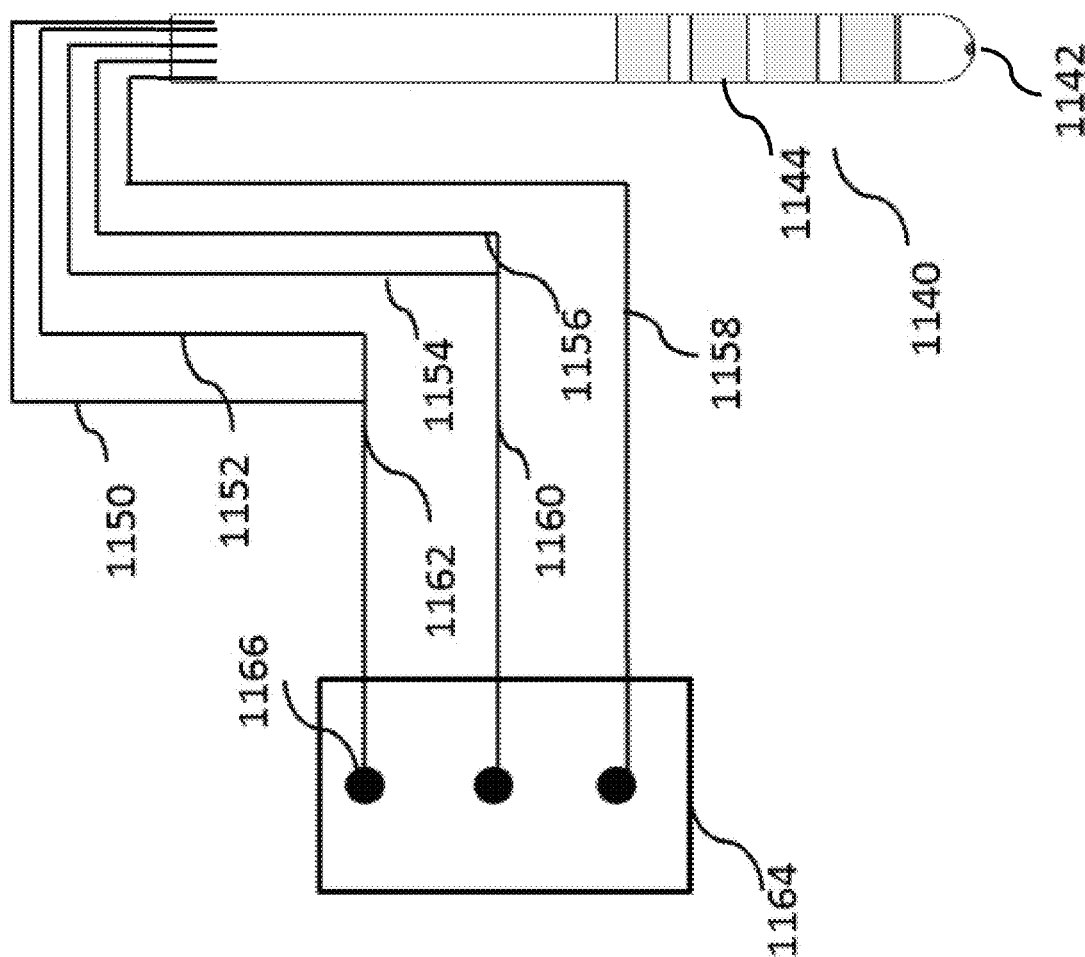
Figure 13B:
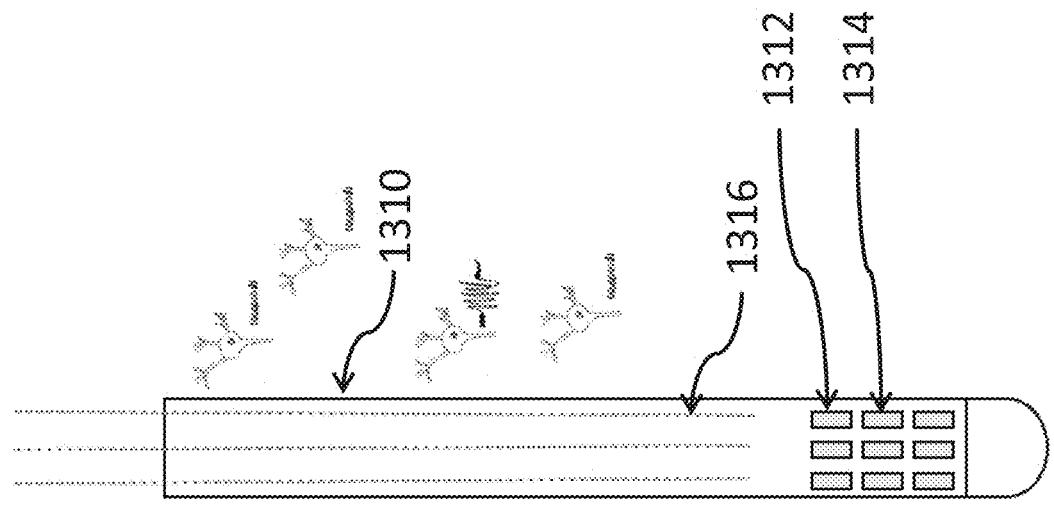
Figure 13A:
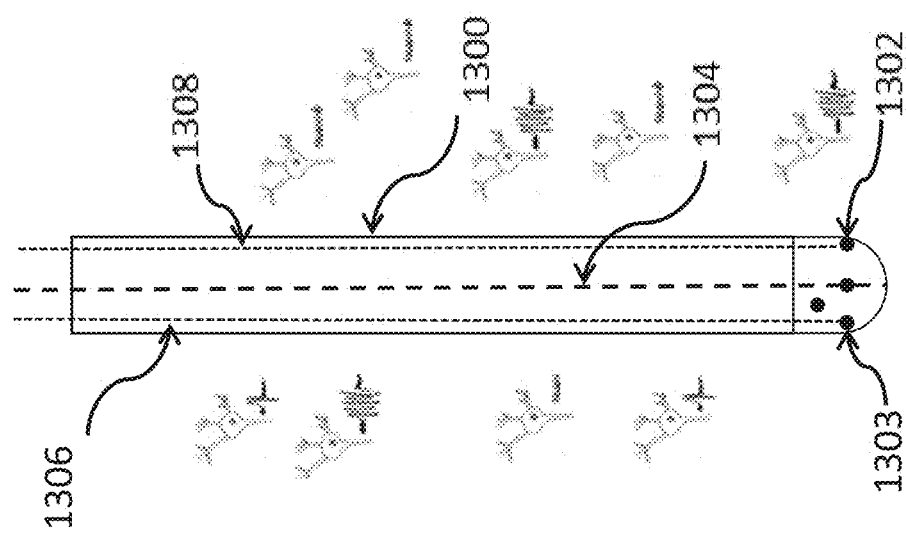
Figure 13E:
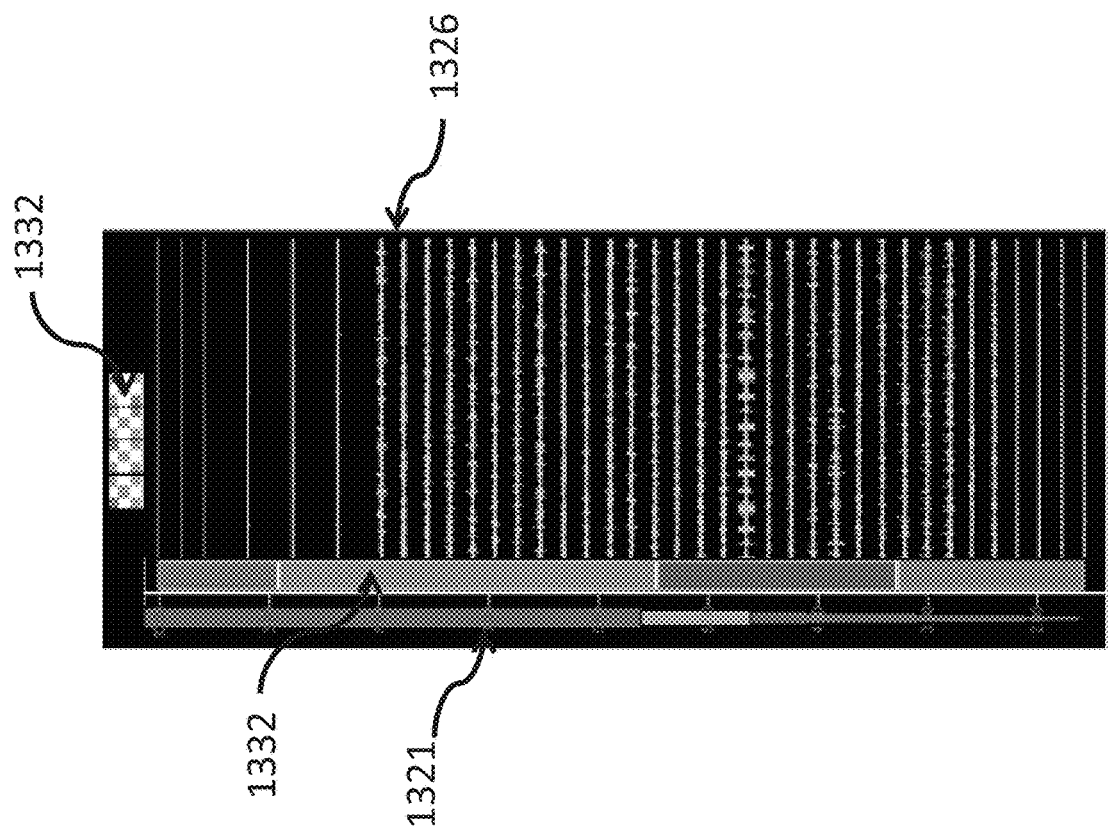
Figure 14A:
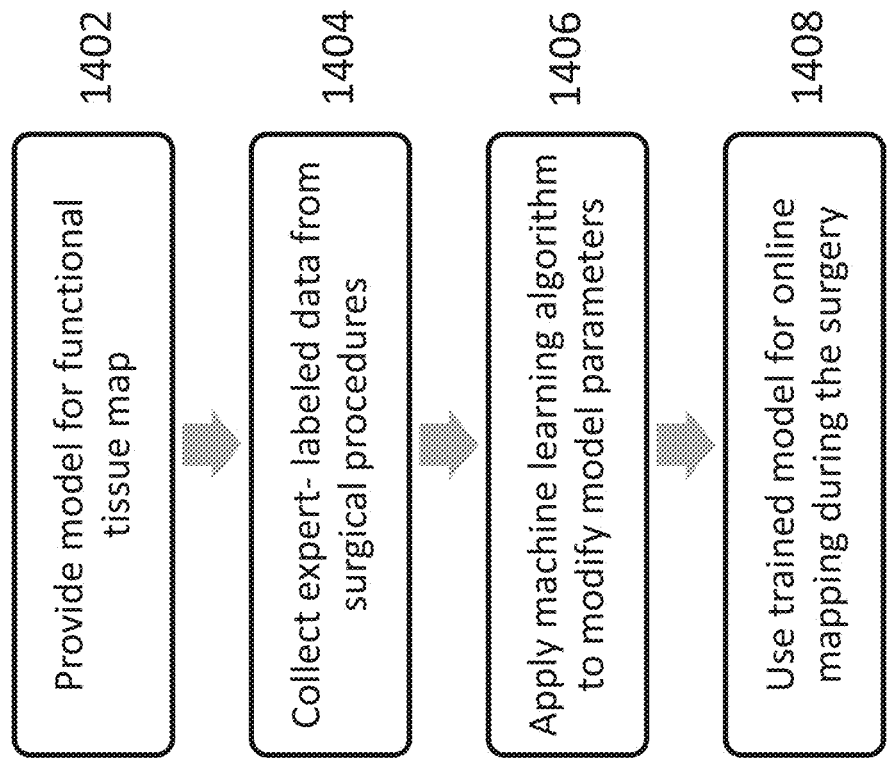
Figure 14B:
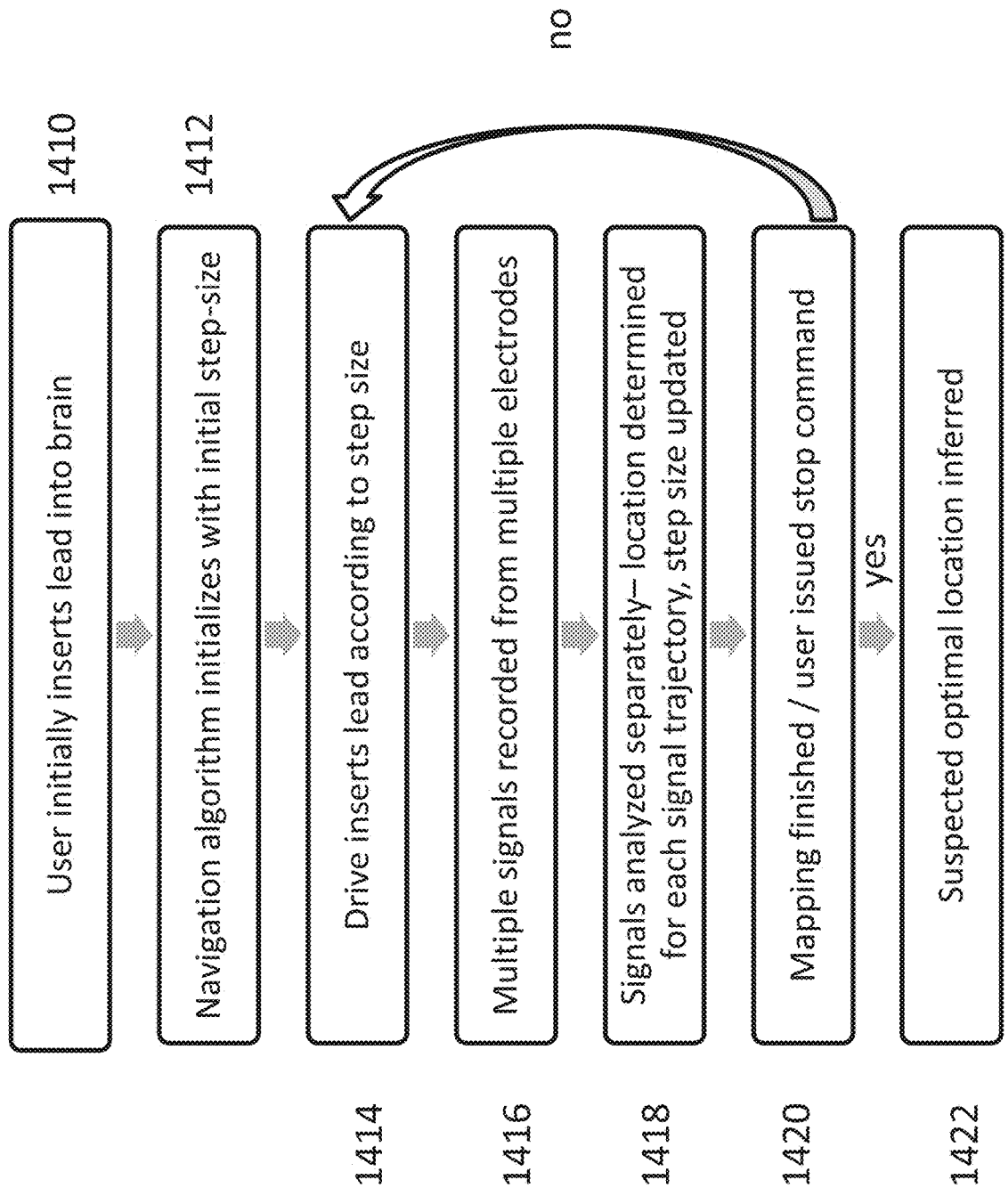
Figure 14C:
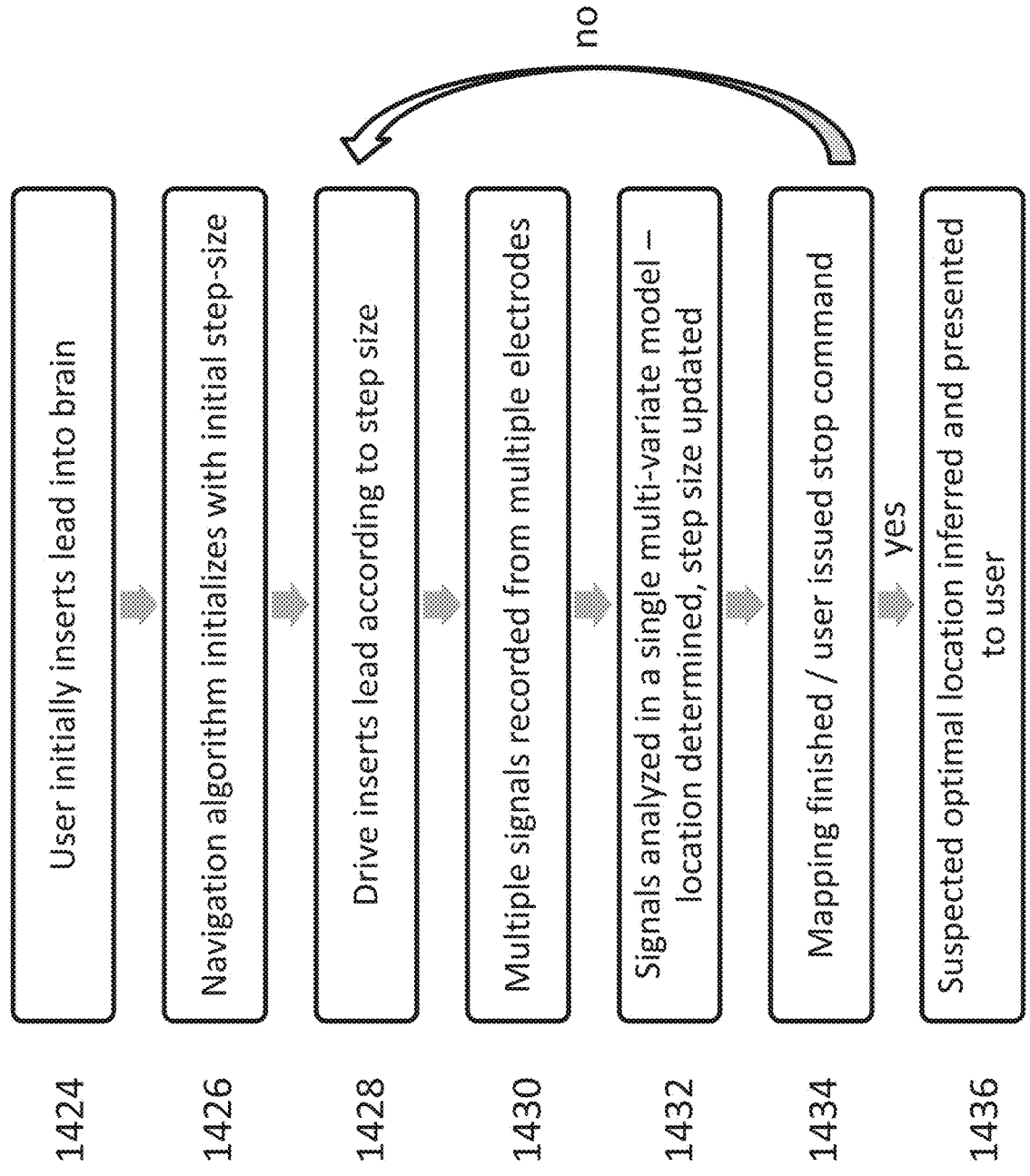
Figure 15:
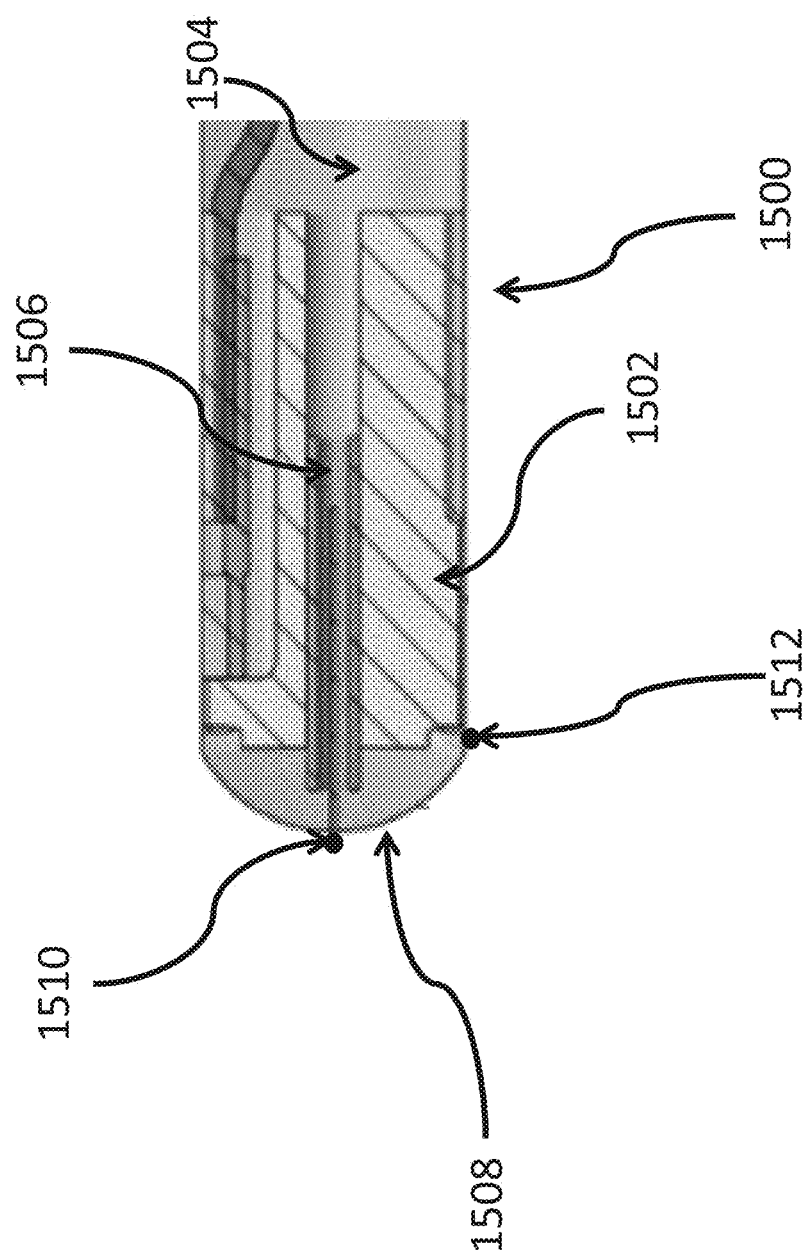
Figure 16A:
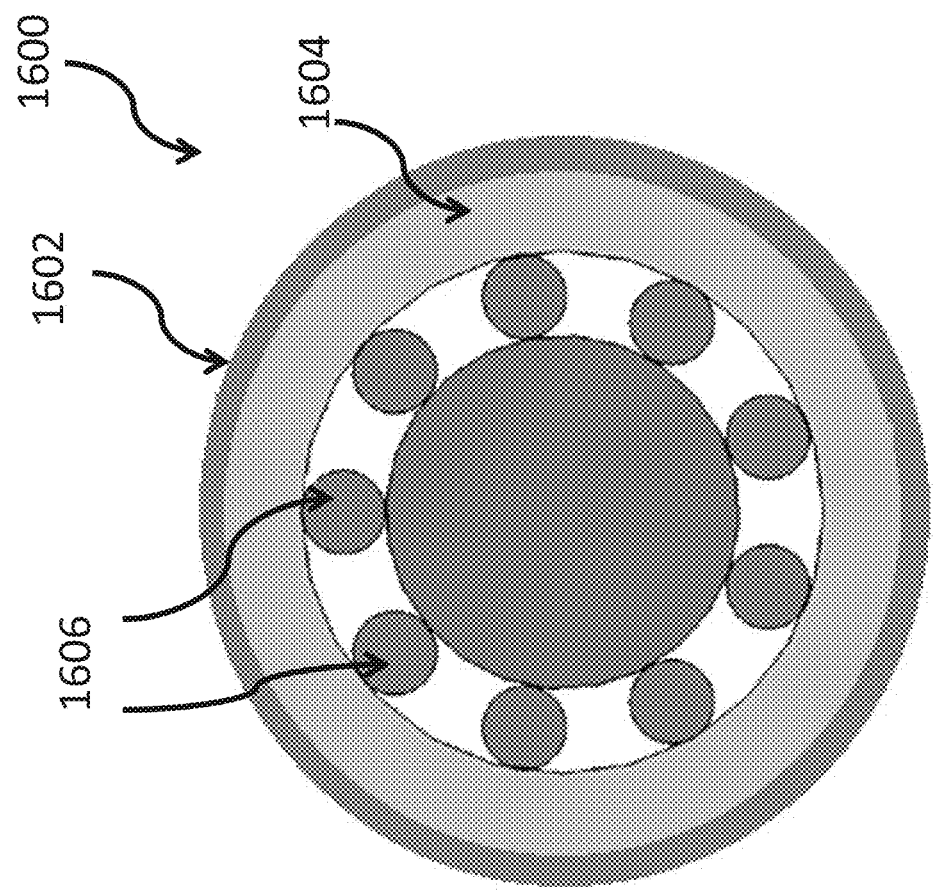

FIG. 3N is a flow chart describing a process for aligning a lead, according to some embodiments of the invention;

FIGS. 4A-4J are schematic views of brain navigation lead embodiments, according to some embodiments of the invention;

FIG. 5A is a schematic illustration of a brain navigation lead embodiment, according to some embodiments of the invention;

FIG. 5B is a block diagram of a lead with an orientation element, according to some embodiments of the invention;

FIGS. 5C and 5D are schematic views of a lead with an orientation sensor, according to some embodiments of the invention;

FIG. 5E is a schematic view of a lead with an orientation sensor inside the brain, according to some embodiments of the invention;

FIG. 6 is a detailed flow chart describing the process of recording and electric field application, according to some embodiments of the invention;

FIGS. 7A-7G are schematic views of electrode contact combinations for electric field application, according to some embodiments of the invention;

FIG. 8 is a schematic view of a directional recording process, according to some embodiments of the invention;

FIGS. 9A-9B are schematic views showing multi-polar recording, according to some embodiments of the invention;

FIG. 10 is a schematic view of macro-electrode contacts, according to some embodiments of the invention;

FIGS. 11A-11G are schematic views showing electric fields generated by electrode contacts, according to some embodiments of the invention;

FIGS. 12A-12B are schematic views showing inter-connecting lead wires, according to some embodiments of the invention;

FIGS. 13A and 13B are schematic views of lead electrodes which generate multiple spatially differentiated recording trajectories from the lead's single insertion trajectory, according to some embodiments of the invention;

FIG. 13C is a schematic view of a functionally mapped trajectory, according to some embodiments of the invention;

FIG. 13D is a schematic view showing the generation of multiple spatially differentiated mapping results from multiple signal recordings, according to some embodiments of the invention;

FIG. 13E is a schematic view showing the generation of a single trajectory from multiple signals recordings, according to some embodiments of the invention;

FIGS. 14A-14C are flow charts of processes for generating a single or more trajectories from multiple signal recordings, according to some embodiments of the invention;

FIG. 15 is a schematic cross-section of a distal coupler, according to some embodiments of the invention;

FIG. 16A is a schematic upper-view cross section of a lead with an internal electro-magnetic shield, according to some embodiments of the invention; and FIG. 16B is a schematic side-view cross section of a lead with an internal electro-magnetic shield, according to some embodiments of the invention.

DESCRIPTION OF SPECIFIC EMBODIMENTS OF THE INVENTION

The present invention, in some embodiments thereof, relates to a brain navigation lead and, more particularly, but not exclusively, to brain navigation lead comprising electrode contacts and configured to measure electrical activity of brain tissue.

An aspect of some embodiments relates to a brain navigation lead for electrical activity mapping and delivery of an electric field, having at least one micro-electrode contact located at the distal end of the lead, and at least one macro-electrode contact located at a more proximal location on the lead relative to the at least one microelectrode. In some embodiments, the electrode is positioned along the lead body. In some embodiments, the brain navigation lead comprises at least one micro-electrode contact located at the lead tip and at least three macro-electrode contacts distributed along the lead circumference and located at a more proximal location on the lead relative to the micro-electrode contact. Optionally, brain navigation lead comprises at least three micro-electrode contacts distributed along the lead circumference at the distal end of the lead, and at least three macro-electrode contacts distributed along the lead circumference, in a more proximal location on the lead relative to the micro-electrode contacts.

In some embodiments, lead comprises a micro-electrode contact in its distal tip, at least one additional micro-electrode contact proximally to the distal tip contact, and at least one macro-electrode contact positioned proximally to the at least one additional micro-electrode contact. In some embodiments, macro-electrode contacts are positioned proximally to micro-electrode contacts.

In some embodiments, micro-electrode contacts are configured to sense electrical activity of brain tissue and macro-electrode contacts are configured to apply an electrical field to brain tissue. Alternatively, micro-electrode contacts and/or macro-electrode contacts are configured to apply an electric field to brain tissue.

Optionally, microelectrode contacts and/or macro-electrode contacts are configured to sense electrical activity of brain tissue.

In some embodiments, the lead is configured to be connected to an external recording device and to an implanted pattern generator (IPG). This allows using the same lead for both navigating into a desired target location, and for applying an electric field to a brain tissue, for example for deep brain stimulation (DBS). Therefore, there is no need to replace the navigation lead with a different stimulation lead, which often prolongs the implantation procedure, and may reduce the DBS treatment efficacy, due to accumulation of errors in the replacement process.

Alternatively, the lead is configured to be connected to an IPG for both navigation and therapeutic electric field application, for example electric field application for deep brain stimulation.

In some embodiments, micro-electrode contacts and/or macro-electrode contacts distributed along the lead circumference are configured to sense electrical activity of brain tissue from different directions around the lead. Optionally, micro-electrode contacts and/or macro-electrode contacts distributed along the lead circumference are configured to apply an electric field to brain tissue in different directions.

An aspect of some embodiments relates to a brain navigation lead configured to be connected to an IPG that has fewer channel outputs than lead contacts, by short circuiting at least two lead contacts and connecting the short circuited contacts to a single IPG channel output. For example, short-circuiting is required when connecting a lead with 8 macro-contacts to an IPG with 4 channels. In some embodiments, if a brain navigation lead contains 2 ring macro-contacts and 2 segmented rings of 3 contacts each, e.g. in a 1-3-3-1 configuration, or any permutation, then the 3 segments may be short-circuited to connect to a single IPG output, and the lead may then be substantially equivalent to a 4-rings (1-1-1-1) lead. In some embodiments, by short-circuiting electrode contacts, it is possible to apply a similar electric field through the combined electrode contacts to a larger area of brain tissue.

An aspect of some embodiments relates to a method for navigating a lead to a desired depth, by mapping brain tissue electrical activity using at least one electrode contact located at the distal end of the lead, determining a desired depth for electric field application and positioning at least one electrode contact at the desired depth. In some embodiments, the electrode contact used for electric field application is located at a more proximal location on the lead, relative to the mapping electrode contact which is located at the distal end of the lead.

In some embodiments, at least one microelectrode contact and/or at least one macro-electrode contact located on the lead are used for electrical activity mapping for determining a desired depth for electric field application. In some embodiments, a desired depth for electric field application is determined based on electrical activity measured by the lead and on parameters measured by at least one other sensor and/or as part of an analysis, for example an EEG analysis.

In some embodiments, electrode contacts distributed along the circumference of the lead are configured to map brain tissue electrical activity by sensing and recording electrical activity from different directions around the lead. In some embodiments, this electrical mapped activity is used to generate a depth signature, while the lead moves into the brain tissue. In some embodiments, the depth signature is generated based on at least one electric field applied to the brain tissue. In some embodiments, the electric field is applied through at least one micro-electrode contact and/or at least one macro-electrode contact. In some embodiments, the depth signature of a desired electric field application target is used to confirm that an electrode is placed at the desired target area, prior to an electric field application using an implanted pattern generator (IPG).

In some embodiments, electric field application followed by mapping of the tissue electrical activity is used to determine the IPG electric field application parameters. In some embodiments these parameters include for example, which electrode contacts to use, pulse-width, pulse repetition frequency (PRF), and pulse amplitude. In some embodiments, electrical activity mapping by electrode contacts on the lead includes indirectly evaluating a neural correlate of muscle rigidity and severity of tremor before and during electric field application. Alternatively, evaluating a neural correlate of muscle rigidity and severity of tremor before and during electric field application is performed by other sensors.

In some embodiments, directed electrical activity recording and electric field application is used to predict at least one desired insertion trajectory for insertion of additional electrode leads. In some embodiments, directed electrical activity recording and electric field application is used to predict at least one desired insertion trajectory for positioning an electrode-contact in a desired location.

In some embodiments, recording while applying an electric field allows evaluating the effect of applied electric field on the tissue during lead navigation.

In some embodiments, recording while applying an electric field allows evaluating the effect of applied electric field on the tissue to determine desired depth and/or electric field application parameters for a second electric field application, for example by an IPG device.

An aspect of some embodiments relates to determining the twist of the lead and/or the spatial orientation of at least one electrode on the lead by non-imaging techniques. In some embodiments, the spatial orientation is determined using at least one orientation element positioned on said lead. In some embodiments, the at least one orientation element delivers an indication regarding to the spatial orientation of at least one microelectrode and/or at least one macro electrode positioned on the distal end of said lead, relative to the tissue surrounding said lead. Alternatively or additionally, the orientation element delivers an indication regarding to the relative spatial orientation between the at least one microelectrode and the at least one macro electrode. Optionally, the orientation element delivers an indication regarding to the orientation of at least one microelectrode and/or at least one macro electrode relative to a reference point on said lead and/or relative to an external reference point.

According to some embodiments, by visualizing and/or sensing the orientation element an indication is provided regarding the rotation of the lead. Alternatively or additionally, visualization and/or sensing of the orientation element provides an indication regarding the rotation of an electrode or electrode wiring. In some embodiments, the indication is a numerical indication which for example, indicates the rotation angle of the lead and/or one of the electrodes. Alternatively, the indication indicates any change from a desired orientation.

According to some embodiments, the orientation element comprises at least one marker positioned on a section of said lead which is located outside of said brain. Optionally the marker is positioned on the proximal end of the lead. In some embodiments, the marker is shaped and sized to provide a visual indication to a user regarding the spatial orientation of at least one electrode of the lead positioned inside the brain. Alternatively or additionally, the marker position is measured by a device. In some embodiments, the indication delivered by the marker is measured by an external sensor or by an external machine. In some embodiments, the marker provides an indication regarding the rotation or twisting of the lead and/or electrodes and/or electrode wires.

According to some embodiments, the orientation element for example the marker is aligned according to an alignment marker positioned on an external element connected to the lead, for example a lead holder or a DBS-ruler. In some embodiments, once the marker is aligned the lead position is fixed relative to the external element, for example to prevent relative rotation of the lead. Alternatively, the marker is aligned according to an alignment marker positioned on an external element which is proximal to the lead, for example an alignment marker positioned on a cannula surrounding the lead.

In some embodiments, the marker is aligned according to instructions of a software, for example an alignment software. In some embodiments, the software provides instructions regarding a desired orientation of the marker, for example a desired orientation that leads to a desired measuring or treatment by electrodes positioned on the lead. Alternatively, a user enters a desired electrode coordinates and/or a desired orientation of the lead to the software. Optionally, the software provides instructions to the user how to modify the orientation of the marker in order to reach the desired electrode coordinates.

According to some embodiments, the orientation element comprises an orientation or twisting sensor positioned on the lead. In some embodiments the sensor detects the twisting of the lead or at least part of the lead, for example the distal section of the lead. In some embodiments, the sensor detects the twisting of the distal section relative to the surrounding tissue or an external reference point. Alternatively or additionally, the sensor detects the twisting of the distal section of the lead relative to the proximal section, optionally relative to a marker positioned on the proximal section of the lead. In some embodiments, the sensor is electrically connected to an orientation detection circuitry and/or a control circuitry of the lead via electrical wiring. Alternatively, the orientation sensor is connected to the control circuitry via wireless communication, for example Bluetooth, wifi, or infra-red communication.

In some embodiments, the baseline orientation of the sensor is calibrated before the insertion of the lead relative to at least one electrode on the lead. Alternatively, or additionally, the baseline orientation of the sensor is calibrated relative to an external reference point, for example relative to an external element connected to the lead. Optionally, the external reference point is an external element positioned in a close distance, for example up to 10 cm from the lead, for example a cannula inserted into the brain near the lead or surrounding the lead.

In some embodiments, the orientation and/or the twisting of the lead and/or the orientation of the lead electrodes is determined based on changes in the electrical properties of the sensor, for example changes in the resistance of the sensor. In some embodiments, the sensor comprises at least one electrically conductive wire coiled inside the lead body, optionally inside the lead lumen. In some embodiments, when the lead rotates in the same direction as the coiled wire direction, the coiled wire is stretched and the electrical resistance increases. Alternatively, when the lead rotates in an opposite direction to the coiled wire direction, the coiled wire tension is reduced and the electric resistance of the wire decreases.

In some embodiments, the sensor comprises two electrically conductive wires, where each of the wires is coiled in an opposite direction. In some embodiments, when the lead rotates in one direction, the electric resistance of one of the wires is increases while the electric resistance of the second wire decreases.

In some embodiments, the orientation element is a sensor which detects changes in radio-frequency fields surrounding the sensor. In some embodiments, the radio-frequency fields, are generated from at least two sources with a fixed position in space. In some embodiments, the radio-frequency fields have different parameter values, for example different frequencies. In some embodiments, the orientation sensor detects the two different radio-frequency fields and detects changes between the two fields. In some embodiments, rotation or twisting of the lead changes the values of the received fields or a relation between the received fields.

In some embodiments, the orientation element is a magnetic field sensor positioned on the lead. In some embodiments, the magnetic field sensor measures a magnetic field generated from an external source, optionally located outside of the head. In some embodiments, when the measured electric field is changes, for example when the lead is rotated or twisted, an indication is provided to the user and/or to an external machine.

In some embodiments, the sensor is an optical fiber twist sensor which measures the twist or torsion of the lead. In some embodiments, a system connected to the sensor measures the differences in light properties and/or in light parameter values between the light inserted into the lead and the light reflected from the lead. In some embodiments, the changes include for example the amount of light reflected compared to the amount of light projected into the lead.

An aspect of some embodiments relates to functionally mapping brain tissue surrounding a lead based on signal recorded by electrodes on the lead. In some embodiments, the functionally mapping results are used for inferring at least part of an additional trajectory positioned in a distance from a lead insertion trajectory. In some embodiments, the additional trajectory is inferred based on directional signals received from brain tissue surrounding the lead insertion trajectory. In some embodiments, a plurality of functionally mapped trajectories or part of trajectories, for example a part of the trajectory that faces an electrode or group of electrodes or the distal section of the lead are inferred. Alternatively, a single trajectory or part of a trajectory, for example a part of the trajectory that faces an electrode or group of electrodes or the distal section of the lead is inferred from multiple directions signals, optionally using a multi-channel algorithm.

In some embodiments, the recorded signals from the surrounding tissue are functionally tagged using a set of rules or a table of rules. In some embodiments the set or the table of rules is generated using machine learning algorithms or using a statistical-based analysis or by any other manual, semi-automatic or automatic methods.

In some embodiments, an indication is provided to a user during or after the insertion of the lead regarding an alternative, and optionally a more optimal insertion trajectory based on the functional mapping described above. Optionally, an indication is provided to a user regarding a preferred orientation of the lead relative to the surrounding tissue for delivery of a DBS treatment, based on the functional mapping of the surrounding tissue.

An aspect of some embodiments relates to directing at least one electrode to a desired position on the lead surface during the manufacturing of the lead. In some embodiments, the electrode is directed by at least one channel and/or at least one opening located in the lead lumen. In some embodiments, the at least one channel and/or at least one opening are formed in a distal coupler positioned in the lumen of the lead. In some embodiments, the distal coupler accurately directs at least one microelectrode to a desired position on the circumference of the lead. Alternatively or additionally, the distal coupler directs a microelectrode to a desired position in the distal tip of the lead. Optionally, the distal coupler comprises at least two channels for directing at least two electrodes to at least two different positions on the lead circumference.

An aspect of some embodiments relates to reducing external electro-magnetic noise in recorded signals from an electrode lead by shielding electrode conductors placed in the internal lumen of the lead from outside electro-magnetic fields and optionally from adjacent electrodes. In some embodiments, a lead comprises a flexible electrically conductive shield positioned between the electrode conductors and the lead internal surface. Optionally the lead covers at least 70%, for example 80, 85, 90, 95% or any intermediate or larger coverage percentage of the conductor's length and/or circumference. In some embodiments, the shield comprises a braided shield or a mesh shield, optionally made from electrically conductive wires. In some embodiments, the shield allows, for example to twist the lead during the navigation process and to shield the internal electrode conductors from external electro-magnetic fields.

In some embodiments, the shield is comprised of thin electrically conducting wires with a diameter smaller than 150 microns, for example 110, 100, 90 microns or any intermediate or smaller diameter. In some embodiments, the braided shield is comprised of similar thin electrically conducting wires. In some embodiments, the shield is shaped and sized to fit inside a lead having a diameter of at least 1 mm, for example 1.1, 1.2, 1.27, 1.3 or 1.4 mm or any intermediate or larger diameter. In some embodiments, if the shield increases the rigidity of the lead, then the rigidity of the lead is adjusted by using a different polymer which is less rigid to produce the lead. In some embodiments, if the shield is found to increase lead stiffness excessively, a more compliant material is selected for the lead body to achieve the desired overall mechanical stiffness.

In some embodiments, the shield is made by spinning a thin wire or a plurality of thin wires held side-by-side into a coil. In some embodiments, the coil is shaped and sized to be inserted into a gap between the signal conductors and the external wall of the lead.

In some embodiments, the shield comprises at least one connector, for example a male and/or a female connector to allow electrical connection to an external recording unit, for example a differential amplifier. In some embodiments, the external electro-magnetic signal is electrically directed by the shield to the differential amplifier and is optionally used to subtract at least some of the noise signal from the signals recorded by the lead electrodes.

In some embodiments, the shield comprises at least one channel shaped and sized for directing a single electrode conductor. In some embodiments, the single channel is used for directing each electrode a desired positioned on the lead outer surface and/or for shielding each electrode conductor from the rest of the electrode conductors.

An aspect of some embodiments relates to an electrode lead with an internal distal coupler. In some embodiments, a distal coupler comprises at least one channel sized and shaped to hold at least one electrode. Alternatively or additionally, the channel holds at least one electrode wire. In some embodiments, when the electrode or the electrode wire is positioned within the channel, the distal coupler is introduced into an internal lumen of a lead. Alternatively, a lead or at least a section of the lead, for example the distal section of the lead is formed around the distal coupler. In some embodiments, a polymer is casted around the distal coupler and over the wires. In some embodiments, the distal coupler serves to protect the electrode wires during the formation of the lead.

In some embodiments, the lead and/or the system and/or the methods described herein are used for navigation in other tissues of the body, for example in the spinal cord.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary General Lead Implantation Process

According to some embodiments, when a person suffers from a neurological condition it is possible to perform an electrical intervention to alleviate some of his symptoms. This is done by insertion of an electrode to a desired target in the brain and applying an electric field by the electrode to the brain tissue.

Figure 1:
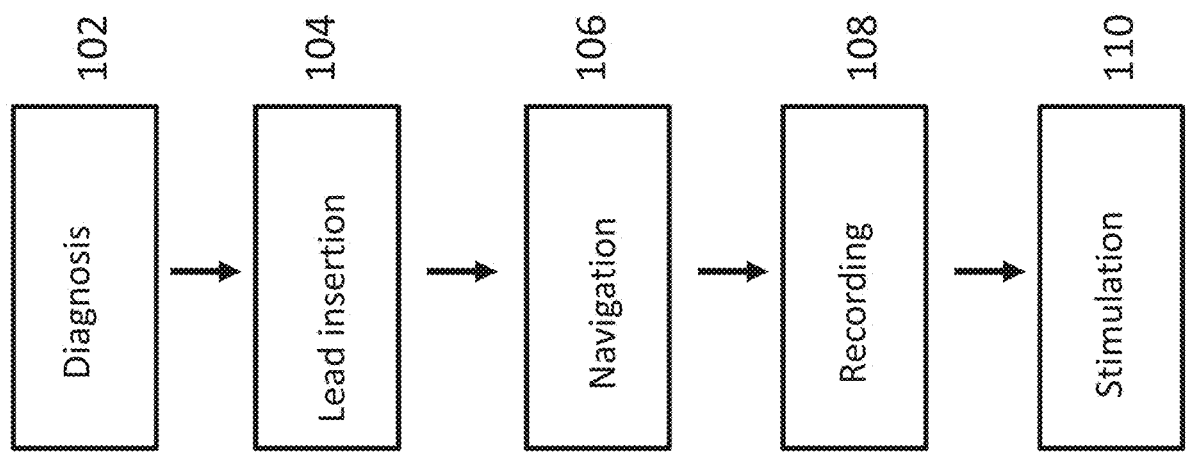
Figure 2:
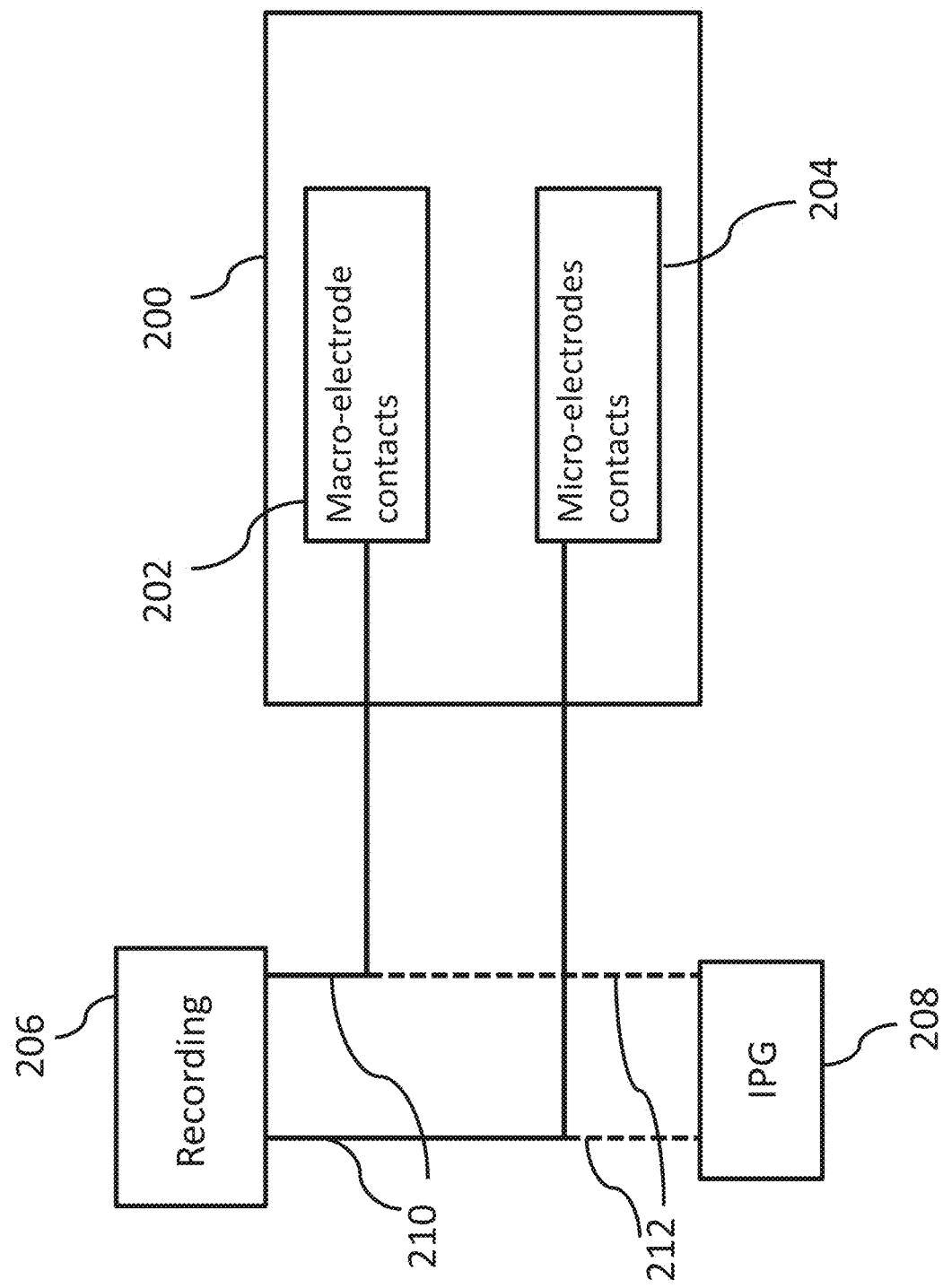

Reference is now made to FIG. 1 depicting a general electrode implantation process according to some embodiments of the invention. According to some exemplary embodiments, when a person suffers from a neurological condition, for example Parkinson's disease, he is being diagnosed by an expert in the field in 102. In some embodiments, during diagnosis 102, a magnetic resonance imaging (MRI) or other imaging tests are performed to identify brain regions relevant to the specific neurological condition. In some embodiments, during the imaging test, the exact position coordinates of brain targets that can be used for an electrical intervention are determined.

According to some exemplary embodiments, after a position of electric intervention brain targets is determined, a cannula is inserted through a hole in the skull. In some embodiments, a lead carrying electrode contacts is inserted through the cannula into the brain in 104. In some embodiments, the lead penetrates the brain with its distal end, facing the tissue. In some embodiments, the cannula and the lead are pushed through the brain tissue manually or using a motorized device.

According to some exemplary embodiments, the cannula and the lead are navigated in 106 through the brain tissue to reach the desired targets coordinates that were determined in 102. Alternatively, the cannula and/or the lead are navigated to different desired brain targets, as determine by an expert in the field. In some embodiments, lead insertion trajectory is determined based on recorded electrical activity of the adjacent tissue using lead electrode contacts. In some embodiments, lead is inserted and/or retracted through the brain tissue based on recorded electrical activity of the adjacent tissue using lead electrode contacts. In some embodiments, lead insertion trajectory is determined based on electrical activity measured by the lead electrode contacts following electric field application. In some embodiments, lead insertion trajectory is determined based on recorded electrical activity as measured by sensors not connected to the navigation lead.

According to some embodiments, navigation in 106 is based on recording and electric field application by the lead contacts.

According to some exemplary embodiments, electrode contacts positioned on the lead measure the electrical activity of the brain tissue facing the electrode contacts in 108. In some embodiments, the measured electrical activity is recorded by a recording device connected to the lead by wires. In some embodiments, the recording device is positioned outside of the patient's body. Alternatively, the recording system is positioned within the patient's body. Optionally the recording system is configured to apply an electric field through the lead electrode contacts, for example an implanted pattern generator (IPG). According to some exemplary embodiments, electrical activity recording is performed by at least one electrode contact of the lead.

Optionally, electrical activity is performed after an electric field is applied by at least one electrode contact to a desired brain region.

According to some exemplary embodiments, after the lead has reached a desired brain target for applying an electric field, lead wires are disconnected from the recording device and are re-connected to an electric field generator device, for example an IPG device. Alternatively, a controller within the recording device signals a pulse generator component within the device to generate an electric field. In some embodiments, the generated electric field is delivered to the brain tissue through electrode contacts placed on the lead surface, facing the brain tissue. In some embodiments, the applied elected field generated by the IPG is used for Deep Brain Stimulation (DBS). In some embodiments, the applied electric field is used to alleviate the symptoms of neurological conditions, for example Parkinson's disease.

Exemplary System

Reference is now made to a system for electrical activity recording and/or application of an electric field to brain tissue, according to some embodiments of the invention. According to some exemplary embodiments, lead 200 comprises at least one micro electrode contact 204 and at least one macro-electrode contact 202, and is configured to be inserted into brain tissue. In some embodiments, lead 200 is configured to measure electrical activity of brain tissue using at least one micro electrode contact 204, and/or at least one macro electrode contact 202. Preferably, lead 200 is configured to measure and/or record electrical activity using both micro electrode contacts and macro-electrode contacts.

According to some exemplary embodiments, lead 200 is connected via wires 210 to recording device 206 during the lead navigation process. In some embodiments, recording device 206 is also configured to generate an electric field to be delivered by wires 210 to lead 200. In some embodiments, the electric field is applied by at least one micro electrode contact 204 and/or at least one macro electrode contact 202 to the brain tissue.

According to some exemplary embodiments, wires 210 are configured to be connected to both recording system 206 and to IPG 208. In some embodiments, once navigation has ended, wires 210 are disconnected from recording device 206 and are connected to IPG 208. In some embodiments, IPG 208 is configured to generate an electric field, to be delivered by wires 210 to lead 200. In some embodiments, the electrical field generated by IPG 208 is delivered to the brain tissue by at least one micro electrode contact 204, and/or at least one macro electrode contact 202 positioned on lead 200.

According to some exemplary embodiments, the electric field delivered to the brain tissue is electric current. In some embodiments, the applied electric field or the electric current is composed of repeating millisecond-scale pulses.

Exemplary Detailed Lead Implantation Method

According to some exemplary embodiments, a patient suffering from a neurological condition is diagnosed by an expert in the field. In some embodiments, if the patient's condition can be treated by electric field application to specific brain regions, the patient undergoes an imaging test, for example an MRI tests to identify the exact location of these brain regions. In some embodiments, once the brain region locations are determined an electrode for applying an electric field is navigated to these regions. However, since the brain moves, the brain regions locations as determined by the MRI test can be changed. In some embodiments, to improve the accuracy of brain region locations, a lead electrode is inserted to the brain to record the electric activity of desired brain regions, prior to insertion of a second electrode for applying the electric field.

Reference now is made to FIG. 3A depicting a detailed lead implantation process according to some embodiments of the invention. According to some exemplary embodiments, a patient suffering from a neurological condition, that its symptoms can be alleviated by electric field application, is diagnosed by an expert in the field. In some embodiments, the patient undergoes an MRI or a CT test to identify the regions where the electric field should be applied, followed by a microelectrode recording (MER) procedure.

According to some exemplary embodiments, the patient is prepared for a microelectrode recording (MER) procedure in 402 by attaching a stereotactic frame and associated apparatus to the patient's scalp, and identifying the insertion point on the scalp. Then, in some embodiments, a cannula is inserted through the skull into the brain in 404, to provide mechanical support for a lead to be inserted through the cannula. In some embodiments, the cannula is made from an electrical conductive material, for example metal. In some embodiments, the cannula is inserted to the brain to a position that is found proximal to the pre-determined anatomical implantation target.

According to some exemplary embodiments, after the cannula insertion in 404, a lead containing at least one micro-electrode contact and at least one macro-electrode contact is inserted through the cannula, to the brain in 406. In some embodiments, the lead is inserted with its distal end at the front, to a desired depth, that was determined during a previously performed imaging test, for example an MRI test. In some embodiments, the lead is connected via wires at its proximal end, which is the end closer to the patient's skull, to a recording device located outside the patient's body. In some embodiments, the lead is connected using a wireless connection to the recording device. Optionally, the recording device is located in or attached to the patient's body.

According to some exemplary embodiments, the lead is inserted by a controlled micro-drive with step sizes of 0.05 mm at most, for example 0.01 mm. Alternatively, the lead is inserted continuously into the brain. In some embodiments, during the insertion of the lead through the cannula, the lead distal end is found outside the cannula in the last 5-40 mm, preferably the last 10-25 mm.

According to some exemplary embodiments, measuring the electrical activity of brain tissue is performed by at least one micro-electrode contact and/or at least one macro-electrode. Alternatively, measuring the electrical activity of brain tissue is performed by at least two micro-electrode contacts. Optionally, measuring the electrical activity of brain tissue is performed by at least two macro-electrode contacts. In some embodiments, the desired combination of electrode contacts to be used for measuring the electrical activity of brain tissue is pre-determined.

Alternatively, the desired combination of electrode contacts is determined during the measuring process. In some embodiments, the electrical activity of the brain tissue is measured while the lead continuously inserted into the brain. In some embodiments, the lead is twisted or rotated in a desired angle or orientation during the measurement of the electrical activity.

According to some exemplary embodiments, measuring the electrical activity of brain tissue is performed in combination with application of an electric field to the brain tissue. The applied electrical field is delivered to the tissue by at least one micro-electrode contact and/or at least one macro-electrode contact.

According to some exemplary embodiments, the electrical activity of the brain tissue is measured and used to determine the electric field application parameter values of an IPG. Alternatively, the electric field application parameter values of the IPG are determined based on electrical activity measurement of the brain tissue following an electric field application.

According to some exemplary embodiments, the measured electrical activity of the brain tissue is recorded in the recording device. In some embodiments, the measured electrical activity is recorded and stored in a memory circuitry connected to the recording device.

According to some exemplary embodiments, measuring the electrical activity of brain tissue in 408 is performed by micro-electrode contacts at the distal end of the lead, during the insertion of the lead into the brain. In some embodiments, electrical activity of brain tissue is measured to determine a desired depth for applying an electric field to the tissue. The electric field is applied by a more proximal electrode contact, which is placed at the desired depth.

According to some exemplary embodiments, once the desired depth is determined and/or the desired target is determined, the cannula is retracted in 410. In some embodiments, a stylet wire is removed from the lead lumen prior to cannula retraction. In some embodiments, the cannula is used with at least one micro-electrode contact and/or at least one macro electro contact to measure the electrical activity of the brain tissue in 408. According to some exemplary embodiments, the cannula is retracted such that its lower end is extracted to a desired height above the desired target. According to some embodiments, after the cannula is retracted, the lead is fixed to the patient's skull. Alternatively, the lead is fixed to the brain tissue.

Optionally, the lead is fixed to an apparatus located outside the patient's skull, for example to a mechanical fixation device.

According to some exemplary embodiments, a verification process is performed in 412 after lead is fixed. In some embodiments, fixation is performed that at least one micro-electrode contact and/or at least one macro-electro contact to be used for electric field application, are placed at the desired depth. Alternatively, fixation is performed to make sure that at least one micro-electrode contact and/or at least one macro-electro contact to be used for electric field application are placed at the desired target. According to some exemplary embodiments, verification is performed by measuring the electrical activity of the brain tissue at the desired depth and/or target. Then, the measured electrical activity is compared to a previously recorded electrical activity to make sure that the electrode contacts are at the desired target.

According to some exemplary embodiments, after the desired target and/or depth is verified in 412, the lead wires are disconnected from the recording device, and are connected to an IPG device in 414. In some embodiments, after the IPG is connected to the lead wires it generates an electric field, for example an electric current, that is delivered through at least one micro-electrode contact and/or at least one macro-electrode contact to the desired brain tissue target.

Exemplary System for Implantation and Navigation

Reference is now made to FIGS. 3B and 3C depicting a system for implantation and navigation of a brain navigation lead according to some embodiments of the invention. According to some exemplary embodiments, a system for implantation and navigation of a brain navigation lead comprises lead 500, having electrode contacts 502 at its distal end, which penetrates first through the brain tissue. In some embodiments, lead 500 is placed within cannula 504, which penetrates through the brain tissue until a desired depth is reached. In some embodiments, lead 500 is connected via adapter 506 to extension cable 508. In some embodiments, for example as shown in FIG. 3C, extension cable 508 connects lead 500 to an external device 510. In some embodiments, extension cable 508 can be replaced to allow connection of lead 500 to external devices with varying number of connections. In some embodiments, external device is a recording system. Alternatively, external device 510 is an IPG for generating electrical pulses, for example for DBS. Optionally, external device 510 is configured both for recording and for generating electrical pulses.

Exemplary Lead in the Brain

Reference is now made to FIG. 3D depicting a lead in a brain during a navigation and/or recording, according to some embodiments of the invention.

According to some embodiments, lead 512 is inserted into brain 516 to a desired depth. In some embodiments, lead 512 comprises insert stylet wire 514 in lead 512 lumen. In some embodiments, lead 512 is connected to a recording system 520 via cable 518. In some embodiments, system 520 is configured to measure and/or record electrical activity. In some embodiments, system 520 is configured to record electric activity and to generate an electric field to be delivered by lead 512 to brain 516.

Reference is now made to FIG. 3E depicting a lead in a brain during electric field application, according to some embodiments of the invention. According to some exemplary embodiments, lead 512 is connected to IPG 524 via cable 522.

Alternatively, cable 522 is configured to connect lead 512 to recording system 520.

Exemplary Orientation Marker

According to some exemplary embodiments, the orientation of at least one electrode on the lead relative to the surrounding tissue is determined by a component connected to the lead or that is part of the lead. In some embodiments, the orientation of the electrode is aligned and fixed prior to lead insertion, for example to ensure recording of directional signals from a desired direction and by a desired electrode. According to some exemplary embodiments, the lead comprises at least one orientation marker which allows, for example to monitor the orientation of the lead within the brain. In some embodiments, the orientation marker allows to, for example to insert the lead into the brain in a desired orientation. In some embodiments, lead orientation relates to an angular direction of at least one microelectrode and/or at least one macro electrode on the lead. In some embodiments, determining of the angular directions of the microelectrodes and/or the macro electrodes allows, for example to associate signals recorded by these electrodes for mapping the tissue and/or generating the resulted map with objective stereotactic coordination.

Reference is now made to FIG. 3F describing a lead, for example a navigation lead with an orientation marker, according to some embodiments of the invention.

According to some exemplary embodiments, lead 530 has an elongated tubular lead body 536 comprising a distal section 532 and a proximal section 534. In some embodiments, lead 530 comprises at least one visual marker 538. In some embodiments, at least part of the marker 538 is positioned at the proximal section 534 of the lead 540, in an area which remains visible to a user during the insertion of the lead and/or during DBS treatment. In some embodiments, the marker is visible through at least one opening or a window in elements surrounding the lead, for example a cannula. In some embodiments, the marker 538 is shaped and sized, optionally as a line, an arrow, an ellipsoid or a dot along the lead body axis to provide a visual indication to a user. In some embodiments, the marker 538 is engraved and/or drawn on the outer surface of lead body 536.

In some embodiments, the marker 538 is aligned with at least one electrode positioned in an area which is hidden from the user during lead insertion and/or during treatment. Optionally, the marker 538 is aligned with at least one electrode positioned in the distal section 532 of the lead 530.

According to some exemplary embodiments, the orientation marker is aligned with an external alignment component. In some embodiments, the external alignment marking is a line, an arrow, an ellipsoid or a dot drawn on a tool designed for that purpose, or on a modified tool such as a DBS-ruler, which is used to determine the insertion depth of a DBS lead.

Reference is now made to FIGS. 3G-3H, depicting a DBS-ruler with an external alignment component, according to some embodiments of the invention. According to some exemplary embodiments, DBS-ruler 540 comprises an elongated body 542 further comprising an axial channel 544 along the elongated body 542. In some embodiments, DBS-ruler comprising a depth measuring scale 546 for determining the insertion depth of a lead, for example lead 530 coupled to the DBS-ruler 540. In some embodiments, DBS-ruler 540 comprising an external alignment component 550 with an alignment marking 552 positioned above channel 544.

In some embodiments, DBS-ruler comprising an asymmetrical opening 548 which is perpendicular to the channel 544 and is shaped and sized to allow insertion of a lead coupling element, for example a lead holder, in a specific orientation. Optionally, the asymmetrical opening 548 is shaped for example as a D or any other asymmetrical shape to prevent the rotation of the lead holder after the lead holder is inserted into the asymmetrical opening.

Reference is now made to FIGS. 3I and 3J depicting alignment of a lead within a DBS-ruler, according to some embodiments of the invention. According to some exemplary embodiments, once the lead holder is inserted into the asymmetrical opening 548, the lead holder clamps 554 are loosened, for example to allow rotation of the lead 530 relative to the lead holder and/or relative to the DBS-ruler 540. In some embodiments, the lead 530 is rotated until marker 538 is aligned with alignment marking 552. In some embodiments, once the marker is aligned with the alignment marking, the lead holder clamps 554 are tightened, for example to prevent the rotation of the lead 530. Alternatively or additionally, a fixation element coupled to the DBS-ruler, for example ruler screw 556 is turned, for example to prevent the rotation of the lead holder relative to the DBS-ruler.

According to some exemplary embodiments, the external alignment feature comprises a window or an opening in a tube. In some embodiments, the opening in the tube allows a user to verify the alignment by visualizing the marker line through the opening. Optionally, the marker is ellipsoid and fits the window in some areas. In some embodiments, the marker line visualized through the window is aligned with a marker positioned on the outer surface of the tube. In some exemplary embodiments, the external alignment feature is drawn or engraved on one of the tools of the stereotactic implantation, for example the electrode holder, and/or the lead-holder and/or a cannula used for the insertion of the lead into the tissue.

Reference is now made to FIG. 3K depicting a lead with a marker that is aligned relative to a cannula alignment marking according to some embodiments of the invention.

According to some exemplary embodiments, lead 530 is placed within a cannula, for example guiding cannula 580. In some embodiments, the lead is rotated within the cannula until a lead marker 538 is aligned with a cannula alignment marking 584. In some embodiments, the lead marker 538 is visible through a window 582 in the cannula body.

According to some exemplary embodiments, during the process of inserting the lead into the brain, the orientation marker is visible to the user, for example to allow the user to determine the electrodes orientation and/or to verify that the electrodes orientation is a desired orientation. In some embodiments, the orientation marker is visible through a window, for example as shown in FIG. 3K.

According to some exemplary embodiments, a plurality of markers, for example 2, 3, 4, 5, 6 or any larger number of markers are positioned on different angular directions. A possible advantage of the plurality of markers is that they can be used for alignment in one of several possible directions. For example, if a user desires the center of a first electrode to face the anterior anatomical direction, a marker with a first color, e.g. blue, is aligned to an external alignment feature. In some embodiments, if the user desires the center of the first electrode to face the antero-medial (i.e. at 45 degrees angles to anterior direction and medial direction) anatomical direction, a line with a second color can be aligned to an external alignment feature. In some embodiments, the lead is inserted in an orientation in which the first marker, which was initially aligned with an external alignment feature, is not conveniently observed, for example when the marker faces a piece of equipment that occludes it, yet a second marker on the lead is conveniently observable and provides an indication to the user that the desired alignment is maintained. This indication can be based on alignment to a second external alignment feature present on one of the tools of the stereotactic implantation. In some embodiments, the alignment is based on pattern and/or a design of the marker and/or of the alignment feature.

Additionally or optionally, the plurality of markers are repeated along the lead axis, for example to allow convenient observation in relation to other equipment, e.g. "electrode holder", or "Ben-Gun" or insertion cannula. In some embodiments, when the markers are on a single angular orientation and optionally at different heights, they also serve to indicate that the lead is not twisted, or undergoes torsion, and to verify that the angular orientation is maintained along the lead axis.

Reference is made to FIGS. 3L and 3M, depicting lead alignment relative to an external alignment element with a plurality of alignment markings, according to some embodiments of the invention. According to some exemplary embodiments, an external alignment element, for example electrode holder 586, comprises openings 590 sized and shaped to allow insertion of a lead. In some embodiments, the electrode holder comprises one or more alignment markings 594, optionally associated with each of the openings 590. Additionally, the electrode holder 586 comprises an asymmetrical opening 588 which is sized and shaped to allow insertion of a lead holder in a single orientation through the asymmetrical opening 588.

According to some exemplary embodiments, a lead can be inserted through anyone of openings 590 and to be aligned using the alignment markings that are associated with the specific opening. In some embodiments, for example as shown in FIG. 3M, the marker 538 of lead 530 is aligned according to alignment marking 594 on the surface of electrode holder 586. In some embodiments, once the marker 538 is aligned, at least one screw of fixation screws 596 connected to the electrode holder 586 is tightened to prevent the relative rotation of the lead.

Reference is now made to FIG. 3N describing a process for determining and fixing the orientation of a lead, according to some exemplary embodiments of the invention.

According to some exemplary embodiments, the lead is placed in a lead holder at 600. In some embodiments, the lead holder is connected to a measuring device at 602, for example a DBS-ruler. In some embodiments, the lead holder is connected to the DBS-ruler in a way that allows only a single pre-determined orientation. In some embodiments, the relative rotation of the lead holder is restricted when the lead holder is connected to the DBS-ruler.

According to some exemplary embodiments, the lead orientation is modified relative to an external alignment marking at 604. In some embodiments, the lead orientation is modified by aligning the orientation marker on the lead with at least one external alignment marker of an external element, for example an electrode holder or a cannula, to reach a desired orientation of the electrodes.

According to some exemplary embodiments, the lead orientation is fixed at 606. In some embodiments, the lead orientation is fixed relatively to the external element, for example relative to the lead holder. In some embodiments, the lead orientation is fixed by closing lead holder attachment means, for example lead holder clamps or screws of an electrode holder. In some embodiments, after the lead orientation is fixed, the lead and the lead holder are positioned in a desired orientation relative to the DBS-ruler, and relative to each other.

According to some exemplary embodiments, the lead and/or the lead holder are coupled to a stereotactic device at 608. In some embodiments, the lead is coupled in a way that allows visibility of the marker, for example for monitoring the lead orientation during lead insertion, navigation and/or treatment.

According to some exemplary embodiments, the orientation marker is produced using techniques that maintain the biocompatibility of the device. In some embodiments, the orientation marker is produced using a laser device which emits laser beams to accurately and locally heat the lead body. In some embodiments, the heating changes the color or the reflectibility of the marker surface in a desired shape and/or location on the lead. Optionally, the laser beams are directed towards a metal and/or a polymer component disposed on the lead body, for example a platinum ring, a platinum/iridium alloy ring, a titanium ring, or another shape on a similarly biocompatible metal or polymer. In some embodiments, the resulting shape on the disposed component serves as the orientation marker.

In some embodiments, the orientation marker is marked on the lead by an ink, and then optionally covered by a transparent polymer. In some embodiments, the transparent polymer is applied using a reflow technique in which the polymer is heated to the melting point and applied over the ink marking where it cools and remains. Alternatively, the marker is produced from a polymer, for example mylar or polyurethane, which can be either dyed to a desired color or printed on with a certain color, or otherwise prepared to have a color that is different from the color of the lead, such that it serves as an orientation marker. In some embodiments, this polymer marker is attached to the lead body using the reflow technique.

A possible advantage of determining the orientation and/or the relative position of the lead electrodes, is that it allows to better use the multiple contacts disposed on the lead, for example by understanding in which stereotactic direction the more optimal navigation trajectory is found during the surgery, or which contact would optimally be used to emit directional current for optimal therapeutic effect. Optimal therapeutic effect could generally mean a satisfactory attenuation of the disease symptoms, such as e.g. tremor, rigidity, akinesia, etc., while incurring minimal or zero side effects on the patient, such as muscle activation, dysarthria, paresthesia, etc.

Exemplary Lead

According to some exemplary embodiments, a brain navigation lead has a distal end, which is the lead end that penetrates first through the brain tissue, and a proximal end, which is the lead end located closer to the upper side of the skull. In some embodiments, the brain navigation lead comprises at least one microelectrode contact and at least one macro-electrode contact.

According to some exemplary embodiments, macro-electrodes and microelectrodes are connected to wires within the lead, which connects them to electrode contacts on the outer surface of the lead. In some embodiments, micro-electrode contacts are positioned distally to macro-electrode contacts. In some embodiments, lead comprises a micro-electrode at its distal tip. In some embodiments, macro-electrode contacts are positioned along the circumference of the lead.

According to some embodiments, micro-electrodes are configured to sense electric signals from single neurons and/or neural cell populations residing in small volumes, for example in $0.1 \times 0.1 \times 0.1$ mm$^3$. On the other hand, in some embodiments, macro-electrodes are configured to sense electric signals, for example local field potential (LFP) originating from neuronal population residing in large volumes. Preferably, macro-electrodes are configured to deliver electric field, for example electric current to brain tissue.

Reference is now made to FIGS. 4A-4J depicting leads having different organizations of micro-electrode and macro-electrode contacts, according to some embodiments of the invention. According to some exemplary embodiments, for example as shown in FIG. 4A, lead 700 comprises a single micro-electrode contact 706 at distal end 702 tip, and 4 ring macro-electrode contacts spaced apart along the longitudinal axis of the lead closer to proximal end 704.

According to some exemplary embodiments, for example as shown in FIG. 4B, lead 700 comprises 4 ring macro-electrodes contacts spaced apart along longitudinal axis 711, at least one micro electrode contact 706 near the distal tip of the lead, and at least 2 micro-electrode contacts 707, distributed along the circumference of lead 700.

According to some exemplary embodiments, for example as shown in FIG. 4C, lead 700 comprises 4 spaced apart ring macro-electrode contacts distributed along the longitudinal axis of lead 700, at least 3 micro-electrode contacts 709 distributed along lead 700 circumference. In addition, lead 700 further comprises a single micro-electrode contact 706 at its distal end tip.

According to some exemplary embodiments, for example as shown in FIG. 4C, lead 700 comprises at least one micro electrode contact, at distal end 702 of the tip, and at least two micro-electrode contacts 718, located proximally to contact 706, distributed along the circumference of lead 700. In some embodiments, both micro-electrode contact 706 and contacts 718 are positioned near distal end 702 of lead 714.

In some embodiments, lead 700 further comprises two ring macro-electrodes contacts 708 and 2 rows of segmented macro-electrodes contacts 716. Each row of segmented macro electrode contacts includes at least 3 contacts distributed along lead 700 circumference.

According to some exemplary embodiments, for example as shown in FIG. 4E, lead 700 comprises at least 3 micro electrode contacts 706 at its distal end 702. In some embodiments, lead 700 further comprises segmented macro-electrode contacts 716 organized in four spaced apart rows along the longitudinal axis of lead 700 with at least two macro-electrodes contacts 716 for a segmented ring.

According to some exemplary embodiments, for example as shown in FIG. 4F, lead 700 comprises 4 rows of macro-electrode contacts 716, with at least 3 contacts per row. In some embodiments, lead 700 further comprises 6 micro-electrode contacts 706 (only 3 contacts are visible) distributed along the circumference of lead 700 distal end 702. In this organization, 3 out of the 6 micro-electrode contacts are aligned with the center of a macro-electrode contact, and 3 micro-electro contacts are aligned with a gap between two adjacent macro-contacts.

According to some embodiments, a brain navigation lead comprises a combination of both ring macro-electrode contacts and segmented macro electrode contacts. In some embodiments, segmented microelectrode contacts are distributed along at least one row which is located in a distal position relative to ring macro-electrode contacts. Alternatively, segmented macro-electrode contacts are distributed along at least one row which is located in a proximal position relative to ring macro-electrode contacts. Optionally, at least one row of segmented macro-electrode contacts is located between two ring macro-electrode contacts. In some embodiments, at least one segmented macro-electrode contact is positioned in a row along the longitudinal axis of the lead. In some embodiments, this organization of ring and segmented macro electrode contacts, allow a more accurate application of electric field to the brain tissue, compared to a lead having only ring macro electrode contacts.

According to some exemplary embodiments, for example as shown in FIG. 4G, lead 700 comprises at least 4 micro-electrode contacts 706 in its distal 702 end, and at least 6 ring macro-electrode contacts 708, proximal to micro-electrode contacts 706.

In some embodiments, lead 700 further comprises segmented macro-electrode contacts 718 positioned between micro-electrode contacts 706 and ring macro-electrode contacts 708. In some embodiments, segmented contacts 718 are positioned in at least one row along lead 700 longitudinal axis, facing a desired portion of brain tissue. In some embodiments, facing a desired direction allows segmented contacts 718 to apply an electric field in a desired direction, for example direction 720 and not in the opposite direction 722. In some embodiments, segmented contacts 718 are positioned very close to adjacent macro-electrode contacts. In some embodiments, ring macro-electrode contacts are positioned very close to each other. In some embodiments, segmented macro-electrode contacts and/or ring macro-electrode contacts have a relatively narrow width.

According to some embodiments, a brain navigation lead comprises segmented macro electrode-contacts positioned in a spiral curve along the lead outer surface. In some embodiments the spiral curve comprises a single spiral electrode contact. According to some exemplary embodiments, for example as shown in FIG. 4H, lead 700 comprises micro-electrode contacts 706 at its distal 702 end, and segmented macro-electrode contacts positioned in a spiral curve along lead 700 outer surface.

According to some embodiments, a brain navigation lead comprises at least two ring macro-electrode contacts, where one of the two ring macro-electrode contacts is positioned in angle relative to the other rind macro-electrode contact.

According to some exemplary embodiments, for example as shown in FIG. 4I, lead 700 comprises micro electrode contacts 706 at its distal 702 end, and at least two ring macro-electrode contacts proximal to the micro-electrode contacts. In some embodiments, one ring macro-electrode contact 727 of at least two ring macro-electrode contact is positioned in a desired angle 724 relative to a second ring macro-electrode contact 727.

According to some embodiments, for example as shown in FIG. 4J a brain navigation lead comprises at least one macro-electrode contact, with a varying width along the circumference of the lead. According to some exemplary embodiments, lead 700 comprises at least one micro-electrode contact 706 at its distal end, and at least one ring macro-electrode contact 726 with a varying width more proximal to micro-electrode contact 706.

Reference is now made to FIGS. 5A-E depicting a brain navigation lead according to some embodiments of the invention. According to some exemplary embodiments, lead 800 comprises micro-electrode contacts 810 at its distal end in the same configuration as in FIG. 4C, and at least 1 row of macro-electrode contacts, for example 4 rows of macro-electrode contacts, for example as shown in FIG. 4D, proximally to micro-electrode contacts 810. In some embodiments, lead 800 is manufactured from an electrical insulator material 808, and electrode contacts are manufactured from an electrical conducting material, for example copper. In some embodiments, the diameter 807 of lead 800 is between 0.2-2.5 mm, for example 0.5-1.5 mm. In some embodiments diameter 807 is 1.27 mm. In some embodiments, the length 806 of lead 800 is between 50-600 mm, for example between 100-500 mm.

Alternatively, length 806 is between 20-100 mm.

Optionally, length 806 is 400 mm. In some embodiments, the width 804 of each macro-electrode contact 802 is between 0.5-10 mm, for example 0.6-2.5 mm.

Alternatively, width 804 is between 0.8-8 mm. Optionally, width 804 is 1.5 mm. In some embodiments, the space 809 between each macro-electrode contact 802 is between 0.1-50 mm, for example 0.2-7 mm. Alternatively, space 809 is between 0.5-20 mm. Optionally, space 809 is 0.5 mm.

According to some embodiments, macro-electrode contact width is between 0.1-3 mm, for example 0.5-1.5 mm. Optionally, macro-electrode contact width is between 0.1-1.5 mm. According to some embodiments, macro electrode contact diameter is between 0.2-2 mm, for example 1.3 mm.

According to some exemplary embodiments, micro-electrode contacts have a diameter between 5-50 micron, for example 25 micron.

According to some embodiments, the longitudinal distance between macro-electrode contacts is between 0.1-3 mm, for example 0.5 mm. According to some embodiments, the longitudinal distance from the bottom ring macro-electrode contact to a distal tip micro-electrode contact is between 0.6-3 mm, for example 1.5 mm.

According to some exemplary embodiments, the longitudinal distance from the bottom ring macro-electrode contact to at least 3 micro-electrode contacts located along the circumference of the lead is 0.2-0.9 mm, for example 0.5-0.7 mm.

According to some embodiments, the distance between macro-electrode contacts on the lead circumference is 50-200 micron, for example 100 micron. In some embodiments, the distance between micro-electrode contacts on the arc is 0.6-2 mm, for example 1 mm.

According to some embodiments, the angular distance between 6 micro-electrode contacts on the lead circumference is $\pi/3$ between the centers of the contacts. In some embodiments, the angular distance between 3 micro-electrode contacts on the lead circumference is $2/3\pi$.

According to some embodiments, the micro-electrode contacts are unipolar. In some embodiments, each micro-electrode contact is connected by a single wire. In some embodiments, measuring electrical activity can be bi-polar if potential is fed from two nearby contacts into two inputs of a differential amplifier.

Exemplary Orientation Sensor

According to some exemplary embodiments, at least one sensor is positioned on the lead to determine the orientation of the electrodes, for example directional electrodes on the lead or the twisting of the lead by a non-imaging technique. In some Alternatively or optionally, if the electrode is helical then the sensor provides an indication regarding the depth of the electrode based on the orientation of the electrode. In some embodiments, the sensor is positioned proximally to the distal tip of the lead, for example in a distance of up to 50 mm from the distal tip. Alternatively, the sensor is positioned proximally to at least one electrode or electrode contact of the lead. In some embodiments, the lead comprises both a sensor proximally to the distal tip and at least one sensor proximally to an electrode on the lead circumference. In some embodiments, the sensor measures the lead orientation using a magnetic field, strain-related changes in resistance, radio-frequency transmission, radio-frequency reception, ultrasound transmission/reception, ultrasound reflection using an external sensor or optical transmission/reception, for example infra-red.

Reference is now made to FIG. 5B, depicting a lead with an orientation sensor and a marker according to some exemplary embodiments of the invention.

According to some exemplary embodiments, a lead 811 comprising an elongated body 812, optionally a tubular or a cylindrical body with a distal section 813 and a proximal section 814. In some embodiments, the lead 811 comprising at least one electrode, for example a microelectrode or a macro electrode at the distal section 813. In some embodiments, the electrode 815 is electrically connected by electrical wiring, delivered through lumen 818 of the body 812 to a recording circuitry 823 of a control system 819.

According to some exemplary embodiments, lead 811 comprising an orientation sensitive element, for example an orientation sensor 816 positioned within the lumen 818 or on surface of the body 812. In some embodiments, the sensor 816 is electrically connected to an orientation detection circuitry 825 of control system 819.

In some embodiments, when orientation sensor detects a change in the orientation of the lead and/or electrodes, for example, rotation or twisting of the lead, the sensor 816 delivers a signal to orientation circuitry 825. In some embodiments, the orientation circuitry 825 is under the control of control circuitry 821 which delivers an indication to the user regarding the change in orientation through interface 829.

According to some exemplary embodiments, the orientation sensor 816 is a gravitational sensor, which detects changes in the effect of the gravitational field. In some embodiments, these changes occur when the orientation of the sensor relative to the ground, or relative to a gravitational base line value is changed.

According to some exemplary embodiments, the orientation sensor 816 detects changes in resistance of electrode wires or sensor wires. In some embodiments, wires are coiled in a specific direction inside the lumen 818 of the lead 811. In some embodiments, when the lead turns in a direction similar to the coiling direction, the wires are stretched and the resistance is increased. Alternatively, when the lead rotates in a direction opposite to the coiling direction, the resistance is decreased.

According to some exemplary embodiments, the orientation sensor 816 is a magnetic sensor, which detects changes in a magnetic field surrounding the sensor. In some embodiments, a magnetic field 831 is applied by an external electromagnetic field generator 829, positioned outside of the head. In some embodiments, sensor 816 detects changes in the magnetic field as a function of the orientation of the lead, for example changes that occur during the rotation or twisting of the lead.

According to some exemplary embodiments, the orientation sensor 816 detects changes in radiofrequency signals transmitted from at least two spaced apart transmitters. In some embodiments, the radiofrequency signals received by the sensor change as a function of the distance of the orientation sensor 816 from each of the transmitters.

According to some exemplary embodiments, control system 819 comprises memory 827, for example for storing orientation values of the lead, base line values of lead orientation, recorded signals from the orientation sensor and/or from the electrode 815.

According to some exemplary embodiments, lead 811 comprising a marker 817, for example marker 538 shown in FIGS. 3F, 3I and 3J. In some embodiments, marker 817 is positioned in the proximal section 814 of the lead 811, and is optionally remains visible throughout the lead navigation process and/or the DBS treatment. In some embodiments, the marker 817 is aligned with at least one alignment feature of a device connected or associated with the lead 811.

According to some exemplary embodiments, the lead 811 comprise both an orientation sensor 816 and a marker 817. In some embodiments, the marker is used to align the lead 811 relative to a reference point before lead insertion, and the orientation sensor is used to monitor the orientation of the lead during the navigation or treatment procedures. In some embodiments, the marker is used to determine the orientation of the proximal section 814 of the lead, while the orientation sensor 816 is used to determine the orientation of the distal section 813 of the lead 811 which is hidden from a user during the lead navigation process and DBS treatment.

Reference is now made to FIGS. 5C and 5D depicting a lead with an orientation sensor, according to some embodiments of the invention.

According to some exemplary embodiments, for example as shown in FIG. 5C a lead 820 comprises at least one sensor 826 for measuring the orientation of at least one microelectrode, for example microelectrode 830 and/or at least one macro electrode, for example macro electrode 828 on the lead. In some embodiments, the sensor is positioned at the distal section 824 of the lead, optionally in a close distance, for example up to 20 mm from one of the electrodes. Alternatively, the sensor 826 is located at any position along the lead 820. In some embodiments, the sensor 826 is electrically connected by electric wire 832 to system 834. In some embodiments, the sensor 826 transmits signals that are associated with the lead orientation and/or with the orientation of one of the electrodes via wire 832 to system 834. In some embodiments, the system 834 determines the orientation of the lead and/or electrodes based on the signals and optionally provides an indication to the user regarding this orientation. In some embodiments, sensor 826 is electrically connected to at least one additional orientation sensor positioned on the lead 820.

According to some exemplary embodiments, for example as shown in FIG. 5D, lead 836 comprises a wireless orientation sensor 838. In some embodiments, wireless orientation sensor is positioned in a close distance of up to 20 mm from the closest microelectrode 842 or the closest macro electrode 840. Alternatively, the wireless orientation sensor is located at any position along the lead 820. In some embodiments, the wireless orientation sensor 838 transmits wireless signals, for example wifi, Bluetooth to a receiver 844 of system. Alternatively, the sensor is a passive component, and the system can wirelessly sense the orientation of the sensor for example, by transmitting electro-magnetic or ultrasonic waves, or by inducing a magnetic field and measuring the disturbance caused by the sensor, or by the sensor detecting a magnetic field which is spatially encoded such that the spatial location can be inferred from the magnetic field properties.

According to some exemplary embodiments, the orientation sensor is optionally in communication with one or more additional sensors placed outside the brain, for example on the scalp or dura, or on a more superficial layer of the brain e.g. cortex. In some embodiments, the one or more additional sensors are optionally coupled to one or more cannulas which are inserted into the brain in the procedure. Alternatively, the cannulas are in contact with the patient body excluding the head, or not in contact with the patient body at all. In some embodiments, the at least one additional sensor is used to receive or transmit a signal, for example by way of a magnetic field, radio-frequency transmission or receiving, ultrasound transmission/reception or optical transmission/reception (e.g. infra-red). In some embodiments, the coupled reception—transmission performed by the first sensor placed on the lead distal end, and the second sensor placed outside of the brain allows, for example to infer the orientation of the lead distal end and the macro electrodes and/or micro electrodes disposed on it.

In some embodiments, the first sensor placed on the lead distal end is a passive component, and the second sensor placed outside is used to wirelessly sense the orientation of the first sensor for example by transmitting electro-magnetic or ultrasonic waves, or by inducing a magnetic field and measuring the disturbance caused by the first sensor.

Reference is now made to FIG. 5E depicting a lead with an orientation sensor and an additional sensor which is placed outside of the brain, according to some embodiments of the invention.

According to some exemplary embodiments, lead 848 comprises an orientation sensor 852 positioned in a close distance from electrodes 847. In some embodiments, sensor 852 transmits signals to system 850 which also receives signals from at least one external sensor 854 which is position outside of the brain. In some embodiments, the external sensor 854 is positioned inside or outside the skull. In some embodiments, the external sensor is positioned on any part of the body or in a distance from the body. In some embodiments, the external sensor 854 communicates with orientation sensor 852 by transmitting and/or receiving signals from the orientation sensor 852 which is positioned inside the brain. In some embodiments, system 850 determines the position and/or the orientation of the lead and/or lead electrodes based on signals derived from both the orientation sensor 852 and the external sensor 854.

Exemplary Fiber Optic Twist Sensor

According to some exemplary embodiments, the sensor is an optical fiber twist sensor which allows detection of the twist or torsion of the lead. In some embodiments, the optical fiber twist sensor is positioned along the lead axis, and optionally reaches the distal section of the lead. In some embodiments, a system connected to the sensor measures the differences in light properties and/or in light parameter values between the light inserted into the lead and the light reflected from the lead. In some embodiments, the changes include for example the amount of light reflected from a fiber optic positioned inside the lead compared to the amount of light projected into the lead.

Exemplary Resistance-Sensitive Orientation Sensor

According to some exemplary embodiments, the orientation sensor measures changes in wire resistance that indicate torsion, which is rotation around the lead axis ("roll") of one part of the lead with respect to another part of the lead. In some embodiments, the conduction of the wire is generally affected by the wire length and cross section, according to the equation $R=\rho L/A$, where $\rho$ is the specific resistivity, L is the length and A is the cross sectional area. When a wire is stretched, L increases while A decreases, both leading to an increase in resistance, an effect utilized in strain gages. When we coil a wire inside the lead body it has an initial resistance R1. If the lead is rotated in the same direction as the wire is coiled, i.e. giving it a "roll" about its axis in that direction, the wire is stretched and the resistance increases. Rotating the lead in the opposite direction would reduce the tension on the wire and decrease its stretch, thus reducing the resistance of the wire.

In some embodiments, two wires are coiled in opposite directions, such that for lead rotation in one direction, the resistance of the first wire would increase while the resistance of the second wire would decrease. Lead rotation in the opposite direction would lead to an opposite effect, whereby the resistance of the first wire would decrease while the resistance of the second wire would increase. The same would be true if more than one wire is coiled in each direction, for example if 2 or more wires are coiled in one direction, and 2 or more wires are coiled in the opposite direction in the lead body.

According to some exemplary embodiments, as these changes in resistance are small, on the order of 1% or less, sensing these changes requires an electrical circuitry sensitive to such changes must be used. This circuitry may be based on differential changes in the resistance of several resistor elements, such as the well known Wheatstone bridge circuit. For the typical small strains and resistance changes that can be expected in this application, and assuming no temperature changes, when an external voltage V is applied to the balanced Full Wheatstone bridge circuit the voltage measured by the circuit, e, is given by $$e = \frac{GF}{4}[\varepsilon_1 - \varepsilon_2 + \varepsilon_3 - \varepsilon_4]E$$

Where GF is the Gage Factor, a material property relating the change in resistance to the strain $\varepsilon$, $$GF = \frac{dR/R}{\varepsilon},$$

$\varepsilon=dL/L$, and $\varepsilon_1$, $\varepsilon_2$, $\varepsilon_3$, $\varepsilon_4$ are the strains experienced by 4 elements, or coiled wires in our case. As may be understood from the equation, rotating the lead in one direction would lead to a positive voltage measurement, e>0, while rotation in the opposite direction would lead to a negative voltage measurement, e<0. Increasing the input voltage, E, and using materials with high GF, leads to increased measurement sensitivity.

Similarly, a Half Wheatstone bridge may be used, in which two resistor elements are sensitive to strain and two are "dummy" resistors with fixed resistance values, and could be outside the lead body. Then the measured voltage would follow the equation:

$$e = \frac{GF}{4}[\varepsilon_1 - \varepsilon_2]E$$

Similarly, a quarter Wheatstone bridge may be used, in which only one element is a strain sensitive element and the other three are fixed "dummy" resistors, and then the measurement follows:

$$e = \frac{GF}{4}\varepsilon_1 E$$

These circuits are known in the art and additional modifications may be applied to counter the effect of temperature changes during the measurement, or other effects.

According to some exemplary embodiments, strain sensitive wires may be used without being coiled within the lead body. Instead, two or four strain sensitive elements may be placed on the lead surface from within or without. These gages typically have a specific direction in which they are sensitive to strain, and should placed such that their sensitive direction is not parallel to the lead axis. Two gages can be placed with a 90 degrees angle between them, both at 45 degrees to the lead axis. Four gages can be placed such that two have their strain sensitive directions aligned, and the other two have their strain sensitive directions aligned, with the first pair at 90 degrees angles to the second pair, and each pair at 45 degrees to the lead axis. This configuration is similar to the so-called "rosette" strain-gage configuration for measuring strains in a plane. In each of these configurations, a type of Wheatstone bridge or similar circuitry is required for performing a measurement.

Exemplary Electromagnetic-Orientation Sensor

According to some exemplary embodiments, the orientation sensor comprises an electromagnetic-sensitive sensor. Electromagnetic positioning of a catheter has been previously described in the art, for example U.S. Pat. No. 7,197,354 entitled "System for Determining the Position and Orientation of a Catheter", which allows for positioning in X, Y & Z and indicating direction changes in "pitch" and "yaw" directions, but not in the "roll" direction—that is not in twisting around the lead axis. In U.S. Patent Application Publication No. 2010/0324412, entitled "Catheter With Obliquely-Oriented Coils" and U.S. Pat. No. 6,593,884, entitled "Intrabody Navigation System for Medical Applications", using multiple sensors is described for sensing the roll of a medical device. In U.S. Patent Application Publication No. 2017/0049357 a single sensor is described for detecting roll in a medical devices.

The principle underlying these sensors is that one or more coils within the lead is sensitive to electromagnetic induction. In some embodiments, this sensitivity is enhanced by the sensor having a ferromagnetic core around which the one or more coils are wound. In some embodiments, an external transmitter transmits an electromagnetic field, which causes a current response in the coil sensor, according to the principle of electromagnetic induction, or Faraday's law. By detecting this current the local electromagnetic field in the sensor surroundings is inferred, and the positioning is based on the system transmitting a spatially-varying magnetic field. Thus, the location in space is encoded by the local electromagnetic field, and detecting this field allows to decode the position in which the sensor is located.

In some embodiments, the differential sensitivity to fields that have different axes, i.e. that have a different flux with respect to the X, Y & Z axis, allows for example to infer the pitch and yaw of the device. In some embodiments, the induced current is maximal when the flux is maximal, i.e. when the direction of maximal change in magnetic field is perpendicular to the coil axis. In some embodiments, a symmetric coil, i.e. a coil wound symmetrically around the core, can thus detect the position in X, Y & Z coordinates, as well as the pitch and yaw, but not the roll of the device. In order to sense the roll of the device, it is required to have a coil that is wound about an axis that is not aligned with the lead axis, and at least two components with different winding angles with respect to the lead axis. These components may be separate coils, or a coil with two portions having different winding angles.

In some embodiments, when the coil is wound at an angle to the lead axis, it responds maximally to a field with maximal flux not parallel to the lead axis, but to the coil axis. When the lead rotates about its axis, i.e. undergoes roll, the coil's preferred direction changes as its own axis is changed due to the lead roll. When there are present at different longitudinal locations on the lead body two components, e.g. two coils with different preferred directions, the differential measurement from the two of them can be used to infer the absolute roll of the lead, in the absence of torsion. When torsion is present such that there is a twist in the lead between the two components, there is a change in the relationship between the two measurements. Thus the relation between the two components itself may be observed, and used to indicate torsion of the lead.

According to some exemplary embodiments, when combined with the lead orientation marker, which indicates the orientation of the proximal part of the lead, the torsion indication is sufficient to infer the lead distal tip orientation. For example: a lead is inserted in the left hemisphere, such that the left side of the lead is in a lateral direction and the right side of the lead is in a medial direction. The lead proximal end is oriented such that distal electrode #1 should be in the anterior direction, and the torsion is indicated to be 45 degrees in the clockwise direction. Then it is inferred that electrode #1 is facing the antero-medial direction. If the torsion is indicated to be 90 degrees in the counter-clockwise direction, electrode #1 is inferred to face the lateral direction. This is irrespective of how the torsion is indicated, by wire resistance changes, single or multiple coil electromagnetic induction, or another technique.

In another example, the orientation sensor comprises an electromagnetic field detector which includes a ferromagnetic core having a perforation and at least one winding wound around the ferrous core. In some embodiments, the perforation provides communication between a first side of the ferrous core and a second side of the ferrous core, for example the first side faces a proximal side of the catheter and the second side faces a distal side of the catheter. The winding produces a current according to the electromagnetic field, wherein the ferrous core increases the sensitivity of the electromagnetic field detector to the electromagnetic field, by increasing a proportionality factor between the current and the electromagnetic field.

Exemplary Recording and Stimulation

Reference is now made to FIG. 6 depicting a process of recording and/or stimulation (electric field application) according to some embodiments of the invention. According to some exemplary embodiments, a brain navigation lead is inserted to a brain in a close proximity to a desired predetermined brain tissue target in 900. In some embodiments, lead comprises micro-electrode contacts at its distal end, and macro-electrode contact closer to the proximal lead end compared to the micro electrode contacts. In some embodiments this allows to use micro-electrode contacts for recording as they are the first contacts to face the brain tissue as the lead moves in the predetermined insertion trajectory.

According to some exemplary embodiments, during the navigation and recording process, the lead is connected to an external device via non-implanted extension cable. In some embodiments, the external device is an IPG configured for both generating electric field and recording electrical activity of brain tissue. In some embodiments this external device is configured to record signals arriving from electrode contacts on the lead. Alternatively, the external system is configured to apply an electric field through electrode contacts on the lead and record the electrical activity of the brain tissue following the electric field application.

In some embodiments, the external device is configured to measure and/or measure parameters from other sensors.

According to some exemplary embodiments, recording parameters are determined in 902. Alternatively, recording and electric field application parameters are determined in 902. Optionally, recording and/or electric field application parameters are determined and/or modified during the navigation process.

According to some exemplary embodiments, the electrode contacts to be used for recording and/or electric field applications are determined in 904. In some embodiments, lead comprises both micro-electrode contacts and macro-electrode contacts, and any combination of micro electrode contacts and/or macro-electrode contacts can be used for measuring electrical activity of brain tissue. Alternatively, any combination of micro-electrode contacts and/or macro-electrode contacts can be used for electrical field application. According to some exemplary embodiments, the distribution of macro and micro electrode contacts, along several positions on the lead outer surface and at several angular positions on the lead circumference allow directional recording of desired brain tissue regions around the lead. Optionally, the distribution of macro and micro electrode contacts, along several positions on the lead outer surface and at several angular positions on the lead circumference allow directional electric field application to desired brain tissue regions around the lead.

According to some exemplary embodiments, after determining which electrode contacts to use for recording, the external device starts to record brain tissue electric activity as the lead penetrates into the brain tissue in 908. In some embodiments, recording is preformed from different combination of micro-electrode contacts and/or macro electrode contacts facing different brain tissue regions, in a form of directional recording. In some embodiments, directional recording is based on the differences between signals arriving from different locations. In some embodiments the recorded signals have the spectral properties of spike signals (300-20 kHz), local field potentials (0.001-600 Hz), or can be found in a broad spectrum (0.001-100 kHz). In some embodiments, sensing electrical activity from different origins is based on both the location of electrode contacts used for sensing, and/or on the polarity of the measurement.

According to some exemplary embodiments, directional recording is used to sense electrical signals from different origins in space, and process these signals to preferred directions in space.

According to some exemplary embodiments, measuring and recording electrical activity follows electric field application to the brain tissue in 906. In some embodiments, the external device connected to the lead electrode contacts is configured to apply an electric field through at least one electrode contact to the brain tissue. In some embodiments, after the electric field was applied, the external device measures the electrical activity of the tissue following the electric field application. In some embodiments, electrical activity measurement is performed using the same electrode contact used for electric field application. Alternatively, electrical activity measurement is performed by other electrode contacts. Alternatively, electrical activity measurement is performed by combining the electrode contact used for electric field application and other electrode contacts located on the lead. In some embodiments, electric field application and/or measurement of electrical activity in 906 is performed using electrode contacts positioned in a desired direction on the outer surface of the lead. In some embodiments, electric field application and/or measurement of electrical activity in 906 is performed using at least one micro-electrode contact and/or at least one macro-electrode contact. In some embodiments, electric field application and/or measurement of electrical activity in 906 is performed using at least one micro-electrode and the electrical conducting cannula.

Alternatively, electric field application and/or measurement of electrical activity in 906 is performed using at least one macro-electrode and the electrical conducting cannula.

According to some exemplary embodiments, combining electric field application and measurement of electrical activity in 906 is used to determine electric pulses parameters generated by an IPG, for example pulse width, pulse repetition frequency, and pulse amplitude. In some embodiments, combining electric field application and measurement of electrical activity in 906 as described herein, can be used to determine which electrode contacts will be used for electric field application by the IPG, for example for DBS of desired brain targets.

According to some exemplary embodiments, based on electrical activity measured and recorded in 906 or 908, the desired depth is determined to position electrode contact for electric field application in 910. In some embodiments, recorded electrical activity is used to determine additional lead insertion trajectories for additional leads in 910. In some embodiments, during the insertion the electrical activity of adjacent tissue is measured by lead electrode contacts and is used to generate a depth fingerprint for desired locations along the insertion trajectory in 910.

In some embodiments, depth fingerprints of several locations can be analyzed and combined to a general electrical activity map of neuronal populations along the insertion path or at desired locations.

According to some exemplary embodiments, recorded electrical activity is used to modify the lead insertion trajectory, as determined by an automatic navigation algorithm. In some embodiments, based on the recorded electrical activity signals, lead is either inserted or retracted until a desired location is reached. In some embodiments, lead insertion trajectory is modified based on measured electrical activity signals following electric field application by electrode contacts on the lead.

According to some embodiments, electric field application parameters are determined based on electrical activity recordings following a previous electric field application. In some embodiments, this is a feedback loop where electric field is applied, and the recorded electrical activity of the tissue following the electric field application is used to determine the parameters of a second electric field application.

In some embodiments, the parameters for the initiating electric field application are predetermined and stored in the electric field application device.

According to some exemplary embodiments, previously recorded electrical activity signals are used to select the electrode contacts for electric field application and/or the desired tissue region for directed electric field application.

According to some exemplary embodiments, the lead and connected devices are configured to apply an electrical field using at least one electrode contact on the lead, and to measure and record electrical activity using another at least one electrode contact, simultaneously. In some embodiments, simultaneously electric field application and electrical activity measurement allow to examine the effect of the applied electric on neuronal activity. The examination provides the feedback required for evaluating the efficacy of the applied electric field parameters, for example lead depth, selection of electrode contacts, amplitude of the current delivered by each contact to the tissue, and temporal application pattern.

According to some exemplary embodiments, the measured electrical activity is used to determine the optimal depth for electric field application by the IPG. In some embodiments, the measured electrical activity is used to generate a depth fingerprint, for tissue regions along the lead insertion trajectory. In some embodiments, the depth fingerprint is used to determine at least one additional lead insertion trajectory.

Figure 7B:
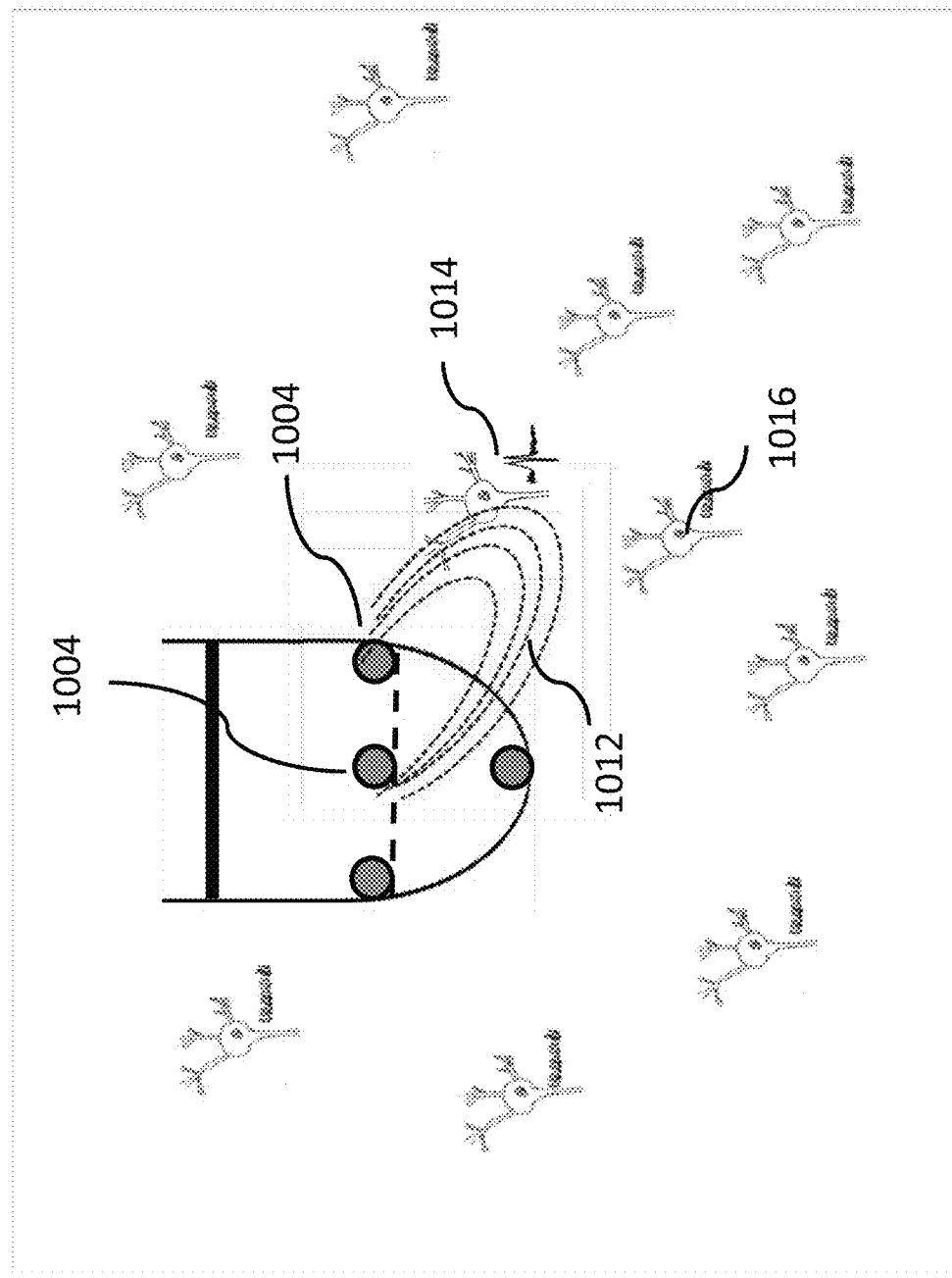

Reference is now made to FIGS. 7A-7G depicting different electrode contacts combinations for directional electric field application, according to some embodiments of the invention. According to some embodiments, an electric field is applied by at least two electrode contacts on the lead, and induces electrical activation of neural cells located at the direction of the applied electric field. In some embodiments, the neurons electrical activation is relative to the current density of the applied electrical field at their location. In some embodiments, each pair of micro-electrode contacts, applies an electric field in a different direction, and therefore can activate different neuronal populations. According to some exemplary embodiments, for example as shown in FIG. 7A, directional electric field 1006 is emitted by micro-electrode contact 1006 located at the lead circumference, and is returned by micro-electrode contact 1002 located at the distal tip of the lead. Alternatively, directional electric field is applied by any combination of two micro-electrode contacts positioned on the lead. In some embodiments, directional electric field 1006 activates neuron 1008 found in the tissue region affected by the electric field, but does not activate neuron 1010 which is located outside the affected region.

According to some exemplary embodiments, for example as shown in FIG. 7B, when using a different pair of micro-electrode contacts, in this case two adjacent micro-electrode contacts, electric field 1012 activates different neurons then in FIG. 7A. In some embodiments, electric field 1012 activates neuron 1014 found in the tissue region affected by electric field 1012, but does not activate neuron 1016 which is located outside the affected region.

Figure 7C:
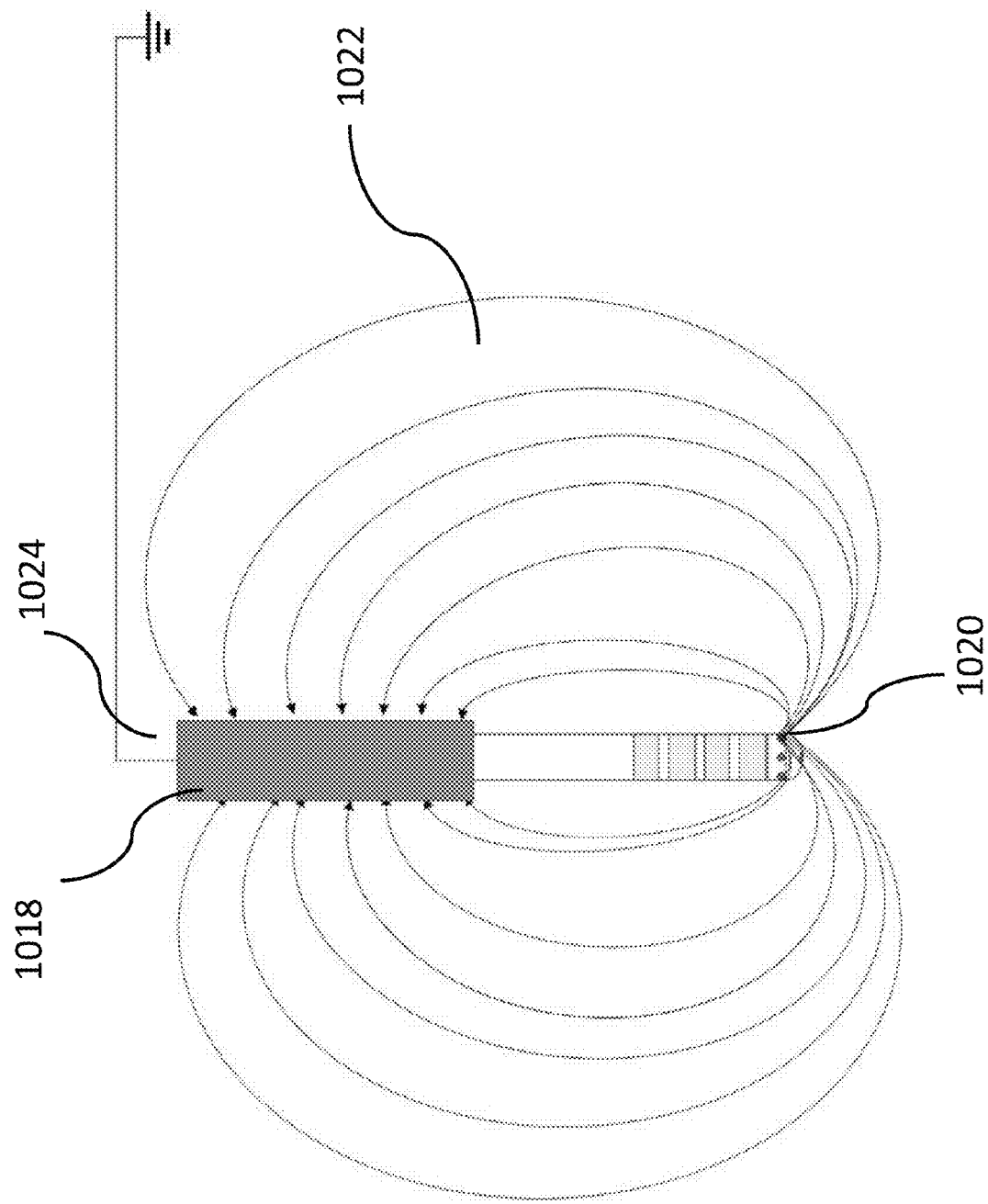

According to some embodiments, a single micro-electrode contact is combined with a conducting element attached to the lead, for example a cannula through which the lead is inserted most of the way towards the target. According to some exemplary embodiments, for example as shown in FIG. 7C, lead 1024 having a similar electrode contacts distribution as lead 700 in FIG. 4C is used to apply an electric field to brain tissue. In some embodiments, lead 1024 applies an electric field, for example current, through micro-electrode 1020, and uses cannula 1018 for current return. The resulted electric field is much larger, compared to electric fields 1012 and 1006 of FIGS. 7B and 7A, respectively.

Figure 7D:
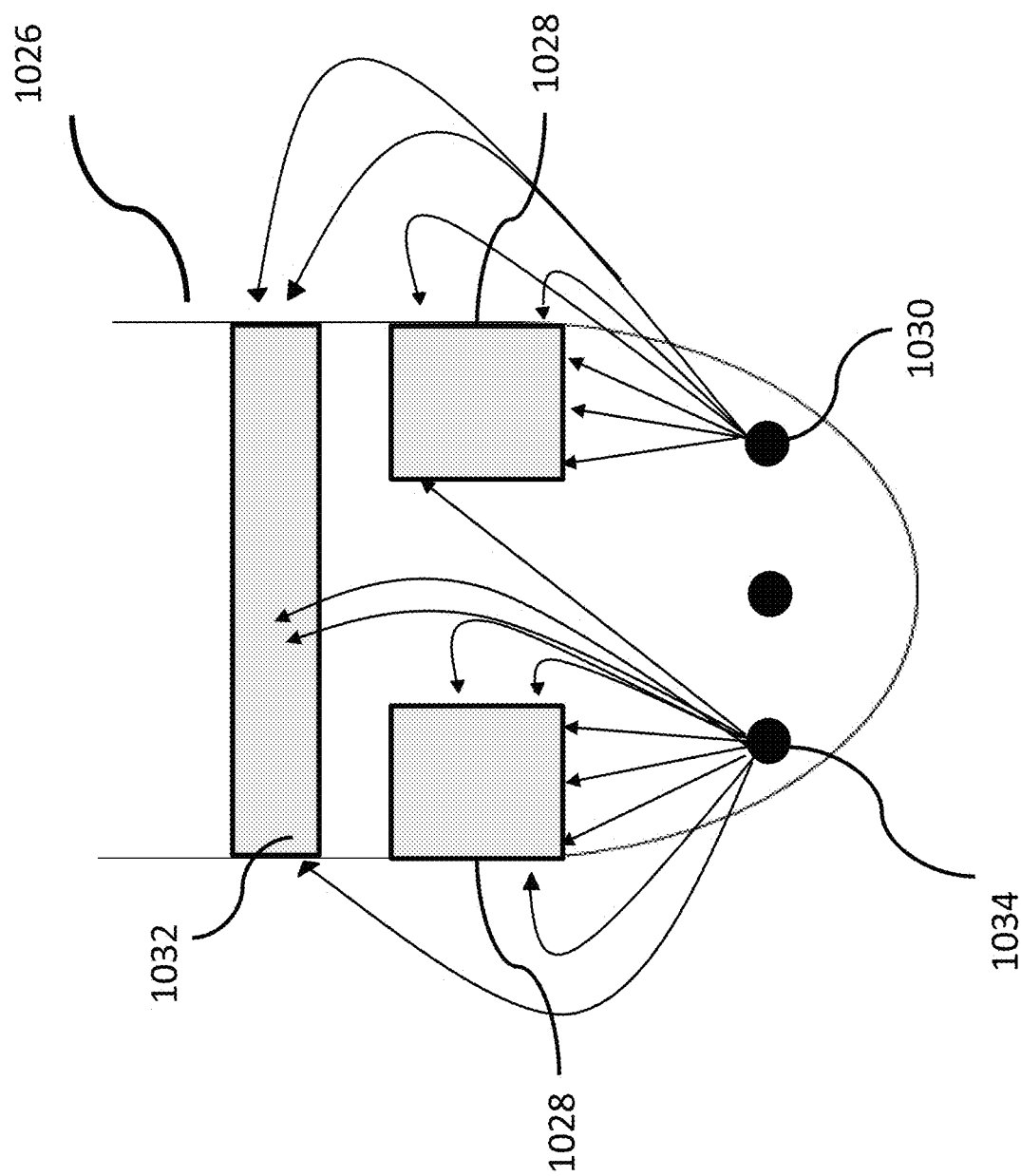

According to some embodiments, a multi polar electric field is applied by at least two micro-electrode contact, and is returned by at least two macro electrode contacts, for example a ring and a segmented macro electrode contact. According to some exemplary embodiments, for example as shown in FIG. 7D, lead 1026 comprises at least 6 micro-electrode contacts located distal to segmented macro-electrode contacts and ring macro-electrode contacts. In some embodiments, micro-electrode contacts 1034 and 1030 are used to emit an electric field, for example by applying current, and macro-electrode contacts 1028 and 1032 are used for current return.

According to some exemplary embodiments, an electric field is applied by combining at least one micro-electrode contact and at least one macro-electrode contact. According to some exemplary embodiments, for example as shown in FIG. 7E, an electric field is applied by segmented macro-electrode contact 1036 for example by applying current, and micro-electrode contact 1038 is used for current return. Alternatively, for example as shown in FIG. 7F, an electric field is applied by micro-electrode contact 1038, and macro-electrode contact 1036 is used for current return.

In some embodiments, for example as shown in FIG. 7E, due to the different sizes of the contacts, the current density, as well as the charge density near the micro-electrode is higher than near the macro-electrode, and the cathodal effect of this configuration will be more spatially selective than the cathodal effect. In FIG. 7F, the relations between cathodal and anodal spatial selectivity are reversed.

Figure 7G:
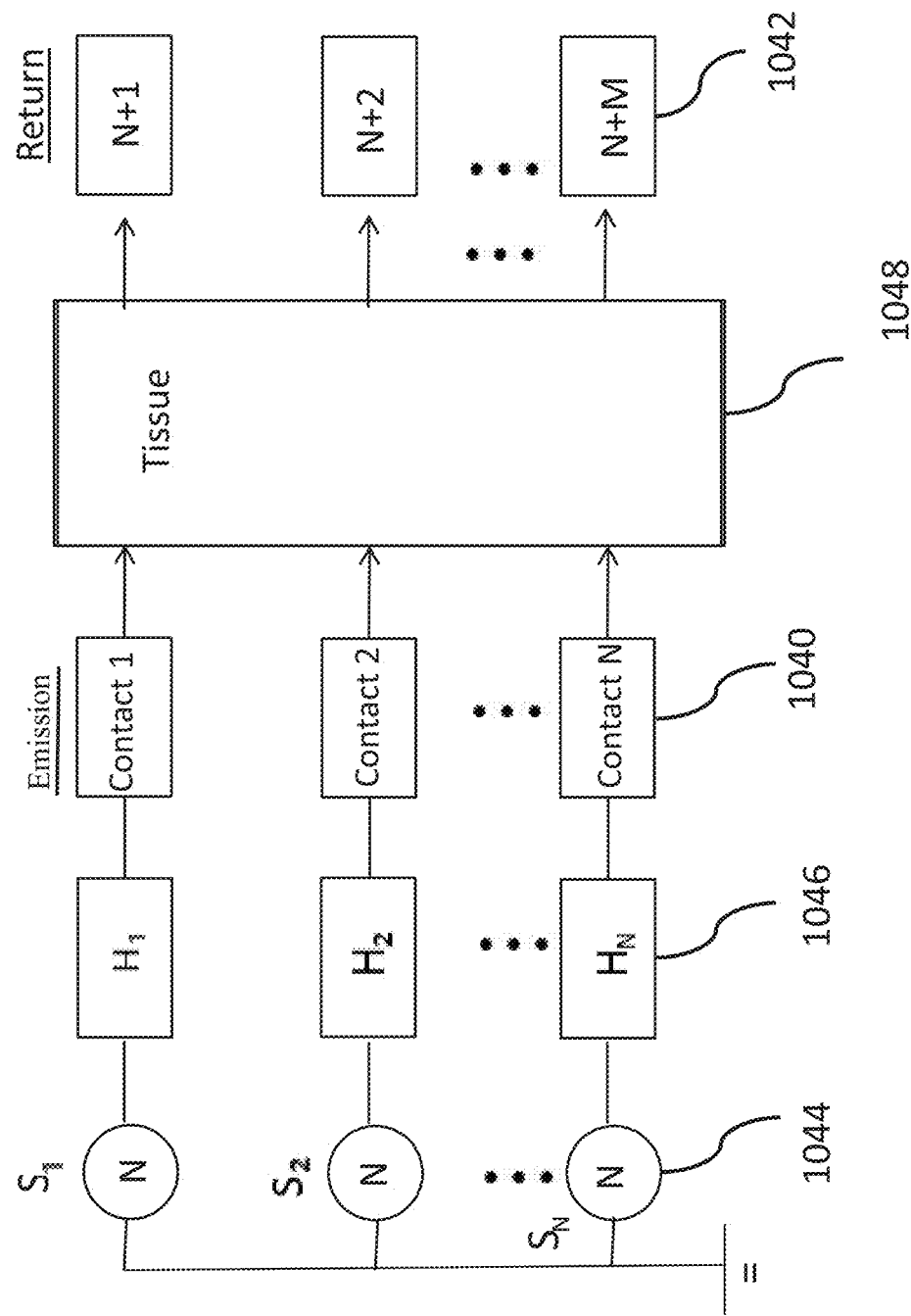

According to some exemplary embodiments, for example as shown in FIG. 7G, depicting a scheme for multi-polar electric field application, contacts 1040 are used to deliver an electric field to tissue 1048, for example as current, and contacts 1042 are used for current return. In some embodiments, each of contacts 1040 are connected to an independent source 1044, and the current from each source 1044 flows through general network 1046 before reaching contacts 1040.

Exemplary Micro-Electrodes Directional Recording

According to some embodiments, a navigation lead having micro-electrode contacts on its outer surface is configured to directional record electrical activity of cells in a tissue region close to each micro-electrode contact. Reference now is made to FIG. 8 depicting directional recording of electrical activity by micro-electrode contacts. According to some exemplary embodiments, at least 2 microelectrode contacts distributed along the lead circumference are adjacent to two different tissue regions. In some embodiments, a microelectrode contact, for example micro-electrode contact 1052, measures and/or records the electrical activity of adjacent neuronal cells, for example neuronal cell 1054. In some embodiments, neuronal cell 1054 is characterized by generating intense, high-frequency spiking, and therefore micro-electrode contact 1052 senses electric potential 1060 that has characteristics of high power, and frequent spikes. On the other hand, in some embodiments, micro-electrode contact, for example micro-electrode contact 1056 is adjacent to neuronal cells, for example neuronal cell 1056 which does not generate spikes or that generates low frequency spikes. In some embodiments, micro-electrode 1050 is adjacent to neuronal cell 1056 and senses an electric potential 1058 that has characteristics of low-power, infrequent spikes.

Exemplary Macro-Electrodes Recording

According to some embodiments, navigation lead comprises macro-electrode contacts distributed along the lead circumference and is configured to measure electrical activity of neuronal cells adjacent to the macro-electrode contact. In some embodiments, at least one macro-electrode contact is referenced to at least another macro-electrode contact. In some embodiments, at least two macro-electrode contacts are referenced to a third macro-electrode contact. Reference is now made to FIG. 9A depicting a combination of two macro-electrode contacts referenced to a third macro-electrode contact according to some embodiments of the invention. According to some exemplary embodiments, a navigation lead comprises micro electrode contacts at its distal end, for example micro-electrode contact 1068, and segmented macro-electrode contacts 1062, 1064, and 1066 distributed along the lead circumference. In some embodiments, electrical activity of neuronal cells is measured by a combination of macro-electrode contact 1062 and 1066, and is referenced by electrical activity measured by macro-electrode contact 1064.

Reference is now made to FIG. 9B depicting multi-polar electrical activity measuring and/or recording by a combination of at least two macro-electrode contacts according to some embodiments of the invention. According to some embodiments, macro-electrode contact 1070 is combined with macro-electrode contact 1074 to measure electrical activity of tissue adjacent to the electrode contacts. In some embodiments, the combined macro-electrode contacts are referenced by at least one macro-electrode contact, for example macro-electrode contact 1072.

Exemplary Macro-Electrode Contacts

According to some embodiments, macro-electrode contacts are shaped in different geometric designs and are configured to be placed on the outer surface of a navigation lead.

Reference now is made to FIG. 10 depicting different geometrical design of macro-electrode contacts, according to some embodiments of the invention.

According to some embodiments, a navigation lead comprises at least one micro-electrode contact 1076 and at least one segmented macro-electrode contact 1078 on its outer surface. In some embodiments, macro-electrode contact 1078 is shaped in the form of a square or a rectangle 1080. In some embodiments, macro-electrode contact 1078 is shaped in the form of a circle 1082 or as an ellipsoid 1084.

In some embodiments, macro-electrode contact 1078 is shaped in the form of a polygon, for example hexagon 1086. In some embodiments, macro-electrode contact 1078 is shaped in the form of a parallelogram 1088 or trapezoid 1090. In some embodiments, macro-electrode contact 1078 is shaped to have at least one internal edge to increase current transfer efficiency, as in 1092. Alternatively, macro-electrode contact 1078 is shaped in the form of a polygon with round corners to mitigate edge effects occurring in corners, where the current density may increase sharply.

Exemplary Current Density

According to some embodiments, a navigation lead comprising at least micro electrode contact and at least one macro-electrode contact is configured to apply an electric field in the form of a current to brain tissue, by using at least one micro electrode contact to emit current, and at least one micro-electrode contact or at least one macro-electrode contact for current return. Alternatively, at least on macro-electrode contact is used to emit current and at least one micro-electrode contact or at least one macro-electrode contact for current return.

Figure 11A:
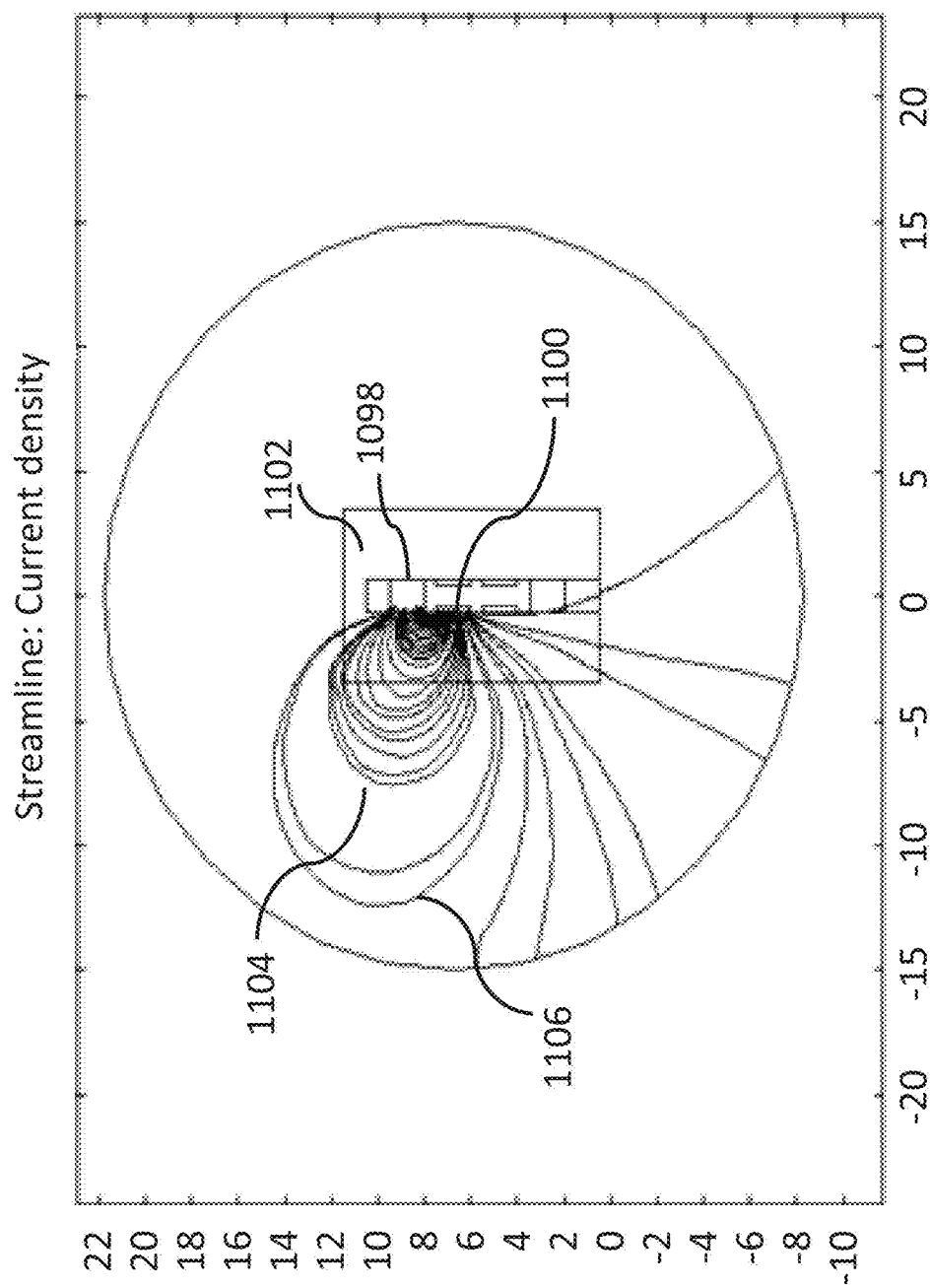
Figure 11B:
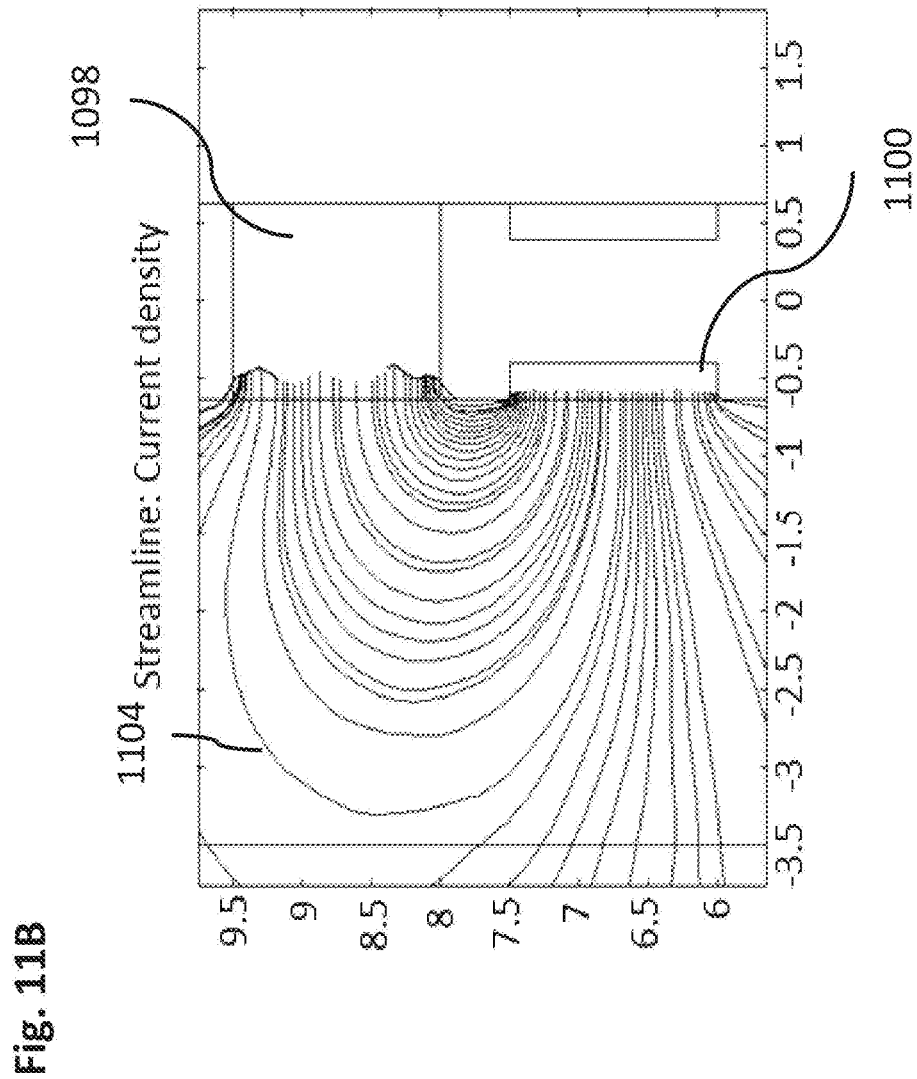

Reference is now made to FIG. 11A depicting electric field application in the form of electric current, by two macro-electrode contacts according to some embodiments of the invention. According to some embodiments, electric field 1104 is applied in the form of a electric current by lead 1102. In some embodiments, a segmented ring macro-electrode contact 1100 is used to emit electric current, and ring macro-electrode contact 1098 is used for current return. Alternatively, ring macro-electrode contact 1098 is used to emit electric current, and segmented ring macro-electrode contact 1100 is used for current return. FIG. 11B is a magnified view of FIG. 11A. Black lines 1106 indicate lines along which electric currents of equal amplitude flow from the emitting contact to the return contact.

Figure 11C:
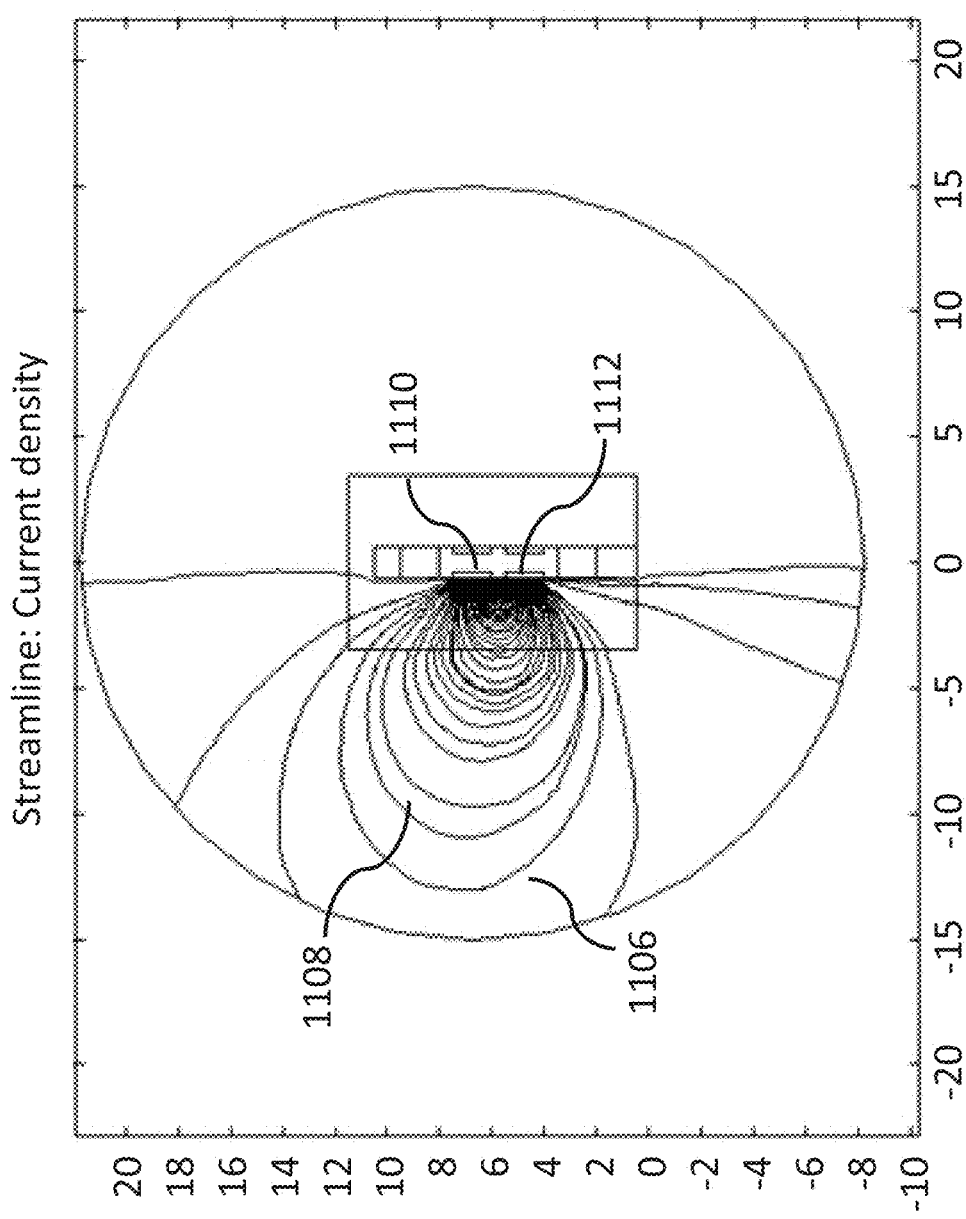
Figure 11D:
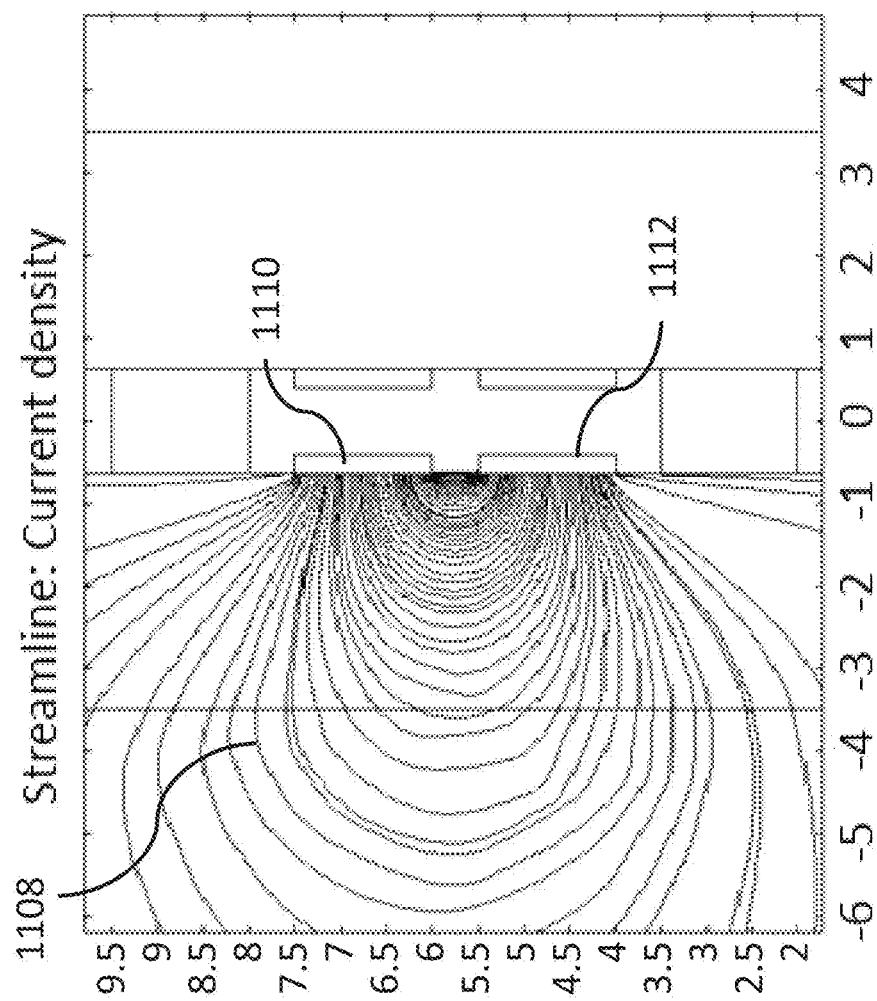

Reference is now made to FIG. 11C depicting electric field application in the form of electric current by two segmented ring macro-electrode contacts according to some embodiments of the invention. According to some exemplary embodiments, electric field 1108 is applied in the form of electric current by segmented ring macro-electrode contact 1112, and is returned by segmented ring macro-electrode contact 1110. Alternatively, segmented ring macro-electrode contact 1110 is used to emit electric current, and segmented ring macro-electrode contact 1112 is used for current return. FIG. 11D is a magnified view of FIG. 11C. Black lines 1106 indicate lines along which electric currents of equal amplitude flow from the emitting contact to the return contact.

Figure 11E:
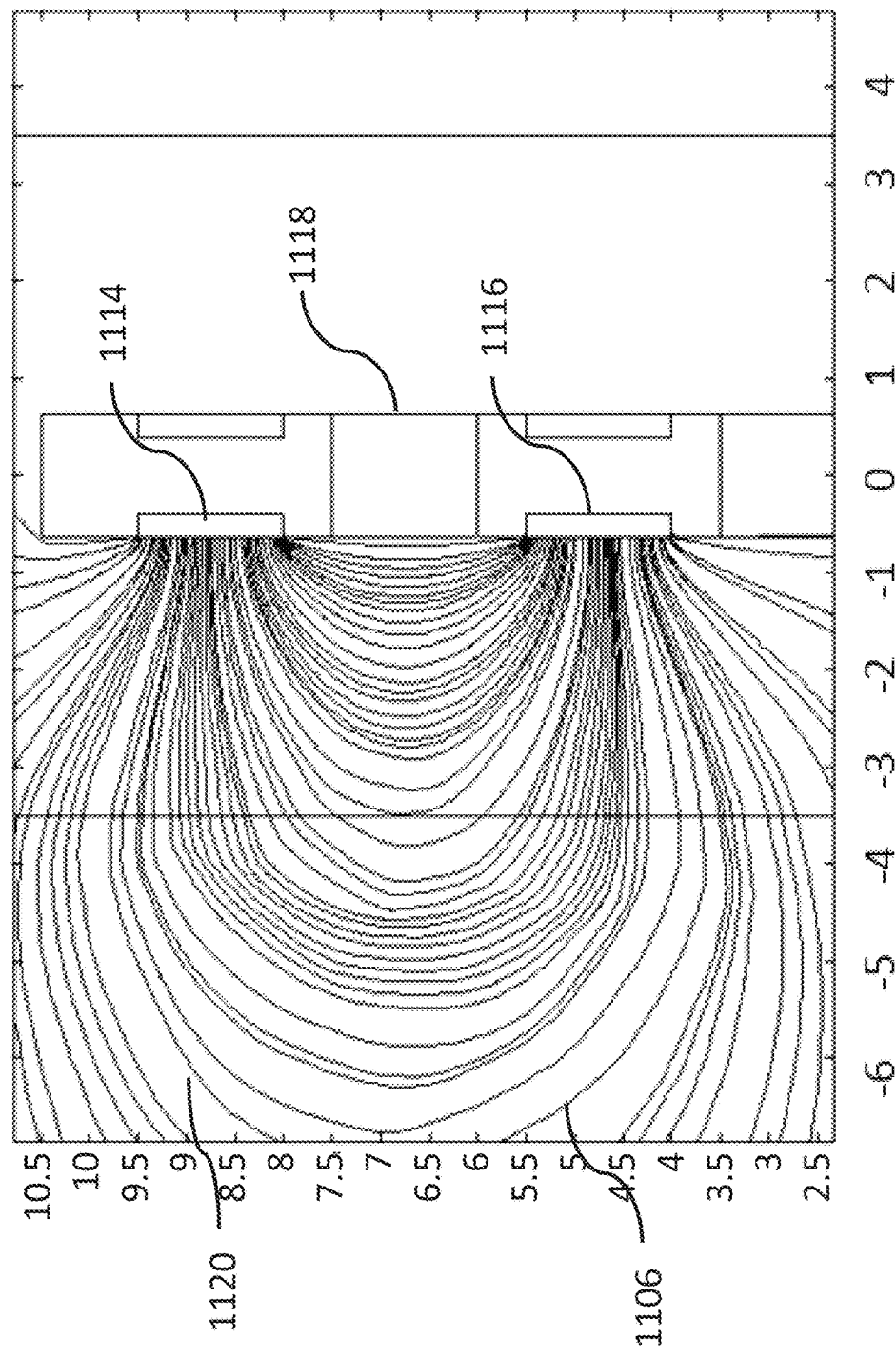

Reference is now made to FIG. 11E depicting electric field application in the form of electric current by two segmented macro-electrode contacts, with a ring macro-electrode contact positioned between them, according to some embodiments of the invention. According to some exemplary embodiments, electric field 1120 is applied in the form of electric current by segmented ring macro-electrode contact 116, and is returned by segmented ring macro-electrode contact 1114. In some embodiments, between the two segmented macro-electrode contacts there is at least one ring macro-electrode contact 1118.

Reference now is made to FIG. 11F depicting electric field application in the form of electric current by ring macro-electrode contacts, according to some embodiments of the invention. According to some exemplary embodiments, electric field 1122 is applied in the form of electric current by ring macro-electrode contact 1126, and is returned by ring macro-electrode contact 1124. In some embodiments, between the two ring macro-electrode contacts there are at least two rows of segmented macro electrode contacts 1128. In some embodiments, the electric field is asymmetrical, with the field on one side of the lead is negligible compared to the field on the other side. In FIG. 11F the current density is in Ampere/cm3, and the colors designate the value of the current density.

Figure 11G:
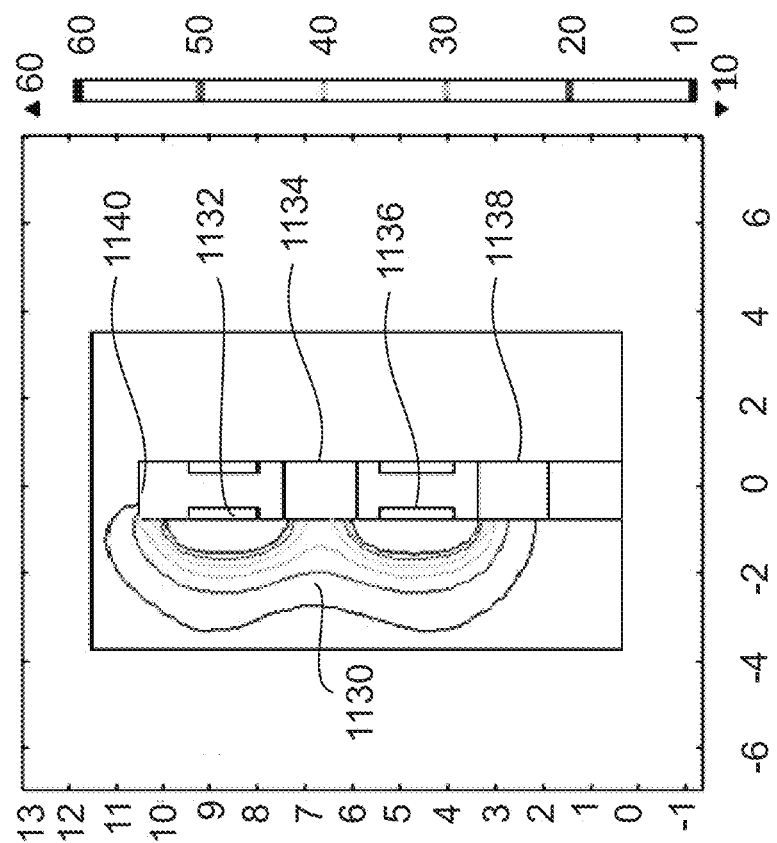

Reference now is made to FIG. 11G depicting electric field application in the form of electric current by ring macro-electrode contacts, according to some embodiments of the invention. According to some exemplary embodiments, electric field 1130 is applied in the form of electric current by ring macro-electrode contact 1138, and is returned by ring macro-electrode contact 1134. In some embodiments, between the two ring macro-electrode contacts there is at least one segmented macro electrode contact 1136. In some embodiments, an additional ring macro electrode contact 1140 can serve for current return. In some embodiments, these results in significant variations in the field along the longitudinal direction with a bi-modal distribution of the density field, i.e. there are two maxima, or two distinct regions in which the field is maximal, along the longitudinal axis. In addition, the electric field is asymmetrical, with the field on one side of the lead is negligible compared to the field on the other side. In FIG. 11G the current density is in Ampere/cm3, and the colors designate the value of the current density.

Exemplary Short Circuitry

According to some embodiments, navigation lead is configured to be connected to an external recording device during lead insertion and navigation. In some embodiments, after the lead is in a desired location, the external device is disconnected and the lead is connected to an IPG. In some embodiments, the lead is configured to be connected to IPG devices that have fewer channels than lead contact wires. Therefore lead wires are interconnected or short circuited to allow connection to an IPG device with few output channels.

Reference is now made to FIGS. 12A and 12B depicting a navigation lead connected to an external device for recording, and to an IPG device, according to some embodiments of the invention. According to some exemplary embodiments, lead 1140 comprises at least one micro-electrode contact 1142, and at least one macro-electrode contact, for example electrode contact 1144. In some embodiments, lead 1140 is connected to a recording device 1146, that has at least one input channel 1148, for example 6 input channels, via lead wires 1150, 1152, 1154, 1156, and 1158 during the lead navigation step. In some embodiments, once lead 1140 is in a desired depth and/or at a desired target tissue, device 1146 is disconnected and lead wires are connected to IPG 1164. In some embodiments, IPG 1164 has at least one output channel, for example 3 output channels 1166. In some embodiments, to allow connection of 5 lead wires to 3 output channels in IPG 1154, lead wires 1156 and 1154 are interconnected to a combined wire 1160, and lead wires 1152 and 1150 are interconnected to combined wire 1162.

In some embodiments, the combined wires are connected to IPG 1164 output channels, in addition to lead wires that were not interconnected, for example lead wire 1158. According to some embodiments, IPG 1146 comprises a charge density circuitry, configured to check that the maximal charge density, which is calculated as an integral of current over time, will not be exceeded. According to some embodiments, each segmented macro-electrode contact has its own contact wire. In some embodiments, at least two segmented macro-electrode are interconnected to generate a larger electrode contact, configured to apply an electric field to a larger tissue area compared to the electric field applied by a single segmented macro-electrode contact. In some embodiments, combining macro-electrode contacts allows to apply a similar electric field through several macro-electrode contacts.

According to some embodiments, a element connector is used to connect contact lead wires to recording device or to IPG device. In some embodiments, the connector comprises electric contacts according to the electric connection standards of the recording device and/or the electric connection standards of the IPG. In some embodiments, the connector element is configured to short-circuit lead wires by interconnecting at least two wires to a single combined wire.

In some embodiments, lead wires are connected to two cables, one recording cable is connected to a recording device, and an IPG cable is disconnected from the IPG during navigation. In some embodiments, prior to electric field application by the IPG, lead is disconnected from recording cable and is connected through IPG cable to the IPG. In some embodiments, during electric field application by the IPG, the recording cable is capped.

Exemplary Automatic Navigation and/or Mapping

According to some exemplary embodiments, automatic mapping algorithms, for example as described in WO2016182997, record signals received from the surrounding tissue along the lead insertion trajectory, and provide, for example as an output signal a functional "tag" or "state" associated with each or some depth positions along the trajectory. In some embodiments, assigning a tag for each or some depth position allows, for example to functionally map the tissue along the lead insertion trajectory and/or in a distance of up to 1 to 5 mm from the insertion trajectory. The term "functional" here relates to the properties of the tissue as inferred from the electrophysiological behavior of the tissue, and is different from "anatomical" which relates to the position of the tissue being mapped and its composition as can be understood from available imaging contrast techniques.

According to some exemplary embodiments, the automatic control of the micro drive which accurately inserts the lead into the tissue is based on the automatic mapping algorithm. In some embodiments, the automatic control means that based on the assigned functional tag or tags, and optionally according to a set of predetermined instructions, the drive step-size and/or or the drive speed are updated. For example, when the tagging is such that the lead is distant from a target which requires fine, high resolution mapping, the step size and/or speed is automatically adjusted to be large, e.g. 0.5 mm step size or larger, or 1 mm step size or larger, or a speed of 0.5 mm per second or larger, or 0.25 mm per second or larger, such that the time spent on mapping that region is minimized. In some embodiments, when the tagging is such that the lead is within or near a target area in which a high resolution mapping is required, the step size and/or speed is automatically adjusted to be small, e.g. 0.025 mm or smaller, or 0.1 mm or smaller, or a speed of 0.01 mm per second or smaller, or 0.05 mm per second or smaller, such that the target area is mapped with a desired high resolution.

Reference is made to FIGS. 13A and 13B depicting the identification of multiple spatially differentiated, or axis-shifted trajectories inferred from a lead's single insertion trajectory, according to some embodiments of the invention. In some embodiments, at least one trajectory is inferred from at least two insertion trajectories.

According to some exemplary embodiments, for example as shown in FIG. 13A, lead 1300 is inserted into the brain tissue along trajectory 1304. In some embodiments, at least one microelectrode, for example microelectrodes 1302 and 1303 record signals from the surrounding tissue at different depth positions along the insertion trajectory 1304. In some embodiments, based on the recorded signals from the microelectrodes, a plurality of axis-shifted trajectories are mapped, for example trajectory 1306 which is based on signals from microelectrode 1303 and trajectory 1308 which is based on signals from microelectrode 1302.

According to some exemplary embodiments, for example as shown in FIG. 13B a plurality of axis-shifted trajectories are calculated by signals derived from bi-polar macro electrode pairs. In some embodiments, a bi-polar pair of macro electrodes, for example macro electrodes 1312 and 1314 record signals from the surrounding tissue during the insertion of lead 1310 into the brain. In some embodiments, an axis-shifted trajectory, for example trajectory 1316 is calculated and/or determined based on the bi-polar measured signals.

According to some exemplary embodiments, the functional mapping, at each or in some depth positions is based on signals recorded and processed to extract signal features. In some embodiments, processing is comprised of rectification, for example full-wave rectification and/or filtering and/or normalization with respect to features extracted from previously recorded signals, and/or 1/f correction and estimation of power spectral density. In some embodiments, the signal features comprised of the mean signal energy or magnitude, inferred from the root-mean-square (RMS) or normalized root-mean-square (nRMS), signal power at a range of frequency bands, for example, delta band [1-4 Hz], theta band [4-8 Hz], alpha band [8-12 Hz], beta band [12-35 Hz], and/or gamma band [30-80] Hz, and/or high-gamma band [80-200 Hz].

A possible advantage of using the beta band is that the activity in the basal ganglia is correlated with symptoms of Parkinson's Disease (PD), and that stimulating the STN of a PD patient leads to effective symptom relief when the stimulation is delivered in a region of significant beta oscillations, according to several studies. In some embodiments, using beta band filtering for the processing of the signals allows, for example to identify regions with significant beta oscillations and to direct the therapeutic stimulation to these regions.

In some embodiments, the signal features may alternatively or additionally include spike rates, typically based on detection of neuronal action potentials (also called spikes), where the detection is typically performed by calculating a positive or negative amplitude threshold and detecting amplitudes that cross the threshold. In some embodiments, The spike signals are usually found in the 300 Hz-10 KHz frequency range, and can be related to spikes probably elicited by a single neuron ("Single Unit Activity", "SUA") or to spikes elicited by a local population of neurons ("Multi Unit Activity", "MUA").

Reference is now made to FIGS. 13C and 13D, depicting functional mapping of the brain tissue based on signals recorded from a plurality of electrodes, according to some embodiments of the invention.

According to some exemplary embodiments, for example as shown in FIG. 13C the result of a functional tissue mapping is a series of functional tags which are associated with specific depth positions along the insertion trajectory of the lead. In some embodiments, trajectory 1320 comprises different sections of functional tags which are associated with specific depth locations, for example section 1322 of the insertion trajectory is associated with the tag of DLOR sub-region of the STN, and section 1324 is associated with the tag VMNR sub-region of the STN.

According to some exemplary embodiments, for example as shown in FIG. 13D, each of the tags is assigned to a depth position based on recording measurements 1326 from the surrounding tissue which are performed by at least one electrode or a combination of electrodes on the lead. In some embodiments, each recording electrode or combination of electrodes has a specific location on the lead, as shown in 1332 which generates a different mapping trajectory, for example trajectories 1328 and 1330 with different associated tags for the same depth position. In some embodiments, the difference in tagging between each trajectory is caused by the variation in spatial location of the calculated trajectory with respect to the trajectory of the lead central axis, for example lead 1321 and/or the combination of the recording electrodes.

In some embodiments, the multiple mapping trajectories provide a spatial mapping of the volume around the lead trajectory, which is useful for the user to obtain a more comprehensive understanding of the location of the lead relative to the surrounding tissue, leading to better decision making with regards to the optimal implantation location in the lead trajectory. For example, a user might want to position the lead in desired distance from specific brain targets to provide an optimal treatment. By mapping the volume around the lead trajectory the user can learn what is the distance and/or direction to these desired brain targets and is there an alternative insertion trajectory that can bring the lead to a desired position. Additionally, the spatial mapping may also indicate preferred directions in regions up to 10 mm, for example 1, 3, 5, 7 mm or any intermediate or larger value from the lead axis, such that directional stimulation current may be directed in a preferred direction, or a different, more optimal implantation trajectory may be inferred by the user or by an algorithm operated by the system.

According to some exemplary embodiments, an analysis, for example, statistical analysis, e.g. dynamic Bayesian network analysis, is used to assign a functional tag for each or some depth positions in the lead insertion trajectory. In some embodiments, the analysis is based on a machine learning algorithm. In some embodiments, the machine learning algorithm is capable of adjusting parameters of an intrinsic model based on a database of examples for example, to optimize algorithm outputs similarity to a human expert output. In some embodiments, the machine learning algorithm is used to train the system for example, to adjust model parameters according to the database of input signals and output human expert functional tagging, and optionally reach automatic mapping results that are similar to the human expert mapping. In some embodiments, the sub-thalamic nucleus target (STN), is assigned with a functional tag selected from a list of "White Matter", "Dorso-Lateral Oscialltory Region" (DLOR), "Ventro-Medial Non-oscillatory Region" (VMNR), and/or "Substantia Nigra."

According to some exemplary embodiments, and further to WO2016182997, the mapping algorithms include one or more of the following Dynamic Bayesian Networks, artificial neural networks, deep learning networks, structured support vector machine, gradient boosting decision trees and long short term memory (LSTM) networks. The method described in WO2016182997 is a generalization of the Hidden Markov Model (HMM) and serves as another example of how to utilize a trained system in the mapping process.

According to some exemplary embodiments, in this method, based on recorded neurophysiological response by the lead, a plurality of predetermined observation elements, and/or input features, are calculated and Bayesian Networks are constructed for each observation element thereby creating a Dynamic Bayesian Network including the plurality of the predetermined observation elements. In some embodiments, based on the Dynamic Bayesian Network and the observation elements, the current location is assigned with a functional tag, or state in the process model, with the highest probability. Optionally, previously assigned tags are updated upon recording neurophysiological data from a current depth, for example by comparing the likelihoods of complete alternative state paths from the beginning of the mapping process to a current depth, and selecting the most likely state path.

In some embodiments, based on the Dynamic Bayesian Network, a Factored Partially Observable Markov Decision Process is constructed, wherein the Partially Observable Markov Decision Process (POMDP) further comprises relations between the predetermined observation elements; and based on the POMDP, the micro drive step size and/or speed are updated such that further advancement of the lead along the insertion trajectory is according to the updated step size and/or speed.

In some embodiments, at least one alternative or additional algorithm is used in the discrimination task, and/or in a pre-processing stage, for example for preparing the data for improving the training performance. In some embodiments, the at least one alternative or additional algorithm includes Multi Class SVM, Decision trees, boosted decision stumps, principal component analysis and/or independent component analysis.

In some embodiments, signals recorded from at least one microelectrode or at least one macro electrode of the lead are used as input to the learning machines and to the algorithms. In some embodiments, signals derived from bipolar and/or differential and/or macro electrode LFP signals are used as input to the learning machines and to the algorithms. In some embodiments, signals derived from bipolar and/or differential and/or microelectrode LFP signals are used as input to the learning machines and/or to the algorithms. In some embodiments, signals derived from microelectrode and/or macro electrode spike signals are used as input to the learning machines and to the algorithms.

Optionally, the learning machines use the above mentioned algorithms for functionally tagging the tissue in the insertion trajectory of the lead or any tissue surrounding the insertion trajectory.

According to some exemplary embodiments, recording a plurality of signals, optionally simultaneously, from different macro electrodes and microelectrodes distributed along the lead axis and on different positions on the circumference of the lead allows for example, mapping of tissue which is based on signals from sources located at different tissue depths and/or different directions.

In some embodiments, the lead used to record the plurality of signals has only micro contacts or microelectrodes positioned on the lead surface, only macro contacts or macro electrodes disposed on the lead surface, or at least one micro contact and at least one macro contact disposed on its surface.

According to some exemplary embodiments, the mapping algorithm is applied to each recorded signal separately, and generates multiple mapping results, for example as shown in FIG. 13D. In some embodiments, these multiple mapping results represent multiple trajectories and allow for example, to provide a better support for a decision of a user regarding an optimal or a desired stimulation or implantation target by functionally mapping the brain tissue surrounding the lead.

According to some exemplary embodiments, the recorded signals are combined together before applying the mapping algorithm. In some embodiments, the mapping algorithm applied on the combined signal is a multi-channel algorithm which takes into consideration the different signal sources, optionally recorded simultaneously, when generating the map. A possible advantage of using the multi-channel algorithm is that the map is generated more quickly since it is based on combined signals recorded in a shorter time period compared to longer recordings of single signals.

The multi-channel algorithm may be constructed in several ways. In some embodiments, the multi-channel algorithm is constructed by starting from a single-channel algorithm, which accepts a set of input features calculated from neurophysiological signals recorded along a single recording trajectory, e.g. recorded by a single electrode or a single bi-polar electrode pair, and outputs the most likely tags per each depth. In some embodiments, this single-channel algorithm is then expanded by expanding the input features set to include input features recorded along the multiple recording trajectories, e.g. by multiple electrodes or multiple bi-polar electrode pairs. In some embodiments, expanding the input features means defining a new model which is then trained on a database of multi-channel recordings along insertion trajectories in relevant surgical procedures. In some embodiments, once trained, the algorithm accounts for the multiple signals recorded on the multiple recording trajectories, and outputs the most likely state for the current depth, or most likely state path for the current and previous depths.

In some embodiments, the multi-channel algorithm differs more substantially from a single-channel algorithm, as it incorporates prior knowledge about relations between the different channels. For example, two or more channels may be considered to be related, e.g. by facing similar directions or opposite direction. Then, in some embodiments, signal features derived from these related channels may be jointly processed, or lumped together, to a single input feature in the multi-channel algorithm. Alternatively in some embodiments, specific signal features derived from two or more channels may be lumped in one way, to obtain one lumped input feature, and other signal features derived from the two or more channels may be lumped in a different way to a second lumped input feature. Further alternatively in some embodiments, knowledge of the relation between channels may be used to define a set of rules, or prior probability distributions, regarding the likelihood or reliability of a possible observations. For example, it is may be not likely that a first electrode, more proximal than a second electrode to reach a certain deep neural structure before the second electrode reaches that structure. Therefore, in some embodiments, the prior probability distribution for an observation that supports the proximal electrode is in the state related to the deep neural structure, while the more distal electrode has not yet reached that state, may be defined as very low, or even zero.

Reference is now made to FIG. 13E describing the generation of a single trajectory which is based on multiple recording measurements, according to some embodiments of the invention.

According to some exemplary embodiments, electrodes and/or different electrode combinations record a plurality of signals 1326 along the insertion trajectory of lead 1321. In some embodiments, the plurality of signals are combined and the combined signal is used as an input for a multi-channel algorithm which generates a single trajectory 1332 which includes functional tags for different depth positions and for tissue placed in varying distances from the lead 1321.

According to some exemplary embodiments, at least one additional or alternative trajectory is selected following the mapping procedure. In some embodiments the additional or alternative trajectory is based on directional signals, for example signals recorded by micro electrodes which face a specific horizontal plane (i.e. perpendicular to axial) direction, and/or based on macro electrodes which face a specific direction and/or based on bi-polar signals between the micro or macro electrodes. In some embodiments, the directional signals reflect neuronal activity signals—LFPs and/or MUA signals-originating from specific directions.

According to some exemplary embodiments, the functional mapping of the directional signals indicate the user by a functional map of the surrounding brain tissue that the alternative trajectory is a better trajectory for delivery an efficient DBS treatment. In some embodiments, the user is provided with an indication in space for the location of the alternative trajectory.

According to some exemplary embodiments, the directional signals are analyzed manually or by a semi-automatic or by a fully automatic algorithm to map and provide an indication for the more effective alternative trajectory. In some embodiments, identification of the more effective alternative trajectory is based for example, on a better correlation between the mapping results of the alternative trajectory and mapping results that were found to be optimal for reaching a desired treatment outcome.

According to some exemplary embodiments, a semi-automatic algorithm is an algorithm which requires, or allows, some user input to perform its task. In some embodiments, a user must push or hold a button to allow the system to continue its operation. In some embodiments the user is required to actively approve the algorithm's suggestion to perform a stimulation test at a specific location, by clicking on a specific button in the software interface. Alternatively or additionally, the user has the capability to mark a specific recording at a specific location as unusable, e.g. due to high levels of noise contamination, and thus instruct the algorithm to disregard the signals recorded there.

According to some exemplary embodiments, the directional signals are recorded from sources located at a distance of at least 0.2 mm from the measuring electrode contact, for example 0.4, 0.5, 0.6, 1, 1.2, 1.5, 2 mm or any intermediate or larger value. In some embodiments, LFPs, bi-polar and/or differential LFPs signals are sensitive to neuronal signal sources at these distances. Additionally, LFPs, bi-polar and/or differential LFPs signals are sensitive to signals originating from more proximal sources.

According to some exemplary embodiments, at least two types of signals which are sensitive to distances >0.2 mm from the measuring electrode are recorded. In some embodiments, one of the signals is the MUA spiking activity of neuronal populations, which is sensitive to sources as far as ~0.5 mm. In some embodiments, the second is LFPs, which are sensitive to sources as far as centimeters from the measurement. Optionally, Bi-polar, or differential (digital or analog computation) LFPs reject signals from sources that are distant enough to arrive at a similar phase to the two recording contacts, and thus are sensitive to signals originating at sources at an intermediate and relevant range.

According to some exemplary embodiments, one way to "isolate" the neuronal activity at such distances and different directions, from the activity in the lead vicinity in its current trajectory, is to compare between types of signals recorded on several electrodes facing different directions. For example, differential LFPs recorded between two electrodes at the same depth but facing opposite directions will highlight signal sources located along the virtual line connecting the two contacts and extending to each direction. In some embodiments, this measurement is combined with the SUA or MUA measurement in these electrodes, which are sensitive to more local sources. For example, if the differential LFP recording shows a significant relevant signal component (e.g. high beta-power indicating potentially good DBS target) and the MUA signals show no such component on one side and a weak component on the second side, it can be inferred that the source of the signal is located in the direction of the second side, and not in the immediate vicinity of the lead (the MUA is weak), but at a distance that is about the maximal MUA effective distance. Alternatively, several mono-polar and bi-polar LFP recordings are added and subtracted in such a way that highlights signals originating at a specific direction, and possibly distance, and may also alternatively be compared with SUA and MUA activity from electrodes facing the specific directions and other directions as reference.

In some embodiments, the at least one alternative trajectory is identified at a distance of at least 0.5 mm from the electrode contacts on the lead circumference, for example 0.8, 0.9, 1, 1.2, 1.5, 2 mm or any intermediate or larger distance from the electrode contact. In some embodiments, the at least one alternative trajectory is positioned in a distance of at least 1 mm from the lead insertion trajectory, for example 1.2, 1.4, 1.5, 1.7, 2, 2.5 mm or any intermediate or larger distance from the lead insertion trajectory.

In some embodiments, modifying the insertion trajectory to an alternative trajectory in step smaller than 0.2 mm is less practical, whereas alternative trajectories located at a distance larger than 1 mm from the insertion trajectory are more practical and valuable to the user.

Exemplary Functionally Mapping Methods

Reference is now made to FIG. 14A describing the modification of an existing model for a functional tissue map using machine learning techniques.

According to some exemplary embodiments, a model of a tissue map which includes functional annotations of the tissue is provided at 1402. In some embodiments, expert labeled data from surgical procedures is collected at 1404 and stored optionally in a database.

According to some exemplary embodiments, machine learning algorithms are applied and modify the model provided at 1402 based on the collected expert-data at 1406.

According to some exemplary embodiments, the modified model or trained model is used for mapping during the surgery at 1408. In some embodiments, the modified model is used in a surgery in a new patient to provide online mapping of the tissue, based on the recording of the electrical neuronal activity.

According to some exemplary embodiments, in machine learning, there is usually a model, for example the model provided at 1402, in which there are two or more states, and often the goal is to distinguish between these states based on a set of input features. This distinction is then used as the output of the system, and it is based on an internal relation between the input features and the model states.

In some embodiments, in order for the learning, or training, to occur, a database is required, for example a database which includes the expert-labeled data collected from surgical procedures described at 1404, which can include examples of inputs and output, and sometimes only the inputs. A software code defines a procedure, by which the computer can train on the database ("training set"), so that the relation between the input features and the output states can be learned. The different machine learning methods differ in the models they are based on, the type of relations between inputs and outputs, and the procedures for training on the training set.

An example for a machine learning method is the Hidden Markov Model (HMM), in which the model describes a random process occurring on a chain of states, which are generally not known (hence hidden), and are associated with observations which are at least partially known. Optionally, the relations between the states, and between the states and observations are statistical. That is, the transition from state —i— to state —j— can occur with a certain probability, or can not occur, and similarly, there is a probability for each observation K, given the process is at a given state —j—. These two relations are given in the Transition Matrix, T, in which element tij is the probability for transition from state i state j, and in the Emission Matrix E, in which element eik is the probability to see observation k, given the process is in state i. Another parameter is the prior probability to begin in a certain state —k—, $\pi\_k$, before the first observation is provided.

In some embodiments, the HMM model, as is defined by the possible states and observations, is given to the system based on prior knowledge. For example, for navigating in the STN, the states can be White Matter, STN DLOR, STN VMNR and SNR. In some embodiments, the observations are vectors of binned quantification of signal features, in which the elements of the vector are the measured variables, e.g. [Spike Rate, NRMS, Beta PSD, LFP Beta power], and the values are their binned quantification e.g. [High, Medium, Low, Low], or [5, 3, 1, 1]. In some embodiments, the observations are structured in a sequence, and optionally the required training is to learn the best relation between the sequences of observations, which are the input and the sequences if states which is the output. Once trained, the computer can use the transition and emission matrices to estimate the most likely sequence of states, given a sequence of observations.

In some embodiments, given a sequence of observations and the matrices T, E & π, the most likely sequence of states is found using the Viterbi algorithm, as is defined for example in "A Tutorial on Hidden Markov Models and Selected Applications in Speech Recognition", by LAWRENCE R. RABINER, published in PROCEEDINGS OF THE IEEE, VOL. 77, NO. 2, February 1989. In short, this algorithm applies the following steps:

1. Initialize: for every state —i— calculate initial probability, $\delta$ and backtrack value $\psi$:

$$\delta_1(i) = \pi_i e_{iO(1)}$$

$$\psi_1(i) = 0$$

2. Recursion: for every state —j— and time step —n—, calculate:

$$\delta_n(j) = \max_i \{[\delta_{n-1}(i) t_{ij}] e_{jO(n)}\}$$

$$\psi_n(j) = \operatorname{argmax}_i \{\delta_{n-1}(i) t_{ij}\}$$

3. Termination: Find most likely last state (state at time step n=N):

$$P^* = \max_i \{\delta_N(i)\}$$

$$S_N^* = \operatorname{argmax}_i \{\delta_N(i)\}$$

4. Find most likely sequence in backtrack:

$$S_n^* = \psi_{n+1} \{S_{n+1}^*\}$$

In this description e & t are elements of the emission and transition matrix respectively, $\{O(1), O(2), \ldots, O(N)\}$ is the observation sequence and $\{S^*(1), S^*(2), \ldots, S^*(N)\}$ is the most likely state sequence, given the model and the observations.

According to some exemplary embodiments, there are generally two types of possible learning methods—supervised and unsupervised. In supervised learning, the database includes the correct outputs as estimated by a human expert. The goal of learning is then to apply a learning rule in order to tune the model parameters, i.e. Transition matrix, Emission matrix and initial state probability values in the case of HMM, which lead to a minimal error between the output of the machine and of the human expert. In unsupervised learning, the "true" values are not given, and then the goal of learning is usually to reach convergence, i.e. a situation in which applying the learning rule does not result in a significant modification of model parameters.

In some embodiments, supervised learning can be carried out by counting the occurrence frequencies. That is, scanning the database and finding, e.g. the ratio between the number of times in which the expert defined the HMM process to transition from state i to state j, and the number of times the expert defined the HMM to be in state i. This could be defined as the probability to transition from state i to state j:

$$\hat{t}_{ij} = \frac{\#\{s_n = i, s_{n+1} = j\}}{\#\{s_n = i\}}$$

The same can be done for the emission matrix and for the initial probability array.

According to some exemplary embodiments, unsupervised learning can be carried out by a variety of algorithms. A well-known algorithm, used to train a variety of models with different probability distributions, is the Expectation Maximization algorithm. Another, less elaborate method is the Maximum likelihood method. These are both known to data scientists and engineers skilled in the art, and are also described in many publications. For a detailed explanation of the Expectation Maximization method for an HMM, the reader may turn to the paper by LAWRENCE R. RABINER mentioned above.

Reference is now made to FIG. 14B describing the generation of multiple mapped projections from multiple recorded signals, according to some embodiments of the invention.

According to some exemplary embodiments, a lead in inserted into the brain at 1410. In some embodiments, a navigational algorithm initializes with initial determined step-size at 1412. In some embodiments, a motorized drive inserts the lean into the brain tissue according to the determined step size at 1414.

According to some exemplary embodiments, multiple signals are recorded using multiple electrodes or electrode combinations at 1416. In some embodiments, the signals are analyzed separately at 1418, to generate multiple mapped trajectories. In some embodiments, the location is determined for each signal trajectory separately. In some embodiments, the step-size is determined based on the determined location. In some embodiments, the location tag calculated at the specific depth in 1418 is presented to the user immediately after it is calculated. In some embodiments, the set of tags calculated at current and previous locations is continually displayed to the user. In some embodiments, the set of previously calculated tags may be changed retroactively, based on signals recorded and analyzed from a new location, leading to a recalculation of tags in previous locations.

According to some exemplary embodiments, if the mapping is finished at 1420, for example by an indication received from the user, the system performs an additional step of inferring the suspected optimal implantation location at 1422. In some embodiments, if mapping continues then the drive inserts the lead into the brain at 1414 according to the updated step size. The system may finish the mapping may automatically, for example when one or more mapping tags indicate exit of the electrode from the target region.

Reference is now made to FIG. 14C describing generating a single trajectory from multiple recordings, according to some embodiments of the invention.

According to some exemplary embodiments, a lead is inserted into the brain at 1424. In some embodiments, a navigational algorithm is initialized with an initial step-size at 1426. In some embodiments, the drive motor inserts the lead into the brain according to the step size at 1428. In some embodiments, multiple signals are recorded from the surrounding brain tissue by electrodes or electrode combinations at 1430.

According to some exemplary embodiments, the recorded signals are analyzed using a multi-channel model at 1432. In some embodiments, based on the multi-channel model a single integrated trajectory is generated and the location of different tissues and functional regions surrounding the lead is determined. In some embodiments, the location tag calculated in 1432 is presented to the user immediately after it is calculated. In some embodiments, the set of tags calculated at current and previous locations is continually displayed to the user. In some embodiments, the set of previously calculated tags may be changed retroactively, after signals are recorded and analyzed from a new location, leading to a recalculation of tags in previous locations.

Additionally or optionally, the step size is updated based on the generated trajectory. In some embodiments, if the mapping procedure is finished, for example if the mapping is stopped by the user at 1434, then the system performs an additional step of inferring the suspected optimal implantation location. Alternatively, if mapping continues then the motor drive inserts the lead into the brain at 1428 according to the updated step-size.

Exemplary Distal Coupler

According to some exemplary embodiments, the lead, for example the navigating lead comprises a distal coupler, positioned in the distal end of the lead body, in a close proximity to the lead's distal tip. In some embodiments, the distal coupler includes at least one opening and/or at least one internal channel for accurately directing at least one microelectrode to a desired position on the lead circumference or to the lead tip. Alternatively or additionally, the distal coupler allows for example, to position a plurality of microelectrodes and/or macro electrodes in a desired orientation relative to each other and/or relative to a marking point on the lead circumference. In some embodiments, accurately positioning the microelectrodes on the outer surface of the lead is essential for generating accurate maps, since each electrode is associated with a specific depth position and orientation during the mapping process. For example, in some embodiments the depth location should be accurate to 0.1 mm, so that the depth mapping would be considered very accurate.

According to some exemplary embodiments, the distal coupler is associated with micro electrodes formed from micro wires. In some embodiments, the micro wires are electrically connected to an electrode on the lead surface and then extend through the internal lumen of the lead to be connected to a conductor and/or to an acquisition system. In some embodiments, the micro wire is guided through the channel and/or opening in the distal coupler to a desired position on the external surface of the lead.

In some embodiments, at least two different electrodes are guided through spaced apart channels and/or openings in the distal coupler to desired positions on the lead external surface. In some embodiments, the distal coupler allows for example, to accurately position the at least two electrodes in desired positions on the lead outer surface and/or in desired positions relative to each other or relative to an external element connected to the lead.

Reference is now made to FIG. 15 depicting a distal coupler, according to some embodiments of the invention.

According to some exemplary embodiments, lead 1500 comprises a distal coupler 1502 positioned within the internal lumen 1504 of the lead. In some embodiments, the distal coupler comprises at least one channel 1506, for example an axial channel, which is shaped and sized to direct at least one micro electrode to a specific location on the lead surface. In some embodiments, channel 1506 directs microelectrode 1510 to a specific location on the distal tip 1508 of the lead. Additionally or alternatively, the distal coupler 1502 comprises at least one opening or at least one channel for directing a micro electrode, for example microelectrode 1512 to a specific location on the lead circumference.

A possible advantage of the distal coupler is that it allows a repetitive, predictable and good-yield process of locating the electrodes on the lead surface for mapping the tissue with a desired accuracy. In some embodiments, the distal coupler allows different manufacturing processes. For example, the electrodes do not have to be located inside a polymer lead body pre-processed to have holes accurately placed. In some embodiments, the electrodes are positioned on micro wires that are held by the distal coupler, and then some material, for example a medical grade epoxy, is cast over the wires and distal coupler according to a pre-determined mold. In this case, the major part of the lead body is still composed of a flexible biocompatible polymer, but the distal tip is made from the cast material. A possible advantage of the casting material is that it is more tolerant to further processing steps such as grinding the material, to ensure that the electrodes are flush to the lead body.

In some embodiments, the distal coupler also potentially increases the manufacturing yield and the reliability of the device, since the distal coupler allows the wires to be short and protected and therefore less susceptible to damage during the assembly process—hence higher yield— and less susceptible to damage during the shipping and user handling of the device, hence higher reliability.

Exemplary Internal Shield

According to some exemplary embodiments, the lead comprises an internal shield, optionally in the form of a layer for shielding the electrode conductors placed within the lead interior lumen from external electro-magnetic fields. In some embodiments, the internal shield is made from a conductive material, and functions as an electro-magnetic shield or a Faraday cage which reacts with the external electro-magnetic fields, and protects the internal electrode conductors from the effect of these electro-magnetic fields. This helps to improve the sensitivity by increasing the signal-to-noise ratio of the measured signals.

In some embodiments, the signal-to-noise ratio is increased when recording low frequency signals for example, LFP signals in frequencies between 1-300 Hz, which are often highly contaminated by external electro-magnetic noise. An example for a source for such a noise is the electric network noise, which has a fundamental component at about 50 or 60 Hz, and in harmonics of 100, 150, 200, 250 . . . or 120, 180, 240 etc.

According to some exemplary embodiments, the shield covers at least 70% of the electrode conductors length along the lead axis, for example 80%, 85% or 90% or any intermediate or larger coverage percentage. In some embodiments, in order to reach an optimal signal-to-noise ratio, the shield should provide coverage >80% of the length of the electrode conductor, preferably >90%.

Reference is now made to FIGS. 16A and 16B describing an internal shield, according to some embodiments of the invention.

According to some exemplary embodiments, lead 1600 comprising an internal electro-magnetic shield within the internal lumen of the lead. In some embodiments, the shield is positioned between the outer lead body 1602 and the conducting wires connected to the electrodes. In some embodiments, the shield surrounds at least 70% of the entire length of the conducting wires as described above. In some embodiments, for example as shown in FIG. 16B, the shield 1604 is electrically connected to an electrically conductive section, for example plate 1610 on the outer surface of the lead 1600. In some embodiments, the conductive section is connected to a differential amplifier that allows, for example to subtract electrical noise received by the shield from the signals delivered by the electrode wires. In some embodiments, the conductive section is connected to the system ground.

According to some exemplary embodiments, the shield is an electrically conductive braided or coiled shield or an electrically conductive mesh material, optionally made from electrically conductive wires. In some embodiments, the braided shield is shaped and sized to be positioned inside the internal lumen of the lead, and to surround at least part of the electrode conductors.

According to some exemplary embodiments, the shield comprises at least one connector for example, a male and/or a female connector for connecting the shield to an external system. For example, in some embodiments the shield is electrically connected to the recording system ground, and/or provides a reference signal input for example, a reference signal input to a differential amplifier. In some embodiments, the reference signal input is subtracted from the delivered signal, for example to remove electromagnetic noise from the delivered signal.

According to some exemplary embodiments, the shield comprises at least one channel and/or at least one opening and serves as a distal coupler for directing micro wires to a desired location on the lead surface, as described above in the exemplary distal coupler section.

It is expected that during the life of a patent maturing from this application many relevant leads will be developed; the scope of the term leads is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A brain navigation system, comprising:
   a lead having an elongated lead body with a distal end shaped to penetrate into brain tissue, comprising:
   at least one micro-electrode micro contact positioned on an outer surface of said elongated lead body close to said distal end;
   at least one macro-electrode contact positioned on an outer surface of said lead body, located proximal to said at least one micro-electrode micro contact on said elongated lead body; wherein said at least one micro-electrode micro contact and said at least one macro-electrode contact are located at different angular positions on said outer surface of said lead body, and are configured to record directional electrical signals from brain tissue surrounding said lead during navigation of said lead;
   a control system electrically connected to said lead, comprising a memory, wherein said control system is configured to receive said directional electrical signals from said at least one microelectrode micro contact and said at least one macro-electrode contact, to store said received electrical signals in said memory, to functionally map said brain tissue during navigation of said lead based on said recorded electrical signals, and to deliver a directional electric field to a target brain tissue region by at least one microelectrode micro contact of said at least one microelectrode micro contact and at least one macro-electrode contact of said at least one macro-electrode contact.

2. The system according to claim 1, wherein said lead is used for navigation in the spinal cord.

3. The system according to claim 1, comprising at least one additional micro-electrode micro contact located at a distal tip of said elongated lead body.

4. The system according to claim 1, wherein said at least one macro-electrode contact comprises at least one segmented electrode contact having at least two segments.

5. The system of claim 1, wherein said control system is configured to generate depth fingerprints for locations along the brain navigation lead insertion trajectory using the recorded electrical signals.

6. The system of claim 5, wherein said control system is configured to analyze and combine depth fingerprints of several locations to generate an electrical activity map of neuronal populations at different locations in the brain.

7. The system of claim 5, wherein said control system is configured to determine at least one additional insertion trajectory using the generated depth fingerprints.

8. The system of claim 5, wherein said control system is configured to determine a target depth for delivery of an electric field by said at least one macro-electrode contact based on said generated depth fingerprints.

9. The system of claim 1, wherein a diameter of each of said at least one micro-electrode micro contact is in a range of 5-50 micron.

10. The system of claim 1, wherein said at least one micro-electrode micro contact comprises at least 3 micro-electrode micro contacts positioned along said outer surface of the lead body at said different angular positions facing different brain regions around the brain navigation lead, to allow directional recording of electric activity from the different brain regions as the brain navigation lead is inserted along an inserting trajectory into the brain.

11. The system according to claim 1, wherein said at least one microelectrode micro contact comprises at least 3 microelectrode microcontact distributed at different angular positions on said outer surface of said lead body, and wherein at least one microelectrode micro contact of said at least 3 microelectrode micro contacts and said at least one macro-electrode contact are used for both directional recording of electrical signals from brain tissue surrounding said lead during navigation, and for delivery of directional electric field to said target brain tissue.

12. The system according to claim 11, wherein said at least 3 microelectrode micro contacts comprise at least 4 microelectrode micro contacts positioned along said outer surface of the lead body at different angular positions.

13. The system according to claim 11, wherein said at least one macro-electrode contact and said at least 3 microelectrode micro contacts are configured to be used simultaneously during navigation of said lead.

14. A method for recording and applying an electric field to brain tissue using a brain navigation lead having an elongated shaft with a distal end-shaped to penetrate into brain tissue, comprising:
  advancing said brain navigation lead to a target tissue region inside a brain along an insertion trajectory, wherein said brain navigation lead comprises at least one macroelectrode contact and at least one microelectrode micro contact positioned along an outer surface of the elongated shaft at different angular positions;
  recording electrical activity of tissue surrounding said brain navigation lead by said at least one microelectrode micro contact and said at least one macroelectrode contact during said advancing;
  storing said recorded electrical activity in a memory;
  functionally mapping brain tissue along said insertion trajectory during said advancing based on said recorded electrical activity;
  determining that said at least one macro-electrode contact and said at least one microelectrode micro contact are at a known location relative to said target tissue region; and
  applying a directional electric field to said target tissue region by at least one macro-electrode contact of said at least one macro-electrode contact and at least one microelectrode micro contact of said at least one microelectrode micro contact, based on said determining.

15. The method of claim 14, further wherein said recording comprises recording electrical activity of said tissue following an electric field application by the at least one macro-electrode contact and said at least one microelectrode micro contact.

16. The method of claim 14, further comprising:
  determining electric field application parameters based on said recorded electrical activity.

17. The method according to claim 14, wherein said determining comprises determining a target depth for electric field application based on said mapping results.

18. The method of claim 14, wherein said functionally mapping comprises generating depth fingerprints for locations along the brain navigation lead insertion trajectory using the recorded electrical activity, and wherein said determining comprises determining that said at least one macro-electrode contact and said at least one microelectrode micro contact configured to deliver said electric field to brain tissue are at a target depth for delivery of said electric field based on said generated fingerprints.

19. The method of claim 18, wherein said mapping comprises combining depth fingerprints of several locations to generate an electrical activity map of neuronal populations at different locations in the brain.

20. The method of claim 14, wherein said functionally mapping comprises generating an electrical activity map of neuronal population at different locations in the brain along said insertion trajectory.

* * * * *